US010174339B2

(12) United States Patent
Van Der Weerden et al.

(10) Patent No.: US 10,174,339 B2
(45) Date of Patent: Jan. 8, 2019

(54) MODIFIED PLANT DEFENSINS USEFUL AS ANTI-PATHOGENIC AGENTS

(71) Applicant: HEXIMA LIMITED, Melbourne (AU)

(72) Inventors: Nicole Van Der Weerden, Coburg (AU); Marilyn Anne Anderson, Keilor (AU)

(73) Assignee: Hexima Limited, La Trobe University (AU)

( * ) Notice: Subject to any disclaimer, the term of this patent is extended or adjusted under 35 U.S.C. 154(b) by 37 days.

(21) Appl. No.: 15/296,952

(22) Filed: Oct. 18, 2016

(65) Prior Publication Data

US 2017/0029842 A1    Feb. 2, 2017

Related U.S. Application Data

(62) Division of application No. 13/983,941, filed as application No. PCT/AU2012/000112 on Feb. 7, 2012, now Pat. No. 9,497,908.

(Continued)

(51) Int. Cl.
*C12N 15/82* (2006.01)
*A01H 5/00* (2018.01)
(Continued)

(52) U.S. Cl.
CPC ........... *C12N 15/8282* (2013.01); *A01H 5/02* (2013.01); *A01H 5/06* (2013.01); *A01H 5/08* (2013.01); *A01H 5/10* (2013.01); *A01H 5/12* (2013.01); *A01H 6/88* (2018.05); *A01H 15/00* (2013.01); *C07K 7/06* (2013.01); *C07K 14/415* (2013.01);
(Continued)

(58) Field of Classification Search
None
See application file for complete search history.

(56) References Cited

U.S. PATENT DOCUMENTS

| 4,767,777 A | 8/1988 | Bass et al. |
| 4,945,050 A | 7/1990 | Sanford et al. |

(Continued)

FOREIGN PATENT DOCUMENTS

| EP | 125468 | 11/1984 |
| JP | 10295380 | 11/1998 |

(Continued)

OTHER PUBLICATIONS

Payne, Jennifer AE, et al. "The plant defensin NaD1 introduces membrane disorder through a specific interaction with the lipid, phosphatidylinositol 4, 5 bisphosphate." Biochimica et Biophysica Acta (BBA)—Biomembranes 1858.6 (2016): 1099-1109. (Year: 2016).*

(Continued)

*Primary Examiner* — Lee A Visone
*Assistant Examiner* — Weihua Fan
(74) *Attorney, Agent, or Firm* — Knobbe, Martens, Olson & Bear, LLP

(57) ABSTRACT

This disclosure relates generally to the field of anti-pathogenic agents, including a modified defensin molecule with anti-pathogen activity. Genetically modified plants and their progeny or parts expressing or containing the modified defensin and anti-pathogen compositions for use in horticulture and agriculture and as animal and human medicaments are also provided.

10 Claims, 24 Drawing Sheets

Specification includes a Sequence Listing.

Related U.S. Application Data

(60) Provisional application No. 61/440,309, filed on Feb. 7, 2011.

(51) Int. Cl.
  *A01H 6/88* (2018.01)
  *C07K 14/415* (2006.01)
  *C07K 14/47* (2006.01)
  *A01H 5/02* (2018.01)
  *A01H 5/06* (2018.01)
  *A01H 5/08* (2018.01)
  *A01H 5/10* (2018.01)
  *A01H 5/12* (2018.01)
  *A01H 15/00* (2006.01)
  *C07K 7/06* (2006.01)

(52) U.S. Cl.
  CPC ...... *C07K 14/4723* (2013.01); *C07K 2319/21* (2013.01); *C07K 2319/95* (2013.01)

(56) References Cited

U.S. PATENT DOCUMENTS

| | | | |
|---|---|---|---|
| 5,004,863 | A | 4/1991 | Umbeck |
| 5,036,006 | A | 7/1991 | Sanford et al. |
| 5,100,792 | A | 3/1992 | Sanford et al. |
| 5,371,015 | A | 12/1994 | Sanford et al. |
| 5,482,928 | A | 1/1996 | De Bolle et al. |
| 5,538,525 | A | 7/1996 | Broekaert et al. |
| 5,689,043 | A | 11/1997 | Broekaert et al. |
| 5,773,694 | A | 6/1998 | Broekaert et al. |
| 5,773,696 | A | 6/1998 | Liang et al. |
| 5,981,840 | A | 11/1999 | Zhao et al. |
| 6,031,153 | A | 2/2000 | Ryals et al. |
| 6,121,436 | A | 9/2000 | Liang et al. |
| 6,147,281 | A | 11/2000 | Garcia-Olmedo et al. |
| 6,215,048 | B1 | 4/2001 | Liang et al. |
| 6,268,546 | B1 | 7/2001 | McBride et al. |
| 6,316,407 | B1 | 11/2001 | Liang et al. |
| 6,329,504 | B1 | 12/2001 | Liang et al. |
| 6,512,166 | B1 | 1/2003 | Harman et al. |
| 6,605,698 | B1 | 8/2003 | Van Amerongen et al. |
| 6,653,280 | B2 | 11/2003 | Liang et al. |
| 6,677,503 | B1 | 1/2004 | Bidney et al. |
| 6,680,424 | B2 | 1/2004 | Atkinson et al. |
| 6,770,750 | B2 | 8/2004 | Oh et al. |
| 6,784,337 | B1 | 8/2004 | Atkinson et al. |
| 6,806,074 | B2 | 10/2004 | Anderson et al. |
| 6,855,865 | B2 | 2/2005 | Famodu et al. |
| 6,864,068 | B2 | 3/2005 | Rees et al. |
| 6,909,032 | B2 | 6/2005 | Manners et al. |
| 6,911,577 | B2 | 6/2005 | Simmons et al. |
| 6,916,970 | B2 | 7/2005 | Liang et al. |
| 6,946,278 | B2 | 9/2005 | Anderson et al. |
| 6,955,916 | B2 | 10/2005 | Anderson et al. |
| 7,041,877 | B2 | 5/2006 | Anderson et al. |
| 7,067,624 | B2 | 6/2006 | Manners et al. |
| 7,141,723 | B2 | 11/2006 | Chen et al. |
| 7,238,781 | B2 | 7/2007 | Famodu et al. |
| 7,297,840 | B2 | 11/2007 | Anderson et al. |
| 7,309,596 | B2 | 12/2007 | Anderson et al. |
| 7,410,796 | B2 | 8/2008 | Anderson et al. |
| 7,462,695 | B2 | 12/2008 | Dunse et al. |
| 7,528,293 | B2 | 5/2009 | Ali et al. |
| 7,544,541 | B2 | 6/2009 | Low et al. |
| 7,544,861 | B2 | 6/2009 | Anderson et al. |
| 7,589,176 | B2 | 9/2009 | Altier et al. |
| 7,592,433 | B1 | 9/2009 | Craik et al. |
| 7,728,190 | B1 | 6/2010 | Seale et al. |
| 7,785,828 | B1 | 8/2010 | Wu et al. |
| 8,252,898 | B2 | 8/2012 | Anderson et al. |
| 2002/0059658 | A1 | 5/2002 | Wei et al. |
| 2002/0144306 | A1 | 10/2002 | Liang et al. |
| 2003/0129720 | A1 | 7/2003 | Anderson et al. |
| 2003/0217382 | A1 | 11/2003 | Anderson et al. |
| 2004/0064850 | A1 | 4/2004 | Liang et al. |
| 2004/0073971 | A1 | 4/2004 | Bidney et al. |
| 2004/0111761 | A1 | 6/2004 | Bidney et al. |
| 2005/0058689 | A1 | 3/2005 | McDaniel |
| 2005/0273881 | A1 | 12/2005 | Simmons et al. |
| 2006/0150276 | A1 | 7/2006 | Anderson et al. |
| 2007/0150982 | A1 | 6/2007 | Chen et al. |
| 2007/0197474 | A1 | 8/2007 | Clinton et al. |
| 2007/0219147 | A1 | 9/2007 | Dunse et al. |
| 2007/0277263 | A1 | 11/2007 | Anderson et al. |
| 2008/0109924 | A1 | 5/2008 | Ali et al. |
| 2008/0134367 | A1 | 6/2008 | Anderson et al. |
| 2009/0069545 | A1 | 3/2009 | Anderson et al. |
| 2009/0083880 | A1* | 3/2009 | Anderson ........... C07K 14/415 800/279 |
| 2009/0093880 | A1 | 4/2009 | Justin |
| 2009/0188010 | A1 | 7/2009 | Dunse et al. |
| 2009/0197809 | A1 | 8/2009 | Anderson et al. |
| 2010/0068762 | A1 | 3/2010 | Craik et al. |
| 2010/0095408 | A1 | 4/2010 | Heath et al. |
| 2010/0218280 | A1 | 8/2010 | Anderson et al. |
| 2013/0047299 | A1 | 2/2013 | Anderson et al. |
| 2013/0263326 | A1 | 10/2013 | Heath et al. |
| 2013/0267459 | A1 | 10/2013 | Heath et al. |
| 2013/0269059 | A1 | 10/2013 | Heath et al. |
| 2015/0283204 | A1 | 10/2015 | Nicole et al. |

FOREIGN PATENT DOCUMENTS

| | | |
|---|---|---|
| WO | WO 1987/03303 | 6/1987 |
| WO | WO 1990/13224 | 11/1990 |
| WO | WO 1991/10363 | 7/1991 |
| WO | WO 1993/04586 | 3/1993 |
| WO | WO 1994/13810 | 6/1994 |
| WO | WO 1994/16076 | 7/1994 |
| WO | WO 1997/37024 | 10/1997 |
| WO | WO 1998/00023 | 1/1998 |
| WO | WO 2000/11175 | 3/2000 |
| WO | WO 2000/11196 | 3/2000 |
| WO | WO 2000/68405 | 11/2000 |
| WO | WO 2000/78983 | 12/2000 |
| WO | WO 2001/009174 | 2/2001 |
| WO | WO 2001/009175 | 2/2001 |
| WO | WO 2001/067865 | 9/2001 |
| WO | WO 2002/063011 | 8/2002 |
| WO | WO 2003/097680 | 11/2003 |
| WO | WO 2004/001012 | 12/2003 |
| WO | WO 2004/054366 | 7/2004 |
| WO | WO 2004/072239 | 8/2004 |
| WO | WO 2004/094630 | 11/2004 |
| WO | WO 2006/066358 | 6/2006 |
| WO | WO 2006/085965 | 8/2006 |
| WO | WO 2007/110686 | 10/2007 |
| WO | WO 2007/137329 | 12/2007 |
| WO | WO 2008/128289 | 10/2008 |
| WO | WO 2009/094719 | 8/2009 |
| WO | WO 2010/015024 | 2/2010 |
| WO | WO 2011/160174 | 12/2011 |

OTHER PUBLICATIONS

Abad et al. (Jul. 21, 2016) "Antifungal Activity of Tobacco Osmotin has Specificity and Involves Plasma Membrane Permeabilization," *Plant Sci.* 118(1):11-23.

Alcouloumre et al. (Dec. 1993) "Fungal Properties of Defensin NP-1 and Activity Against *Crytococcus neoformans* In Vitro," *Antimicrob. Agents Chemothe..* 37( 12) :2628-2632.

Alexander et al. (Aug. 1993) "Increased Tolerance to Two Oomycete Pathogens in Transgenic Tobacco Expressing Pathogenesis-Related Protein 1 a," *Proc. Nat.Acad. Sci. USA* 90:7327-7331.

Almeida et al. (Nov. 15, 2001) "cDNA Cloning and Heterologous Expression of Functional Cysteine-Rich Antifungal Protein Psd1 in the Yeast Pichia pastoris," *Arch. Biochem. Biophys.* 395(2):199-207.

Altschul et al. (1997) "Gapped BLAST and PSI-BLAST: A New Generation of Protein Database Search Programs," *Nucl. Acids. Res.* 25:3389.

(56) References Cited

OTHER PUBLICATIONS

Aluru et al. (Aug. 1999) "Nucleotide Sequence of a Defensin or y-Thionin-Like Gene (Accession No. AF128239) from Habanero Chile," The Electronic Plant Gene Register, Plant. Physiol 120:633-635.
Aluru et al. "Capsicum chinese putative gamma-thionin precursor, mRNA, complete cds", GenBank Nucleotide Accession No. AF128239. 1, Jul. 6, 1999.
Alves et al. (1994) "Expression of Functional Raphanus sativus Antifungal Protein in Yeast," FEBS Lett. 348:228-232.
Anderson et al. (1987) "Immuno-Gold Localization of a-L-arabinofuranosyl Residues in Pollen Tubes of Nicotiana alata Link et Otto," Planta 171 :438-442.
Anderson et al. (May 1989) "Sequence Variability of Three Alleles of the Self-Incompatibility Gene of Nicotiana alata," Plant Cell 1 :483-491.
Atkinson et al. (Feb. 1993) "Proteinase Inhibitors in Nicotiana elate Stigmas are Derived from a Precursor Protein Which is Processed into Five Homologous Inhibitors," Plant. Cell. 5:203-213.
Ausubel et al. (1998) In: Current Protocols in Molecular Biology. *John Wiley & Sons Inc.* 1994-1998.
Balandin et al. (Mar. 1995) "Structure and Induction Pattern of a Novel Proteinase Inhibitor Class II Gene of Tobacco," Plant. Mol Biol. 27(6):1197-1204.
Balandin et al. (May 2005) "A Protective Role for the Embryo Surrounding Region of the Maize Endosperm, as Evidenced by the Characterisation of ZmESR-6, a Defensin Gene Specifically Expressed in this Region," Plant Mol. Biol. 58(2):269-282.
Barta et al. (Dec. 1, 2002) "Repeats with Variations: Accelerated Evolution of the Pin2 Family of Proteinase Inhibitors," Trends Genet. 18(12):600-603.
Bartlett et al. (2002) "The Strobilurin Fungicides," *Pest Manag. Sci.* 58:649-662.
Beck et al. (1993) "Environmental Release Permits," *Bio/Technology* 11 :1524-1528.
Beck von Bodman et al. (Jun. 1995) "Expression of Multiple Eukaryotic Genes from a Single Promoter in Nicotiana," Bio/Technology 13:587-591.
Bednarek et al. (Dec. 1990) "A Carboxyl-Terminal Propeptide is Necessary for Proper Sorting of Barley Lectin to Vacuoles of Tobacco," Plant. Cell 2:1145-1155.
Bednarek et al. (Oct. 1992) "Intracellular Trafficking of Secretory Proteins," Plant Mol. Biol. 20(1):133-150.
Berrocal-Lobo et al. (2002) "Snakin-2, an Antimicrobial Peptide from Potato Whose Gene is Locally Induced by Wounding and Responds to Pathogen Infection," *Plant Physiol.* 128(3):951-961.
Bevan (1984) "Binary Agrobacterium Vectors for Plant Transformation," Nuc. Acids Res. 12(22) :8711-8721.
Bloch et al. (1991) "A New Family of Small (5 kDa) Protein Inhibitors of Insect a-Amylases From Seeds or Sorghum (Sorghum Bicolor (L) Moench) Have Sequence Homologies With Wheat v-Purothionins," *FEBS. Lett.* 279(1):101-104.
Bohlmann, H. (1994) "The Role of Thionins in Plant Protection," Crit. Rev. Plant. Sci. 13(1):1-16.
Bol et al. (1990) "Plant Pathogenesis-Related Proteins Induced by Virus Infection," Ann. Rev. Phytopathol. 28:113-138.
Bonner et al. (1974) "A Film Detection Method for Tritium-Labeled Proteins and Nucleic Acids in Polyacrylamide Gels," *Eur. J. Biochem.* 46:83-88.
Brandstadter et al. (Aug. 1996) "Expression of Genes for a Defensin and a Proteinase Inhibitor in Specific Area of the Shoot Apex and the Developing Flower in Tomato," Mol. Gen. Genet. 252(1-2):146-154.
Broekaert et al. (1990) "An Automated Quantitative Assay for Fungal Growth Inhibition," *FEMS Microbial. Lett.* 69:55-59.
Broekaert et al. (1995) "Plant Defensins: Novel Antimicrobial Peptides as Components of the Host Defense System," Plant Physiol. 108:1353-1358.
Broekaert et al. (1997) "Antimicrobial Peptides from Plants," Crit. Rev. Plant. Sci. 16(3):297-323.

Broekaert et al. (May 1992) "Antimicrobial Peptides from Amaranthus causatus Seeds with Sequence Homology to the Cysteine/Glycine-Rich Domain of Chitin-Binding Proteins," Biochemistry 32(17):4308-4314.
Bryant et al. (Aug. 1976) "Proteinase Inhibitor 11 from Potatoes: Isolation and Characterization of its Protomer Components," Biochemistry 15(16):3418-3424.
Cammue et al. (Feb. 5, 1992) "Isolation and Characterization of a Novel Class of Plant Antimicrobial Peptides from *Mirabilis jalapa* L. Seeds," J. Biol. Chem. 267 ( 4) :2228-2233.
Catanzariti et al. (2005) "An Efficient System for High-Level Expression and Easy Purification of Authentic Recombinant Proteins," *Protein* Science.13:1331-1339.
Cervelli et al. (Nov. 2004) "A Novel C-Terminal Sequence from Barley Poluamine Oxidase is a Vacuolar Sorting Signal," Plant. J. 40(3):410-418.
Chen et al (2006) "A Gateway-Based Platform for Multigene Plant Transformation," Plant. Mol. Biol. 62:927-936.
Chen et al. (2003) "Complete Sequence of the Binary Vector pBI121 and its Application in Cloning T-DNA Insertion from Transgenic Plants," Mol. Breeding 11:287-293.
Chen et al.(Web Release Oct. 30, 2002) "A Novel Defensin Encoded by a Mungbean cDNA Exhibits Insecticidal Activity Against Bruchid," J. Agric. Food Chem. 50(25):7258-7263.
Chiang et al. (1991) "The Fusarium solani-Induced Expression of a Pea Gene Family Encoding High Cysteine Content Proteins," Mol. Plant-Microbe. Interact 4(4):324-331.
Choi et al. (1993) "Nucleotide Sequence of cDNA Encoding a Low Molecular Weight Sulfur-Rich Protein in Soybean Seeds," Plant Physiol. 101 :699.
Choi et al. (1995) "Tissue-Specific and Developmental Regulation of a Gene Encoding a Low Molecular Weight Sulfur-Rich Protein in Soybean Seeds," Mol. Gen. Genet. 246:266-268.
Chrispeels et al. (Feb. 21, 1992) "Short Peptide Domains Target Proteins to Plant Vacuoles," Cell 68:613-616.
Colilla et al. (1990) "y-Purothionins: Amino Acid Sequence of Two Polypeptides of a New Family of Thionins from Wheat Endosperm," FEBS Lett 270(1-2):191-194.
Craik et al. (2004) "Discovery, Sturcture and Biological Activities of the Cyclotides," Curr. Prot. Pept. Sci. 5:297-315.
Craik et al. (Dec. 17, 1999) "Plant Cyclotides: A Unique Family of Cyclic and Knotted Proteins that Defines the Cyclic Cystine Knot Structural Motif," J. Mol. Biol. 294(5):1327-1336.
Craik, D.J. (Dec. 2001) "Plant Cyclotides: Circular, Knotted Peptide Toxins," Toxicon 39(12):1809-1813.
Dasgupta, S., et al., "Co-Ordinated Expression of Multiple Enzymes in Different Subcellular Compartments in Plants", Plant Journal, Oct. 1, 1998, p. 107-116, vol. 16, No. 1, Blackwell Scientific Publications, Oxford, GB.
Database Geneseq [Online] "Plan defensin NeThio2 mature domain," (Apr. 22, 2004), Database accession No. GSP ADI56858.
Database UniProt [Online], Dec. 7, 2004, Database Accession No. Q5U523, Xenopus laevis, Neuritin-B (nrn1-B).
Database UniProt [Online], May 1, 1999, Database Accession No. Q9ZCC6, Rickettsia prowezekii, from genome sequence and origin of mitochondria, cytidine and deoxycytidylate deaminase family, submitted by Andersson, et al.
Database UniProt [Online], Oct. 1, 2000, Database Accession No. Q9M344, *Arabidopsis thaliana*, from complete proteome.
Davis et al. (Mar. 1998) "Soluble, Highly Fluorescent Variants of Green Fluorescent Protein (GFP) for Use in Higher Plants," Plant Mol. Biol. 36(4):521-528.
De Samblanx et al. (Jan. 10, 1997) "Mutational Analysis of a Plant Defensin from Radish (*Raphanus sativus* L.) Reveals Two Adjacent Sites Important for Antifungal Activity," *J. Biol. Chem.* 272(2):1171-1179.
De Vos et al. (Mar. 1985) "Three-Dimensional Structure of Thaumatin I, an Intensely Sweet Protein," *Proc. Nat. Acad. Sci. USA* 82:1406-1409.
Del Sorbo et al. (2000) "Fungal Transporters Involved in Efflux of Natural Toxic Compounds and Fungicides," *Fungal Genet. Biol.* 30:1-15.

(56) References Cited

OTHER PUBLICATIONS

Deleo et al. (2002) "PLANT-Pis: A Database for Plant Protease Inhibitors and their Genes," Nuc. Acids Res. 30(1):347-348.
Deloose et al. (1988) "Primary Structure of a Hormonally Regulated β-Glucanase of Nicotiana plumbaginifolia," Gene 70:13-23.
Damon et al. (Oct. 1990) "Nucleotide Sequence of Two Anther-Specific cDNAs from Sunflower (*Helianthus annuus* L.)," Plant Mol. Biol. 15(4):643-646.
Dong et al. (2005) "Interactin Proteins and Differences in Nuclear Transport Reveal Specific Functions for the NAP1 Family Proteins in Plants," *Plant Physiol.* 138:1446-1456.
Dow AgroSciences, Laredo and PropiMax Fungicide information Sheet, 2007.
Drews et al. (Jun. 1991) "Negative Regulation of the *Arabidopsis* Homeotic Gene AGAMOUS by the APETALA2 Product," Cell 65:991-1002.
Ebert et al. (1990) *Plant Mol. Biol.* 14:815-824.
Ekengren et al. (Nov. 1999) "*Drosophila* cacropin as an Antifungal Agent," *Insect Biochem. Mot. Biol.* 29(11):965-972.
Epand et al. (2006) Role of Membrane Lipids in the Mechanism of Bacterial Species Selective Toxicity by Two α/β-Peptides *Biochim. Biophys. Acta* 1758: 1343-1350.
Epple et al. (1997) "ESTs Reveal a Multigene Family for Plant Defensins in *Arabidopsis thaliana*," FEBS Lett. 400:168-172.
Extended European Search Report, Appl. No. 07718958.7, dated Jan. 5, 2010, pp. 17.
Extended Search Report for EP 12744866.0 dated Dec. 18, 2014.
Fant et al. (1994) "The Solution Structure by 1 H NMR of a Plant Antifungal Protein from Radish Seeds (Rs-AFP1)," In: Ingman et al eds., Abstracts of the 12$^{th}$ European Experimental NMR Conference, p. 247.
Fedorova et al. (Oct. 2002) "Genome-Wide Identification of Nodule-Specific Transcripts in the Model Legume Medicago truncatula," Plant. Physiol.130:519-537.
Florack et al. (Jan. 1994) "Expression of Biologically Active Hordothionins in Tobacco. Effects of Pre- and Pro-Sequences at the Amino and Carboxyl Termini of the Hordothionin Precursor on Mature Protein Expression and Sorting," Plant. Mol. Biol. 24(1):83-96.
Florack et al. (Oct. 1994) "Thionins: Properties, Possible Biological Roles and Mechanisms of Action," Plant. Mol. Biol. 26(1):25-37.
Frame et al. (2002) "*Agrobacterium tumefaciens*-Mediated Transformation of Maize Embryos Using a Standard Binary Vector System," *Plant Physiology.* 129:13-22.
Francois et al. (2004) "Processing in *Arabidopsis thaliana* of a Heterologous Polyprotein Resulting in Differential Targeting of the Individual Plant Defensins," *Plant Science.* 166: 113-121.
Francois et al. (Apr. 2002) "Transgenic Expression in *Arabidopsis* of a Polyprotein Construct Leading to Production of Two Different Antimicrobial Proteins," Plant Physiol. 128:1346-1358.
Frigerio et al. (2001) "The C-Terminal Tetrapeptide of Phaseolin is Sufficient to Target Green Fluorescent Protein to the Vacuole," J. Plant. Physiol. 158:499-503.
Gao et al. (2000) "Fungal Pathogen Protection in Potato by Expression of a Plant Defensin Peptide," *Nat. Biotechnol.* 18(12):1307-1310.
Genbank Accession No. U20591, "Solanum Lycopersicum Flower Specific Gamma-Thionin-Like Protein/Acidic Protein Precursor, mRNA, Complete eds," Milligan et al. (Nov. 4, 1995).
Gorlach et al. (Apr. 1996) "Benzothiadiazole, a Novel Class of Inducers of Systemic Acquired Resistance, Activates Gene Expression and Disease in Wheat," Plant Cell 8:629-643.
Graham et al. (Jul. 2004) "Computational Identification and Characterization of Novel Genes from Legumes," *Plant Physiol.* 135:1179-1197.
Graham et al. (Jun. 10, 1985) "Wound-Induced Proteinase Inhibitors from Tomato Leaves," J. Biol. Chem. 260(11):6561-6564.
Greco et al. (1995) "The Search for Synergy: a Critical Review from a Response Surface Perspective," *Pharmacol. Rev.* 47:331-385.

Gu et al. "A Flower-Specific cDNA Encoding a Novel Thionin in Tobacco," *Mo/. Gen. Genet.* 1992, 234:89-96, Springer-Verlag.
Gustafson et al. (Oct. 1994) "Circuline A and B. Novel Juman Immunodeficiency Virus (HIV)-Inhibitory Macrocyclic Peptide from the Tropical Tree Chassalia parvifolia," J. Am. Chem. Soc. 116(20):9337-9338.
Halcygen Pharmaceuticals Press Release, Jul. 5, 2007, "Halcyge n Anti-Fungal Drug Passes Clinical Test—To Enter Phase III Trial in 2007/2008."
Hall et al. (1999) "BioEdit: A User-Friendly Biological Sequence Alignment Editor and Analysis Program for Windows 95/98/NT," Nuc. Acids Symp. 41:95-98.
Halpin et al. (Feb. 1999) "Self-Processing 2A-Polyproteins—A System for Co-Ordinate Expression of Multiple Proteins in Transgenic Plants," Plant. J. 17(4):453-459.
Hass et al. (Feb. 1982) "Primary Structures of Two Low Molecular Weight Proteinase Inhibitors from Potatoes," Biochemistry 21 (4):752-756.
Heath et al. (1997) "Proteinase Inhibitors from Nicotiana alata Enhance Plant Resistance to Insect Pests," J. Insect Physiol 43(9):833-842.
Heath et al. (May 1995) "Characterization of the Protease Processing Sites in a Multidomain Proteinase Inhibitor Precursor from Nicotiana alata," Eur. J. Biochem. 230(1):250-257.
Himly et al. (Web release Nov. 15, 2003) "Art v 1, The Major Allergen of Mugwort Pollen, is a Modular Glycoprotein with a Defensin-Like and a Hydroxyproline-Rich Domain," FASEB J. 17:106-108.
Holwerda et al. (Mar. 1992) "Proaleurain Vacuolar Targeting is Mediated by Short Continuous Peptide Interactions," Plant Cell 4:307-318.
International Preliminary Examination Report for corresponding WO application, PCT/AU2007/000712, completed Mar. 27, 2008, 6 pages.
International Preliminary Report on Patentability corresponding to International Application No. PCT/AU2012/000112, completed Aug. 21, 2012.
International Preliminary Report on Patentability, Corresponding to International Application No. PCT/AU2008/000550, Completed Jun. 10, 2008.
International Preliminary Report on Patentability, for corresponding Wo application No. PCT/AU2009/000106, completed Feb. 20, 2009.
International Search Report and Written Opinion corresponding to International Application No. PCT/AU2007/000712, dated Jun. 13, 2008.
International Search Report and Written Opinion, Corresponding to International Application No. PCT/AU2009/000106, dated Mar. 20, 2009.
International Search Report with Written Opinion corresponding to International Application No. PCT/AU2012/000112, dated Mar. 29, 2012.
International Search Report, Corresponding to International Application No. PCT/AU2008/000550, dated Jun. 26, 2008.
Ishibashi et al. (1990) "Stored mRNA in Cotyledons of Vigna unguiculata Seeds: Nucleotide Sequence of Cloned cDNA for a Stored mRNA and Induction of its Synthesis by Precocious Germination," Plant. Mol. Biol. 15:59-64.
Janssen et al. (2003) "Structure of *Petunia hybrida* Defensin 1, a Novel Plant Defensin with Five Disulfide Bonds," Biochemistry 42(27):8214-8222.
Jennings et al. (Sep. 11, 2001) "Biosynthesis and Insecticidal Properties of Plant Cyclotides: The Cyclic Knotted Proteins from Oldenlandia affinis," Proc. Nat. Acad. Sci. USA 98(19):10614-10619.
Jha et al.(2009) "Expression of Dm-AMP1 in rice confers resistance to *Magnaporthe oryzae* and *Rhizoctonia solani,*" *Transgenic Res.* 18(1):59-69.
Johnson et al. (2005) "Maturation of the Floral Defensin of *Nicotiana alata*," ASPB/ComBio 2005, Adelaide, Sep. 25-29, 2005 (Joint meeting).

(56) References Cited

OTHER PUBLICATIONS

Johnson et al. (2006) "The C-Terminal Propeptide Governs Vacuolar Deposition of the *Nicotiana alata* Floral Defensin" Lorne 2006, Feb. 5-9, 2006.
Jones et al. (2006) "The Plant Immune System," *Nature.* 444:323-329.
Kader, J.C. (1997) "Lipid-Transfer Proteins in Plants," Ann. Rev. Plant Physiol. Plant Mol. Biol. 47:627-654.
Kader J.C.(Feb. 1997) "Lipid-Transfer Proteins: A Puzzling Family of Plant Proteins," Trends Plant Sci. 2(2):66-70.
Karunanadaa et al. (1994) "Characterization of a Predominantly Pistil-Expressed Gene Encoding a g-Thionin-Like Protein of Petunia inflate," Plant Mol. Biol. 26:459-464.
Keil et al. (1986) "Primary Structure of a Proteinase Inhibitor II Gene from Potato (*Solanum tuberosum*)," Nuc. Acids Res. 14(14):5641-5650.
Khan et al. (2006) "Transgenic Potatoes Expressing Wasabi Defensin Peptide Confer Partial Resistance to Gray Mold (*Botrytis cinerea*)," Plant. Biotechnol. 23:179-183.
Kim et al. (Aug. 2001) "Internalization of Tenecin 3 by a Fungal Cellular Process is D110 Essential for its Fungicidal Effect on *Candida albicans,*" Eur. J. Biochem. 268( 16) :4449-4458.
Klis et al. (2002) "Dynamics of Cell Wall Structure in *Saccharomyces cerevisiae,*" FEMS Microbial. Rev. 26:239-256.
Komori et al. (1999) NCBI Accession No. BAA21325.1, Nicotiana paniculata Gamma-Thionin.
Komori et al. (Dec. 15, 1998) "Gamma-Thionin 1 Precursor," EMBL Accession No. 024115.
Kragh et al. (1995) "Characterization and Localization of New Antifungal Cystein-Rich Proteins from Beta vilgaris," Mol. Plant-Microbe Interact. 8(3):424-434.
Kristensen et al. (Aug. 1999) "Processing, Disulfide Pattern, and Biological Activity of a Sugar Beet Defensin, AX2, Expressed in Pichia pastoris," Prot. Expr. Purif. 16(3):377-387.
Kushmerick et al. (1998) "Functional and Structural Features of y-Zeathionins, A New Class of Sodium Channel Blockers," FEBS Lett. 440:302-306.
Ladokhin et al.(2001) "Detergent-Like Permeabilization of Anionic Lipid Vesicles by Melittin," *Biophys.Biochim. Acta* 1514:253-260.
Ladokhin et al. (Apr. 1997) "Sizing Membrane Pores in Lipid Vesicles by Leakage of Co-Encapsulated Markers: Pore Formation by Melittin," *Biophys. J.* 72:1762-1766.
Lay et al. (1997) "Isolation and Characterization of a Flower Specific Definsin-Like Protein from the Flowers of *Nicotiana alata*," ASBMB Conference, Melbourne, Austrailia.
Lay et al. (1998) "Characterization of an Antifungal Defensin Protein from Nicotiana alata," ASBMB Conference, Adelaide, Australia.
Lay et al. (1998) "Temporal and Spatial Characterization of a Predominantly Flower Specific Defensin-Like Protein from Nicotiana alata," LORNE Conference, Melbourne, Australia.
Lay et al. (1999) "A Tail of a Floral Defensin from Nicotiana alata," COMBIO Conference, Goldcoast, Australia.
Lay et al. (2000) "Structural Characterization of a Flower-Specific Defensin," LORNE Conference, Melbourne, Australia.
Lay et al. (2000) "Structure and Function of a Floral Defensin From Nicotiana alata," COM BIO Conference, New Zealand.
Lay et al. (2000) "Structure and Function of a Floral Defensin From Nicotiana alata," FAOBMB Conference, Beijing, China.
Lay et al. (2003) "The Three-Dimensional Solution Structure of NaD1, a New Floral Defensin from *Nicotiana alata* and its Application to a Homology Model of the Crop Defense Protein alfAFP," J Mol Biol 325:175-188.
Lay et al. (2005) "Defensins—Components of the Innate Immune System in Plants," Curr. Prat. Pept. Sci. 6:85-101.
Lay et al. (Mar. 2003) "Isolation and Properties of Floral Defensins from Ornamental Tobacco and Petunia," *Plant Physiol.* 131 :1283-1293.
Lee et al.(1999) "A Novel Two-Chain Proteinase Inhibitor Generated by Circularization of a Multidomain Precursor Protein," *Nature Structural Biology.* 6(6) :526-530.
Leiter et al. (Jun. 2005) "Antifungal Protein PAF Severely Affects the Integrity of the Plasma Membrane of *Aspergillus nidulans* and Induces an Apoptosis-Like Phenotype," *Antimicrob. Agents Chemother.* 49(6):2445-2453.
Li and Gray (Aug./Jul. 30, 1999) "N. tabacum mRNA for defensin," GenBank Accession No. X99403.
Li et al. (2004) "Use of Scots Pine Seedling Roots as an Experimental Model to Investigate Gene Expression During Interaction with the Conifer Pathogen Heterobasidion Annosum (P-type)," *J. Plant Res.* 117(2):155-162.
Lin et al. (2003) "Efficient Linking and Transfer of Multiple Genes by a Multigene Assembly and Transformation Vector System", Proceedings of the National Academy of Sciences of USA, May 13, 2003, p. 5962-5967, vol. 100, No. 10, National Academy of Science, Washington, DC, US.
Lin et al. (2007) "Structure-Based Protein Engineering for a-amylase Inhibitory Activity of Plant Defensin," Proteins 68(2):530-540 in 139-08 C.
Liu et al. (Feb. 15, 1995) "The Pro Region of Human Neutrophil Defensin Contains a Motif that is Essential for Normal Subcellular Sorting," Blood 85(4):1095-1103.
Lobo et al.(Jan. 6, 2007) "Antifungal Pisum sativum Defensin 1 Interacts with *Neurospora crassa* Cyclin F Related to the Cell Cycle," Biochemistry46(4):987-996.
Lou et al. "Nitrogen Supply Influences Herbivore-Induced Direct and Indirect Defenses and Transcriptional Responses in *Nicotiana attenuata,*" Plant Physiol. 135:496-506, May 2004, American Society of Plant Biologists.
Lowenberger et al. (1999) "Insect Immunity: Molecular Cloning, Expression, and Characterization of cDNA and Genomic DNA Encoding Three Isoforms of Insect Defensin in Aedes aegypti," Insect. Mol. Biol. 8(1):107-118.
Marcos et al. (Feb. 1994) "In Vitro Characterization of a Cassette to Accumulate Multiple Proteins Through Synthesis of a Self-Processing Polypeptide," Plant Mol. Biol. 24(3):495-503.
Marcus et al. (1997) "Purification, Characterization and cDNA Cloning of an Antimicrobial Peptide from Macadamia integrifolia," Eur. J. Biochem. 244:743-749.
Marmur et al. (1962) "Determination of the Base Composition of Deoxyribonucleic Acid From Its Thermal Denaturation Temperature," *J. Mo/. Biol.* 5:109-118.
Marton et al. (Nov. 2010) "Nontransqenic Genome Modification in Plant Cells," Plant Physiology 154:1079-1087.
Maruyama et al. (May 2006) "Multiple Vacuolar Sorting Determinants Exist in Soybean 11 S Globulin," Plant Cell 18:1253-1273.
Matsuoka et al. (Feb. 1991) "Propeptide of a Precursor to a Plant Vacuolar Protein Required for Vacuolar Targeting," Proc. Nat. Acad. Sci. USA.
Matsuzaki (1999) "Why and How are Peptide-Lipid Interactions Utilized for Self-Defense? Magainins and Tachyplesins as Archetypes," *Biochem. Biophys. Acta* 1462:1-10.
Matsuzaki et al. (1995) "Molecular Basis of Membrane Selectivity of an Antimicrobial Peptide, Magainin 2," *Biochemistry* 34(10):3423-3429.
Matzke et al. (Apr. 1998) "Position Effects and Epigenetic Silencing of Plant Transgenes," Curr. Opin. Plant Biol. 1 (2):142-148.
Mckenna et al. (2004) "The Potential of the Antifungal Protein NaD1 for Control of Fusarium Wilt and Verticillium Wilt," 12th Australian Cotton Conference, Aug. 10-12, 2004, 1 page.
McManus et al. (Oct. 29, 1999) "MiAmp1, a Novel Protein from Macadamia integrifolia Adopts a Greek Key β-Barrel Fold Unique Amongst Plant Antimicrobial Proteins," J. Mol. Biol. 293(3):629-638.
Melchers et al. (Feb. 1993) "Extracellular Targeting of the Vacuolar Tobacco Proteins AP24, Chitinase and β-1, 3-Glucanese in Transgenic Plants," Plant. Mol. Biol. 21 (4):583-593.
Melo et al. (Aug. 1, 2002) "Inhibition of Trypsin by Cowpea Thionin: Characterization, Molecular Modeling, and Docking," Proteins 48(2):311-319.

(56) References Cited

OTHER PUBLICATIONS

Mendez et al. (1990) "Primary Structure and Inhibition of Protein Synthesis in eukaryotic Cell-free System of a Novel Thionin, g-hordothionin, from Barley Endosperm," Eur. J. Biochem. 194:533-539.
Mendez et al. (1996) "Primary Structure of w-Hordothionin, a Member of a Novel Family of Thionins from Barley Endosperm, and its Inhibition of Protein Synthesis in Eukaryotic and Prokaryotic Cell-Free Systems," Eur. J. Biochem.239:67-73.
Mergaert et al. (May 2003) "A Novel Family in Medicago truncatula Consisting of More Than 300 Nodule-Specific Genes Coding for Small Secreted Polypeptides with Conserved Cysteine Motifs," Plant. Physiol. 132:161-173.
Metlen et al. (2009) "Plant Behavioural Ecology: Dynamic Plasticity in Secondary Metabolites," *Plant Cell Environ.* 32(6):641-653.
Meyer et al. (1996) "Fruit-Specific Expression of a Defensin-Type Gene Family in Bell Pepper" *Plant Physiol.* 112:615-622.
Michaelson et al. (Jun. 1992) "Cationic Defensins Arise from Charge-Neutralized Properties : A Mechanism for Avoiding Leukocyte Autotoxicity," J. Leucoc. Biol. 51 :634-639.
Miller et al. (2000) GenBank Accession No. AF105340, "Nicotiana alata Proteinase Inhibitor Precursor, mRNA, Complete cds,".
Miller et al. (Aug. 1999) "Identification and Characterization of a Prevacuolar Compartment in Stigmas of Nicotiana alata," Plant Cell 11 :1499-1508.
Miller et al.(Jan. 2000) "Identification of a Novel Four-Domain Member of the Proteinase Inhibitor II Family from the Stigmas of Nicotinia alata," Plant Mol. Biol. 42(2) :329-333.
Milligan et al. (1995) "Nature and Regulation of Pistil-Expressed Genes in Tomato," Plant Mol. Biol. 28:691-711.
Mirouze et al. (Aug. 2006) "A Putative Novel Role for Plant Defensins: A Defensin from the Zinc Hyper-Accumulating Plant, *Arabidopsis halleri*, Confers Zinc Tolerance," Plant. J. 47(3):329-342.
Moreno et al. (1994) "Pseudothionin-St1, a Potato Peptide Active Against Potato Pathogens," Eur. J. Biochem. 223:135-139.
Neuhaus et al. (Nov. 15, 1991) "A Short C-Terminal Sequence is Necessary and D164 Sufficient for the Targeting of Chitinases to the Plant Vacuole," Proc. Nat. Acad. Sci. USA 88(22): 10362-10366.
Neuhaus, J.M. (1996) "Protein Targeting to the Plant Vacuole," Plant Physiol. Biochem. 34(2):217-221.
Neumann et al. (1996) "Purification and Mass Spectrometry-based Sequencing of Yellow Mustard (*Sinapis alba* L.) 6 kDa Proteins," Int. J. Pept. Prot. Res.47:437-446.
Nielsen et al. (1994) "The Three-Dimensional Solution Structure by 1 H NMR of a 6-kDa Proteinase Inhibitor Isolated from the Stigma of Nicotiana alata," J Mol Biol 242:231-243.
Nielsen et al. (1995) "Structures of a Series of 6-kDa Trypsin Inhibitors Isolated from the Stigma of Nicotiana alata," Biochemistry 34:14304-14311.
Nielsen et al. (1996) "Synthesis and Structure Determination by NMR of a Putative Vacuolar Targeting Peptide and Model of a Proteinase Inhibitor from Nicotiana alata," Biochemistry 35(2):369-378.
Nilsson et al. (Aug. 25, 1989) "Short Cytoplasmic Sequences Serve as Retention Signals for Transmembrane Proteins in the Endoplasmic Reticulum," *Cell* 58:707-718.
Nishizawa et al. (Jun. 2003) "AC-Terminal Sequence of Soybean β-Conglycinin a' Subunit Acts as a Vacuolar Sorting Determinant in Seed Cells," Plant. J. 34(5):647-659.
Nitti et al. (1995) "Amino Acid Sequence and Disulphide-Bridge Pattern of Three g-Thionins from SorQhum bicolor," Eur. J. Biochem. 228:250-256.
Notice of Allowance, dated Jul. 5, 2012, for U.S. Appl. No. 12/708,421, an application with related subject matter, 4 pp.
Nurnberger et al. (2004) "Innate Immunity in Plants and Animals: Striking Similarities and Obvious Differences," *Immunol. Rev.* 198:249-266.

Oberparleiter et al. (Nov. 2003) "Active Internalization of the *Penicillium chrvsogenum* AntifunQal Protein PAF in Sensitive AsperQilli," *Antimicrob. Agents Chemother.* 47(11):3598-3601.
Office Action corresponding to U.S. Appl. No. 10/072,809, dated Mar. 11, 2004.
Office Action corresponding to U.S. Appl. No. 11/062,999, dated Oct. 2, 2006.
Office Action corresponding to U.S. Appl. No. 11/372,761, dated Dec. 28, 2007.
Office Action corresponding to U.S. Appl. No. 11/372,761, dated Jun. 16, 2008.
Office Action corresponding to U.S. Appl. No. 11/372,771, dated Apr. 27, 2009.
Office Action corresponding to U.S. Appl. No. 11/372,771, dated Dec. 28, 2007.
Office Action corresponding to U.S. Appl. No. 11/372,771, dated Sep. 25, 2008.
Office Action corresponding to U.S. Appl. No. 11/753,072, dated Aug. 10, 2011.
Office Action corresponding to U.S. Appl. No. 11/753,072, dated Aug. 15, 2013.
Office Action corresponding to U.S. Appl. No. 11/753,072, dated Jan. 19, 2011.
Office Action corresponding to U.S. Appl. No. 12/105,956, dated Nov. 24, 2010.
Office Action corresponding to U.S. Appl. No. 12/105,956, dated Oct. 13, 2011.
Office Action corresponding to U.S. Appl. No. 12/362,657, dated Aug. 19, 2011.
Office Action corresponding to U.S. Appl. No. 12/362,657, dated Jan. 30, 2012.
Office Action corresponding to U.S. Appl. No. 12/362,657, dated Sep. 13, 2012.
Office Action corresponding to U.S. Appl. No. 12/535,443, dated Feb. 4, 2013.
Office Action corresponding to U.S. Appl. No. 12/535,443, dated May 23, 2012.
Office Action corresponding to U.S. Appl. No. 12/535,443, dated Sep. 12, 2013.
Office Action corresponding to U.S. Appl. No. 12/535,443, dated Sep. 6, 2011.
Office Action corresponding to U.S. Appl. No. 12/708,421, dated Jan. 13, 2011.
Office Action corresponding to U.S. Appl. No. 12/708,421, dated Jul. 26, 2011.
Office Action corresponding to U.S. Appl. No. 12/708,421, dated Jun. 4, 2012.
Office Action corresponding to U.S. Appl. No. 13/596,838, dated Apr. 12, 2013.
Ohtani et al. (1977) "Complete Primary Structures of Two Subunits of Purothionin A, A Lethal Protein for Brewer's Yeast from Wheat Flour," J. Biochem. 82(3):753-7657.
Osborn et al. (1995) "Isolation and Characterization of Plant Defensins from Seeds of Asteraceae, Fabaceae, Hippocastanaceae and Saxifragaceae," FEBS Lett. 368:257-262.
Osborn et al. (1999) Seed Proteins, Shewry et al. Eds., Kluwer Academic Publishers, Dordrecht, pp. 727-751.
Ozaki et al. (1980) "Amino Acid Sequence of a Purothionin Homolog from Barley Flour," J. Biochem. 87(2):549-555.
Park et al. (2002) "Characterization of a Stamen-Specific cDNA Encoding a Novel Plant Defensin in Chinese Cabbage," Plant Molecular Biology 50:59-69.
Patel et al. (Web Release Jan. 6, 1998) "Structural Studies of Impatiens balsamina Antimicrobial Protein (IB-AMP1 )," Biochemistry 37(4):983-990.
Pearce et al. (1993) "Purification and Characterization from Tobacco (*Nicotiana tabacum*) Leaves of Six Small, Wound-Inducible, Proteinase Isoinhibitors of the Potato Inhibitor 11 Family," Plant Physiol. 102:639-644.
Pelegrini et al. (2005) "Plant y-Thionins: Novel Insights on the Mechanism of Action of a Multi-Functional Class of Defense Proteins," *Int. J. Biochem. Cell Biol.* 37:2239-2253.

(56) References Cited

OTHER PUBLICATIONS

Plunkett et al.(Feb. 1982) "Proteinase Inhibitors I and II from Leaves of Wounded Tomato Plants: Purification and Properties," Arch. Biochem. Biophys. 213(2):463-472.
Ponstein et al. (1994) "A Novel Pathogen and Wound Inducible Tobacco (Nicotiana tabacum) Protein with Antifungal Activity," Plant Physiol. 104:109-118.
Potter et al. (1993) "Regulation of a Hevein-Like Gene in Arabidopsis," Mol/. Plant Microbe. Interact. 6:680-685.
Raikhel et al. (Oct. 1987) "Isolation and Characterization of a cDNA Clone Encoding Wheat Germ Agglutinin," Proc. Nat. Acad. Sci. USA 84(19):6745-6749.
Ramamoorthy et al. (Jun. 2007) "Two Mitogen-Activated Protein Kinase Signaling Cascades Mediate Basal Resistance to Antifungal Plant Defensins in Fusarium Qraminearum," Cell Microbial. 9(6):1491-1506.
Ramamoorthy et al. (Nov. 2007) "Glucosylceramide Synthase is Essential for Alfalfa Defensin-Mediated Growth Inhibition but not for Pathogenicity of Fusarium graminearum," Mo/. Microbial. 66(3):771-786.
Reimann et al. (Jn.2005) "Inhibition of Efflux Transporter-Mediated Fungicide Resistance in Pyrenophora tritici-repentis by a Derivative of 4'-Hydroxyflavone and Enhancement of Fungacide Activity," Appl. Environ. Microbial. 71 (6):3269-3275.
Richardson, M. (Aug. 1979) "The Complete Amino Acid Sequence and the Trypsin Reactive (Inhibitory) Site of the Major Proteinase Inhibitor from the Fruits of Aubergine (Solanum melongena L.)," FEBS Lett. 104(2):322-326.
Richer (1987) "Synergism—A Patent View," Pest. Sci. 19:309-315.
Robinson et al. (2005) "Protein Sorting to the Storage Vacuoles of Plants: A Critical Appraisal," Traffic 6:615-625.
Rogers et al. (1998) "Gene Transfer in Plants: Production of Transformed Plants Using Ti Plasmid Vectors," Methods for Plant Mo/. Blol. :423-436.
Romero et al. (1997) "Processing of Thionin Precursors in Barley Leaves by a Vacuolar Proteinase," Eur. J. Biochem. 243:202-208.
Ryals et al. (1996) "Systemic Acquired Resistance," The Plant Cell 8:1809-1819.
Saalbach et al. (1996) "The Vacuolar Targeting Signal of the 2S Albumin from Brazil Not Resides at the C Terminus and Involves the C-Terminal Propeptide as an Essential Element," Plant Physiol. 112:975-985.
Saint-Jore-Dupas et al. (2005) "Targeting of ProConA to the Plant Vacuole D221 Depends on its Nine Amino-Acid C-Terminal Propeptide," Plant Cell Physiol. 46(10):1603-1612.
Saitoh et al. (2001) "Production of Antimicrobial Defensin in Nicotiana benthamiana with a Potato Virus X Vector," Mol. Plant-Microbe Interact. 14(2):111-115.
Salzman et al. (2004) "Inorganic Cations Mediate Plant PR5 Protein Antifungal Activity Through Fungal Mnn1- and Mnn4-Regulated Cell Surface Glycans," Mo/.69 Plant Microbe Interact. 17(0):780-788.
Sanchez-Serrano et al. (Apr. 1986) "Nucleotide Sequence of Proteinase Inhibitor II Encoding cDNA of Potato (Solanum tuberosum) and its Mode of Expression," Mol. Gen. Genet. 203(1):15-20.
Scanlon et al (1999) "Structure of a Putative Ancestral Protein Encoded by a Single Sequence Repeat from a Multidomain Proteinase Inhibitor Gene from Nicotiana Alata", Structure, Jul. 15, 1999, p. 793-802, vol. 7, No. 7, Current Biology Ltd., Philadelphia, PA, US.
Schaaper et al. (2001) "Synthetic Peptides Derived from the Beta2-Beta3 Loop of Raphanus Sativus Antifungal Protein 2 that Mimic the Active Site," J. Pept. Res.57(5) :409-418.
Schirra et al. (2001) "The Solution Structure of C1-T1, a Two-Domain Proteinase Inhibitor Derived from a Circular Precursor Protein from Nicotiana alata," J Mol Biol 306:69-79.
Schultz et al. (1997) "Molecular Characterization of a cDNA Sequence Encoding the Backbone of a Style-Specific 120 kDa Glycoprotein Which has Features of Both Extensins and Arabinogalactan Proteins," Plant. Mol. Biol. 35:833-845.

Segura et al. (1998) "Novel Defensin Subfamily from Spinach (Spinacia oleracea)," FEBS Lett. 435:159-162.
Sharma et al. (Jun. 1996) "Isolation and Characterization of a cDNA Encoding a Plant Defensin-Like Protein from Roots of Norway Spruce," Plant. Mol. Biol. 31(3):707-712.
Shewry et al. (1997) "Plant Proteins that Confer Resistance to Pests and Pathogens," Adv. Bot. Res. 26:135-192.
Shinshi et al. (Mar. 1990) "Structure of a Tobacco Endochitinase Gene: Evidence that Different Chitinase Genes can Arise by Transportation of Sequences Encoding a Cysteine-Rich Domain," Plant Mol. Biol. 14(3):357-368.
Silverstein et al. (Jun. 2005) "Genome Organization of More Than 300 Defensin-Like Genes in Arabidopsis," Plant Physiol. 138:600-610.
Sjahrill et al. (2006) "Transgenic Phalaenopsis Plants with Resistance to Erwinia carotovora Produced by Introducing Wasabi Defensin Gene Using Agrobacterium Method," Plant Biotechnol. 23:191-194.
Sotchenkov et al. (2005) "Modification of the Sunflower Defensin SD2 Gene Sequence and Its Expression in Bacterial and Yeast Cells," Russian Journal of Genetics. 41 :1194-1201.
Spelbrink et al. (2004) "Differential Antifungal and Calcium Channel-Blocking Activity among Structurally Related Plant Defensins," Plant Physiol. 135(4):2055-2067.
Stiekema et al. (1988) "Molecular Cloning and Analysis of Four Potato Tuber mRNAs," Plant Mol. Biol. 11:255-269.
Stotz et al. (2009) "Plant Defensins: Defense, Development and Application," Plant Signaling & Behavior 4(11):1010-1012.
Supplementary European Search Report for EP 08733377, (which is a European patent application which corresponds to the present application), dated May 26, 2010, 9 pp.
Tailor et al. (Sep. 26, 1997) "A Novel Family of Small Cysteine-Rich Antimicrobial Peptides from Seed of Impatiens balsamina is Derived from a Single Precursor Protein," J. Biol. Chem. 272(39):24480-24487.
Takemoto et al. (May 17, 2000) "Thionin Like Protein [Nicotiana tabacum[," GenBank Accession No. BAA95697.
Tam et al. (Aug. 3, 1999) "An Unusual Structural Motif of Antimicrobial Peptides Containing End-To-End Macrocycle and Cystine-Knot Disulfides," Proc. Nat. Acad. Sci. USA 96(16):8913-8918.
Tamura et al. (2007) "MEGA4: Molecular Evolutionary Genetics Analysis (MEGA) Software Version 4.0," Mol. Biol. Evol. 24:1596-1599.
Taylor et al. (Dec. 1993) "Induction of a Protease Inhibitor II-Class Gene by Auxin in Tomato Roots," Plant Mol. Biol. 23(5):1005-1014.
Terras et al. (Aug. 1992) "Analysis of Two Novel Classes of Plant Antifungal Proteins from Radish (Raphanus sativus L.) Seeds," J. Biol. Chem. 267(22):15301-15309.
Terras et al. (Feb. 1993) "A New Family of Basic Cysteine-Rich Plant Antifungal Proteins From Brassicaceae Species," FEBS Lett. 316(3):233-240.
Terras et al. (May 1995) "Small Cysteine-Rich Antifungal Proteins from Radish: their Role in Host Defense," Plant Cell 7:573-588.
Theis et al. (2004) "Antifungal Proteins: Targets, Mechanisms and Prospective Applications," Cell Mol. Life Sci. 61 :437-455.
Theis et al. (Feb. 2003) "The Antifungal Protein from Aspergillus giganteus Causes Membrane Permeabilization," Antimicrob. Agents Chemother. 47(2):588-593.
Thevissen et al. (2000) "Specific Binding Sites for an Antifungal Plant Defensin from D250 Dahlia (Dahlia merckit) on Fungal Cells are Required for Antifungal Activity," Mol. Plant. Microbe. Interact. 13(1):54-61.
Thevissen et al. (2005) "Fungal Sphingolipids as Targets for the Development of Selective Antifungal Therapeutics," Curr. Drug Targets 6:923-928.
Thevissen et al. (Aug. 15, 2000) "A Gene Encoding a Shingolipid Biosynthesis Enzyme Determines the Sensitivity of Saccharomyces cerevisiae to an Antifungal Plant Defensin from Dahlia (Dahlia merckit)," Proc. Nat. Acad. Sci. USA 97(17):9531-9536.
Thevissen et al. (Feb. 6, 2004) "Defensins from Insects and Plants Interact with Fungal Glucosylceramides," J. Biol. Chem. 279(6):3900-3905.

(56) References Cited

OTHER PUBLICATIONS

Thevissen et al. (Web Release Aug. 22, 2003) "DmAMP1, An Antifungal Plant Defensin from Dahlia (*Dahlia merckii*), Interacts with Sphingolipids from *Saccharomyces cerevisiae*," FEBS Microbial. Lett. 226:169-173.
Thomma et al. (2002) "Plant Defensins", Planta, Dec. 1, 2002, p. 193-202, vol. 216, No. 2, Springer Verlag, DE.
Thomma et al. (2003) "Mode of Action of Plant Defensins Suggest Therapeutic Potential," Curr. Drug Targets Infect. Dis. 3:1-8.
Thomma et al. (Dec. 8, 1998) "Separate Jasmonate-Dependent and Salicylate-Dependent Defense-Response Pathways in *Arabidopsis* are Essential for Resistance to Distinct Microbial Pathogens," Proc. Nat. Acad. Sci. USA 95(25):15107-15111.
Thomma et al. (Jul. 1998) "Tissue-Specific Expression of Plant Defensin Genes PDF2.1 and PDF2.2 in *Arabidopsis thaliana*," Plant Physiol. Biochem.36(7):533-537.
Thornberg et al. (Feb. 1987) "Wound-Inducible Expression of a Potato Inhibitor II Chloramphenicol Acetyltransferase Gene Fusion in Transgenic Tobacco Plants," Proc. Nat. Acad. Sci. USA 84:744-748.
Turrini et al. (Aug. 2004) "The Antifungal Dm-AMP1 Protein from Dahlia merckii Expressed in Solanum melongena is Released in Root Exudates and Differentially Affects Pathogenic Fungi and Mycorrhizal Symbiosis," New Phytologist 163(2):393-403.
Urdanqarin et al. (Mar. 2000) "A Defensin Gene Expressed in Sunflower Inflorescence," Plant Physiol. Biochem. 38(3):253-258.
Urwin et al.(Mar. 1998) "Enhanced Transgenic Plant Resistance to Nematodes by Dual Proteinase Inhibitor Constructs," Planta 204(4):472-479.
Van der Elzen et al. (1993) "Virus and Fungal Resistance: From Laboratory to Field," Phil. Trans. R. Soc. Lond. B 342:271-278.
Van der Heuvel et al. (2001) "The Expression of tgas118, Encoding a Defensin in Lysopersicon esculentum, is Regulated by Gibberellin," J. Exp. Bot. 52(360):1427-1436.
Van der Weerden et al. (2004) "Permeabilization of Fungal Membranes by a Floral Defensin," ComBio 2004 Perth, Sep. 26-30, 2004, 1 page.
Van der Weerden et al. (2005) "A Fluorescence Approach to Studying the Interaction of Defensin with Fungi," ComBio2005 Adelaide, Sep. 25-29, 2005, 1 page.
Van der Weerden et al. (2005) "Defensin Gets Under Fungal 'Skin'," MPG2005, Melbourne, 1 page.
Van Der Weerden et al. (May 23, 2008) "The Plant Defensin, NaD1, Enters the Cytolplasm of *Fusarium oxysporum* Hyphae," J. Biol. Chem. 283(21):14445-14452.
Veldhuis et al., "Cellular DNA Content of Marine Phytoplankton Using Two New Fluorochromes: Taxonomic and Ecological Implications", J. Phycol. 1997, 33:527-541, Bigelow Laboratory for Ocean Sciences.
Wang et al. (1999) "Constitutive Expression of Pea Defense Gene DRR206 Confers Resistance to Blackleg (*Leptosphaeria maculans*) Disease in Transgenic Canola(*Brassica napus*)," Mol. Plant-Microbe Interact. 12(5):410-418.
Wijaya et al. (2000) "Defense Proteins from seed of *Cassia fistula* Include a Lipid Transfer Protein Homologue and a Protease Inhibitory Plant Defensis," Plant Science. 159(2):243-255.
Wilkins et al. (May 1989) "Expression of Rice Lectin is Governed by Two Temporally and Spatially Regulated mRNAs in Developing Embryos," Plant Cell 1 :541-549.
Williams et al. (1979) "Screening for Resistance to Blackleg of Crucifiers in the Seedling Stage," Proceedings of Ecucarpia Cruciferae Conference, Wageningen, The Netherlands, pp. 164-170.
Wisniewski et al. (Dec. 2003) "Characterization of a Defensin in Bark and Fruit Tissues of Peach and Antimicrobial Activity of a Recombinant Defensin in the Yeast, *Pichia pastoris*," Physiol. Plant. 119(4):563-572.
Yamada et al. (1999, GenBank Accession No. AB005266).
Yount et al. (2005) "Immunocontinuum: Perspectives in Antimicrobial Peptide Mechanisms of Action and Resistance," Protein Pept. Lett. 12(1):49-67.
Yount et al. (Nov. 1995) "Rat Neutrophil Defensins. Precursor Structures and Expression During Neutriphilic Myelopoiesis," J. Immunol. 155:4476-4484.
Yu et al. (2000) Direct Submission Accession No. S30578.
Zhang et al. (1997) "Purification and Characterization of a New Class of Insect a-Amylase Inhibitors from Barley," Cereal Chem. 74(2):119-122.
Zhang et al. (Apr. 1997) "Fabatins: New Antimicrobial Plant Peptides," FEMS Microbial. Lett.149 (1):59-64.
Zhu et al. (Jun. 2007) "Ectopic Expression of Dahlia merckii Defensin DmAMP 1 Improves Papaya Resistance to Phytophthora palmivora by Reducing Pathogen Vigor," Planta 226(1):87-97.

* cited by examiner

```
>SS_BAA-HvCPI6 for expression in corn
         10        20        30        40        50        60        70
    ....|....|....|....|....|....|....|....|....|....|....|....|....|....|
    atggccaacaagcacctgtccctctcctcttcctcgtgctcggcctctcggcctccctcgcctcgg
     M  A  N  K  H  L  S  L  S  L  F  L  V  L  G  L  S  A  S  L  A  S 80        90       100       110       120       130       140
    ....|....|....|....|....|....|....|....|....|....|....|....|....|....|
    gagccacctcggccctcggccgccggcgtgcttctgggcgggtggagccccgtcaaggacgtgaacga
     G  A  T  S  A  L  G  R  R  G  V  L  L  G  G  W  S  P  V  K  D  V  N  D 150       160       170       180       190       200       210
    ....|....|....|....|....|....|....|....|....|....|....|....|....|....|
    cccgcacgtccaggagctaggcggtgggcggtggcccagcacgccagcctagccaaggacgggctgctc
     P  H  V  Q  E  L  G  G  W  A  V  A  Q  H  A  S  L  A  K  D  G  L  L 220       230       240       250       260       270       280
    ....|....|....|....|....|....|....|....|....|....|....|....|....|....|
    ttccgccgggtgacgcgcggcgagcagcaggtggtgtccgggatgaactaccgcctcttcgtggtcgcgg
     F  R  R  V  T  R  G  E  Q  Q  V  V  S  G  M  N  Y  R  L  F  V  V  A 290       300       310       320       330       340       350
    ....|....|....|....|....|....|....|....|....|....|....|....|....|....|
    cggacggctccggcaagagggtgacctatctcgcgcagatctacgagcactggagcaggaccgcaagct
     A  D  G  S  G  K  R  V  T  Y  L  A  Q  I  Y  E  H  W  S  R  T  R  K  L 360       370
    ....|....|....|....|....|....|.
    cacgtccttcaagccggctgccggcggctga
     T  S  F  K  P  A  A  G  G  *
```

Figure 15

```
>SS_BAA-HvCPI6-L-HXP4-CTPP_NaD1

10        20        30        40        50        60        70
....|....|....|....|....|....|....|....|....|....|....|....|....|....|
atggccaacaagcacctgtccctctccctcttcctcgtgctcctcggcctctccgcctcctcgcctccg
 M  A  N  K  H  L  S  L  S  L  F  L  V  L  L  G  L  S  A  S  L  A  S 80        90       100       110       120       130       140
....|....|....|....|....|....|....|....|....|....|....|....|....|....|
gagccacctcggcctcggccgcgcggcgtgcttctgggcggtggagcccgtcaaggacgtgaacga
 G  A  T  S  A  L  G  R  R  G  V  L  L  G  G  W  S  P  V  K  D  V  N  D 150       160       170       180       190       200       210
....|....|....|....|....|....|....|....|....|....|....|....|....|....|
cccgcacgtccaggagctaggcgggtgggcggtggcccagcacgccagcctagccaaggacggctgctc
   P  H  V  Q  E  L  G  G  W  A  V  A  Q  H  A  S  L  A  K  D  G  L  L 220       230       240       250       260       270       280
....|....|....|....|....|....|....|....|....|....|....|....|....|....|
ttccgccgggtgacgcgcggcgagcagcaggtggtgtccgggatgaactaccgcctcttcgtggtcgcgg
 F  R  R  V  T  R  G  E  Q  Q  V  V  S  G  M  N  Y  R  L  F  V  V  A 290       300       310       320       330       340       350
....|....|....|....|....|....|....|....|....|....|....|....|....|....|
cggacggctccggcaagagggtgacctatctcgcgcagatctacgagcactggagcaggacccgcaagct
 A  D  G  S  G  K  R  V  T  Y  L  A  Q  I  Y  E  H  W  S  R  T  R  K  L 360       370       380       390       400       410       420
....|....|....|....|....|....|....|....|....|....|....|....|....|....|
cacgtcttcaagccggctgccggcggcgaggagaagaagaacagggagtgcaaaacagagagcaacacg
   T  S  F  K  P  A  A  G  GE  E  K  K  N  R  E  C  K  T  E  S  N  T 430       440       450       460       470       480       490
....|....|....|....|....|....|....|....|....|....|....|....|....|....|
ttccctggcatctgcattactaagccaccgtgccgcaaggcctgcatctccgaaaagtttacagacgggc
 F  P  G  I  C  I  T  K  P  P  C  R  K  A  C  I  S  E  K  F  T  D  G 500       510       520       530       540       550       560
....|....|....|....|....|....|....|....|....|....|....|....|....|....|
actgttccaaaatcctccgcaggtgcctctgcacgaagccgtgcgttttcgacgagaagatgacgaagac
 H  C  S  K  I  L  R  R  C  L  C  T  K  P  C  V  F  D  E  K  M  T  K  T 570       580       590       600       610       620       630
....|....|....|....|....|....|....|....|....|....|....|....|....|....|
tggggcggagattctcgctgaggaggccaagactctggcggctgccctgctggaagaggaaattatggac
   G  A  E  I  L  A  E  E  A  K  T  L  A  AA  L  L  E  EE  I  M  D ....|.
aattga
 N  *
```

Figure 16

MODIFIED PLANT DEFENSINS USEFUL AS ANTI-PATHOGENIC AGENTS

CROSS-REFERENCE TO RELATED APPLICATIONS

This application is a divisional application of U.S. application Ser. No. 13/983,941, filed Oct. 28, 2013, which is a U.S. National Stage application filed under 35 U.S.C. § 371 of International Application No. PCT/AU2012/000112, filed Feb. 7, 2012, which claims the benefit of U.S. Provisional Application No. 61/440,309, filed Feb. 7, 2011. Each of these applications is incorporated by reference in its entirety herein.

FIELD

This disclosure relates generally to the field of anti-pathogenic agents, including a modified defensin molecule with anti-pathogen activity. Genetically modified plants and their progeny or parts expressing or containing the modified defensin and anti-pathogen compositions for use in horticulture and agriculture and as animal and human medicaments are also provided.

BACKGROUND

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

One of the major difficulties facing the horticultural and agricultural industries is the control of infestation and resulting damage by pathogens such as fungal pathogens. Plant pathogens account for millions of tonnes of lost production on an annual basis. Although fungicides and other anti-pathogenic chemical agents have been successfully employed, there is a range of environmental and regulatory concerns with the continued use of chemical agents to control plant pests. Furthermore, the increasing use of chemical pesticides is providing selective pressure for the emergence of resistance in populations of pests. There is clearly a need to develop alternative mechanisms of inducing resistance in plants to pathogens such as fungi, insects, microorganisms, nematodes, arachnids, protozoa and viruses.

The plant innate immune system comprises both constitutive or pre-formed and inducible components. Pre-formed immunity includes various physical barriers such as wax layers on leaves and rigid cell walls as well as expression of various antimicrobial proteins (Nurnberger et al. (2004) *Immunol Rev* 198:249-266). The inducible response can include fortification of the cell wall (Showalter (1993) *Plant Cell* 5(1):9-23) as well as up-regulation of secondary metabolites (Metlen et al. (2009) *Plant Cell Environ* 32(6): 641-653) and antimicrobial proteins (Berrocal-Lobo et al. (2002) *Plant Physiol* 128(3):951-961; Li and Asiegbu (2004) *J Plant Res* 117(2):155-162) which occurs in response to various biotic and abiotic stimuli. These responses can occur locally at the site of infection or in distant, uninfected parts of the plant to produce a systemic response. Inducible immunity can also occur via a gene-for-gene response whereby pathogen-associated molecular patterns (PAMPS) are recognized by specific pattern recognition receptors (PRRs) resulting in a hypersensitive response that prevents further spread of the pathogen (see Jones and Dangl (2006) *Nature* 444(7117):323-329).

Small, disulfide-rich proteins play a large role in both the constitutive and inducible aspects of plant immunity. They can be categorized into families based on their cysteine arrangements and include the thionins, snakins, thaumatin-like proteins, havein- and knottin-type proteins, lipid transfer proteins and cyclotides as well as defensins.

Plant defensins are small (45-54 amino acids), basic proteins with four to five disulfide bonds (Janssen et al. (2003) *Biochemistry* 42(27):8214-8222). They share a common disulfide bonding pattern and a common structural fold, in which a triple-stranded, antiparallel β-sheet is tethered to an α-helix by three disulfide bonds, forming a cysteine-stabilized αβ motif (CSαβ [see FIG. 1]). A fourth disulfide bond also joins the N- and C-termini leading to an extremely stable structure. A variety of functions have been attributed to defensins, including anti-bacterial activity, protein synthesis inhibition and α-amylase and protease inhibition (Colilla et al. (1990) *FEBS Lett* 270(1-2):191-194; Bloch and Richardson (1991) *FEBS Lett* 279(1):101-104). Plant defensins have been expressed in transgenic plants, resulting in increased resistance to target pathogens. For example, potatoes expressing the alfalfa defensin (MsDef1, previously known as alfAFP) showed significant resistance against the fungal pathogen *Verticillium dahliae* compared to non-transformed controls (Gao et al. (2000) *Nat Biotechnol* 18(121:1307-1310). Expression of a Dahlia defensin (DmAMP1) in rice was sufficient to provide protection against two major rice pathogens, *Magnaporthe oryzae* and *Rhizoctonia solani* (Jha et al. (2009) *Transgenic Res* 18(11: 59-69).

Despite their conserved structure, plant defensins share very little sequence identity, with only the eight cysteine residues completely conserved. The cysteine residues are commonly referred to as "invariant cysteine residues", as their presence and location are conserved amongst defensins. Based on sequence similarity, plant defensins can be categorized into different groups (see FIG. 2). Within each group, sequence homology is relatively high whereas inter-group amino acid similarity is low. The anti-fungal defensins from distinct groups appear to act via different mechanisms.

Plant defensins can be divided into two major classes. Class I defensins consist of an endoplasmic reticulum (ER) signal sequence followed by a mature defensin domain. Class II defensins are produced as larger precursors with C-terminal pro-domains or pro-peptides (CTPPs) of about 33 amino acids. Most of the Class II defensins identified to date have been found in solanaceous plant species. An alignment of Class II solanaceous defensins is provided in FIG. 3. NsD1 and NsD2 referred to in FIG. 3 represent novel defensins identified in accordance with the present disclosure. Their inclusion in FIG. 3 is not to imply they form part of the prior art.

Class II solanaceous defensins display anti-fungal activity and are expressed in floral tissues. They include NaD1, which is expressed in high concentrations in the flowers of ornamental tobacco *Nicotiana alata* (Lay et al. (2003) *Plant Physiol* 131(3):1283-1293). NaD1 is the only Class II solanaceous defensin for which the mechanism of anti-fungal activity has been investigated. The activity of this peptide involves binding to the cell wall, permeabilization of the plasma membrane and entry of the peptide into the cytoplasm of the hyphae (van der Weerden et al. (2008) *J Biol Chem* 283(21):14445-14452). Unlike many other defensins, NaD1 appears to be specific for filamentous fungi and has no effect on the growth of yeast, bacteria or mammalian cells.

Expression of NaD1 in cotton enhances the resistance to the fungal pathogens *Fusarium oxysporum* f.sp. *vasinfectum* and *Verticillium dahliae*. Under field conditions, plants expressing NaD1 were twice as likely to survive as untransformed control plants and the lint yield per hectare was doubled. Despite this, there was still a significant level of disease in the NaD1-expressing plants.

The structure of defensins consists of seven 'loops', defined as the regions between cysteine residues. Loop 1 encompasses the first β-strand (1A) as well as most of the flexible region that connects this β-strand to the α-helix (1B) between the first two invariant cysteine residues. FIG. 5 shows the loop structure of NaD1 including the conserved cysteine residues. Loops 2, 3 and the beginning of 4 (4A) make up the α-helix, while the remaining loops (4B-7) make up β-strands 2 and 3 and the flexible region that connects them (β-hairpin region). This hairpin region of plant defensins forms a γ-core motif that is found in many anti-microbial peptides of diverse classes (Yount and Yeaman (2005) *Protein Pept Lett* 12(1):49-67).

This β-hairpin region appears to be essential for the biological activity of plant defensins. Mutations in this region of the radish defensin RsAFP2 (See FIG. 2) generally had a negative impact on its anti-fungal activity. In fact, eight out of the twelve residues identified as essential for anti-fungal activity are located in this region (De Samblanx et al. (1997) *J Biol Chem* 272(2):1171-1179). Furthermore, a chemically synthesized peptide corresponding to this region of the molecule also has anti-fungal activity on its own (Schaaper et al. (2001) *J. Pept. Res.* 57(5):409-418). In a separate study, the six residues located in loop 5 of VrD2, a defensin from *Vigna radiata*, were shown to be essential for its α-amylase inhibitory activity (Lin et al. (2007) *Proteins* 68(2):530-540). A third study investigated the activity of chimeric proteins containing regions from a defensin with anti-fungal activity (MsDef1) and one without (MtDef2). Chimeric defensins that contained the β2-β3 hairpin region of MsDef1 had almost the same activity as the full MsDef1 protein and chimeric defensins that contained this region from MtDef2 had no activity (Spelbrink et al. (2004) *Plant Physiol* 135(4):2055-2067).

A flexible loop connecting the first β-strand and the α-helix located adjacent and N-terminal of the second invariant cysteine residue (Loop 1B) has been reported to play a minor role in the anti-fungal activity in some defensins when associated as a patch with residues from Loop5. A mutagenesis study of RsAFP2 identified two amino acids important for activity that were located in this region (De Samblanx et al, 1997 supra). However, when this region of the anti-fungal defensin MsDef1 was replaced with the corresponding region from the non-anti-fungal defensin, there was only a modest change in anti-fungal activity (Spelbrink et al, 2004 supra).

Class II solanaceous defensins have variable degrees of activity against fungi. Some Class I defensins exhibit very low anti-fungal activity. Attempts to modify the defensins to improve and broaden their anti-pathogen activity have hitherto been largely unsuccessful. Development of resistance to some defensins is also a potential problem. There is a need to develop protocols to manipulate the level and spectrum of anti-pathogen activity of defensins. The creation of a range of novel defensins with antipathogen activity also facilitates combating the development of resistance.

SUMMARY

Throughout this specification, unless the context requires otherwise, the word "comprise", or variations such as "comprises" or "comprising", will be understood to imply the inclusion of a stated element or integer or method step or group of elements or integers or method steps but not the exclusion of any other element or integer or method step or group of elements or integers or method steps.

As used in the subject specification, the singular forms "a", "an" and "the" include plural aspects unless the context clearly dictates otherwise. Thus, for example, reference to "a defensin" includes a single defensin, as well as two or more defensins; reference to "an amino acid, substitution, addition and/or deletion" includes a single amino acid, substitution, addition and/or deletion, as well as two or more amino acids, substitutions, additions and/or deletions; reference to "the aspect" includes a single aspect, as well as two or more aspects as taught in the specification; and so forth.

Nucleotide and amino acid sequences are referred to by a sequence identifier number (SEQ ID NO). The SEQ ID NOs correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present disclosure teaches artificially modified Class II solanaceous defensins which constitute a new family of defensins with anti-pathogen activity. In an embodiment, anti-pathogen activity is enhanced in the modified Class II solanaceous defensins with respect to inter alia one or more of level and/or spectrum of activity, stability and/or membrane permeabilization capacity compared to the Class II solanaceous defensin prior to modification. The modified defensins are taught herein to be useful in horticulture and agriculture to control pathogen infestation and growth as well as in the manufacture of animal and human medicaments. They may be used alone or in combination with a chemical pathogenicide, an anti-pathogen protein and/or a proteinase inhibitor or precursor form thereof. The availability of the new family of defensins also assists in combating against pathogen resistance to a particular defensin.

A Class II solanaceous defensin is used as a backbone wherein the loop region between the first β-strand (β-strand 1) and the α-helix on the defensin N-terminal end portion (also described as the first flexible loop) is modified by an amino acid substitution, addition and/or deletion and/or a loop region from another defensin, or a modified form thereof, is grafted onto the Class II solanaceous defensin to replace all or part of this loop region. The backbone defensin may also optionally comprise additional mutations outside this loop region. When present, from 1 to about 50 additional mutations in the form of an amino acid substitution, addition and/or deletion may be made to one or more regions outside the Loop 1B region.

An artificially created defensin is provided comprising:
(i) an amino acid backbone derived from or corresponding to a Class II solanaceous defensin having a loop domain within its N-terminal end region;
(ii) the loop domain on the backbone being subjected to one or more of: (a) an amino acid substitution, addition and/or deletion; and/or (b) replacement of all or part of the first loop domain by a loop or a modified form thereof from another defensin;

wherein the artificially created defensin exhibits anti-pathogen activity. The disclosure teaches a single or multiple amino acid substitution, addition and/or deletion which includes converting a Class II solanaceous defensin first loop domain and in particular Loop 1B, to an amino acid sequence corresponding to the loop domain of a Class I defensin. Alternatively, another Class II defensin Loop 1B region is used to replace a Loop 1B on a Class II defensin. The modified Class II solanaceous defensin may also contain one or more additional amino acid substitutions, additions and/or deletions outside this loop region. If present, from 1 to about 50 additional mutations may be located outside the loop region.

In an embodiment, the anti-pathogen activity is enhanced compared to the Class II defensin prior to modification. By "enhanced" means an improvement in one or more of level and/or spectrum of activity, stability and/or membrane permeabilization capacity compared to the non-modified Class II defensin.

Class II solanaceous defensins for use as a backbone include a defensin having at least 70% amino acid sequence similarity over an approximately 20 contiguous amino acid residue sequence at the C-terminal end of the NaD1 mature domain including the most C-terminal invariant cysteine (C) residue (SEQ ID NO:52). Examples of Class II solanaceous defensins include NaD1, NsD1, NsD2, PhD1, PhD2, TPP3, FST, NeThio1, NeThio2, NpThio1, Na-gth and Cc-gth. Other backbone defensins include C20 from *Capsicum* and SL549 from *Nicotiana*. NsD1 and NsD2 are from *Nicotiana suaveolens*, with amino acid sequences as set forth in SEQ ID NOs:49 and 51, respectively.

Reference to the "loop domain" at the N-terminal end region of the Class II solanaceous defensin includes the entire loop region defined by being flanked by the first two (invariant) cysteine (C) amino acid residues. This is the first flexible loop in the defensin in its N-terminal region. However, in an embodiment, the "loop domain" refers to the loop region beginning at the end of the first β-strand and ending at the N-terminal side of the second invariant cysteine amino acid residue. This region is referred to as "L1B" [Loop 1B] in FIG. 5. In NaD1, an example of a Class II solanaceous defensin, this region or domain comprises the amino acid sequence, in single letter code, NTFPGI (see FIG. 5). Other Class II solanaceous defensin first loop regions are shown in FIG. 3. FIG. 4 is a representation of amino acid sequence alignments of different classes of defensins showing the eight conserved cysteine residues.

Hence, the Loop 1B region of the Class II solanaceous defensin backbone may be mutated or a Loop 1B region from another defensin such as from a Class I defensin or another Class II defensin may be grafted in its place to generate a Loop 1B amino acid sequence of $X_1 X_2 X_3 X_4 X_5 X_6$, (SEQ ID NO:1) wherein:

$X_1$ is A, R, N, D, C, Q, E, G, H, I, L, K, M, F, P, S, T, W, Y or V or a naturally occurring modified form thereof;

$X_2$ is A, R, N, D, C, Q, E, G, H, I, L, K, M, F, P, S, T, W, Y or V or a naturally occurring modified form thereof;

$X_3$ is A, R, N, D, C, Q, E, G, H, I, L, K, M, F, P, S, T, W, Y or V or a naturally occurring modified form thereof;

$X_4$ is A, R, N, D, C, Q, E, G, H, I, L, K, M, F, P, S, T, W, Y or V or a naturally occurring modified form thereof;

$X_5$ is A, R, N, D, C, Q, E, G, H, I, L, K, M, F, P, S, T, W, Y or V or a naturally occurring modified form thereof; and/or $X_6$ is A, R, N, D, C, Q, E, G, H, I, L, K, M, F, P, S, T, W, Y or V or a naturally occurring modified form thereof;

using single letter amino acid nomenclature, wherein the amino acid sequence $X_1 X_2 X_3 X_4 X_5 X_6$ in the mutated Class II solanaceous defensin does not correspond to an amino acid sequence of the Loop 1B region from the Class II solanaceous defensin forming the backbone prior to modification.

In an embodiment, the Loop 1B region of the Class II solanaceous defensin backbone is mutated or a Loop 1B region from another defensin such as from a Class I defensin is grafted in its place to generate an amino acid sequence of $X_1 X_2 X_3 X_4 X_5 X_6$ (SEQ ID NO:86) wherein:

$X_1$ is N, G, D, H, K, A, E, Q, T, P, L, M, S, or R;

$X_2$ is K, R, G, H, L, N, F, I, S, T or Y;

$X_3$ is W, Y, H, L, G, F or P;

$X_4$ is P, K, S, R, H, T, E, V, N, Q, D or G;

$X_5$ is S, K, Y, F, G or H; and/or $X_6$ is P, V, L, T, A, F, N, K, R, M, G, H, I or Y;

using single letter amino acid nomenclature, wherein the amino acid sequence $X_1 X_2 X_3 X_4 X_5 X_6$ does not correspond to an amino acid sequence of the Loop 1B region from the Class II solanaceous defensin forming the backbone prior to modification.

In another embodiment, the Loop 1B region of the Class II solanaceous defensin backbone is mutated or a Loop 1B region from another defensin such as from a Class I defensin is grafted in its place to generate an amino acid sequence of $X_1 X_2 X_3 X_4 X_5 X_6$, (SEQ ID NO:55) wherein:

$X_1$ is N, H, Q, D, K or E;

$X_2$ is R, H, T, K or G;

$X_3$ is F, H, Y or W;

$X_4$ is P, K, S or R;

$X_5$ is G or F; and/or $X_6$ is P, V, I, N;

using single letter amino acid nomenclature, wherein the amino acid sequence $X_1 X_2 X_3 X_4 X_5 X_6$ does not correspond to an amino acid sequence of the Loop 1B region from the Class II solanaceous defensin prior to modification.

In an embodiment, the artificially created or modified defensin comprises the amino acid sequence as set forth in SEQ ID NO:57. In this sequence, the Loop 1B region is defined as $X_1 X_2 X_3 X_4 X_5 X_6$ (SEQ ID NO:56) wherein:

$X_1$ is an amino acid selected from the list consisting of: L, F, S, I, A, H, Y, Q, D, K, G;

$X_2$ is an amino acid selected from the list consisting of: S, V, F, I, K, L, A, P, N, T, R, H, G;

$X_3$ is an amino acid selected from the list consisting of: A, F, W, N, I, S, Y, P, L, H;

$X_4$ is an amino acid selected from the list consisting of: K, G, E, R, A, P, F, Q, V, S;

$X_5$ is an amino acid selected from the list consisting of: M, G, K, D, S, Y, P, E, N, F; and $X_6$ is an amino acid selected from the list consisting of: V, T, M, S, W, A, P, G, E, K, L, H, I, N.

In an embodiment, the artificially created or modified defensin comprises the amino acid sequence as set forth in SEQ ID NO:84. In this sequence, the Loop 1B region is defined as $X_1 X_2 X_3 X_4 X_5 X_6$ (amino acids 8-13 of SEQ ID NO:84) wherein: $X_1$ is an amino acid selected from the list consisting of: N, H, Q, D, K, E;

$X_2$ is an amino acid selected from the list consisting of: R, H, T, K, G;

$X_3$ is an amino acid selected from the list consisting of: F, H, Y W;

$X_4$ is an amino acid selected from the list consisting of: P, K, S, R;

$X_5$ is an amino acid selected from the list consisting of: G, F; and $X_6$ is an amino acid selected from the list consisting of: P, V, I, N.

In an embodiment, taught herein is an isolated solanaceous Class II defensin having anti-pathogen activity comprising an amino acid sequence as set forth in SEQ ID NO:39 or an amino acid sequence having at least 70% similarity to SEQ ID NO:39, the modification being an amino acid substitution, addition or deletion to a Loop 1B amino acid sequence in the Class II solanaceous defensin. SEQ ID NO:39 is the amino acid sequence of the NaD2 Loop 1B sequence (HRFKGP) in an NaD1 backbone to create HXP4. The present disclosure does not extend to NaD1 but to a modified NaD1 in which its Loop 1B sequence has been altered. The present disclosure further does not extend to FST, NeThio1, NeThio2, C20, SL549, PhD1, PhD2, TPP3, Na-gth or Cc-gth but to a modified form of FST, NeThio1, NeThio2, C20, SL549, PhD1, PhD2, TPP3, Na-gth or Cc-gth in which its Loop 1B sequence has been altered.

As indicated above, these aspects apply to any Class II solanaceous defensin including a defensin having an amino acid sequence similarity of 70% or more to the approximately 20 contiguous amino acid residue sequence at the C-terminal end region of the NaD1 mature domain. The 20 contiguous amino acid sequence is defined by SEQ ID NO:52.

In an embodiment, the Loop 1B region on the backbone amino acid sequence is modified to HRFKGP (SEQ ID NO:29), QHHSFP (SEQ ID NO:30), DTYRGV (SEQ ID NO:31), or to any one of SEQ ID NOs:67 to 79, PTWEGI (SEQ ID NO:32), DKYRGP (SEQ ID NO:33), KTFKGI (SEQ ID NO:34), KTWSGN (SEQ ID NO:35), EGWGK (SEQ ID NO:91), GTWSGV (SEQ ID NO:37) or AGFKGP (SEQ ID NO:38) [using single letter amino acid nomenclature]. Conveniently, this is accomplished by grafting the Loop 1B region from NaD2 (SEQ ID NO:29)(HRFKGP), γ-zeathionin2 (SEQ ID NO:30)(QHHSFP), PsD1 (SEQ ID NO:31)(DTYRGV), MsDef1 (SEQ ID NO:33)(DKYRGP), SoD2 (SEQ ID NO:34)(KTFKGI) or DmAMP1 (SEQ ID NO:35)(KTWSGN) or a Loop 1B defined by SEQ ID NOs:67 to 79 onto the Class II solanaceous defensin backbone at the site of its Loop 1B amino acid sequence or modifying an existing Loop 1B region to generate a Loop 1B amino acid sequence selected from HRFKGP (SEQ ID NO:29), QHHSFP (SEQ ID NO:30), DTYRGV (SEQ ID NO:31), DKYRGP (SEQ ID NO:33), KTFKGI (SEQ ID NO:34) and KTWSGN (SEQ ID NO:35). The Class II solanaceous defensin may comprise the modified loop region alone or in combination with an amino acid substitution, addition and/or deletion to the defensin backbone outside the loop region. As indicated above, a Loop 1B as defined in SEQ ID NOs:67 to 79 may also be used or a Class II solanaceous Loop 1B may be substituted onto another Class II solanaceous defensin backbone.

An artificially created defensin is therefore provided comprising a backbone amino acid sequence from a Class II solanaceous defensin having a loop region between the first β-strand and the α-helix on the N-terminal end portion of the defensin wherein the loop region is modified by an amino acid substitution, deletion and/or addition to generate a defensin which has anti-pathogen activity.

In an embodiment, there is provided an artificially created defensin comprising a backbone amino acid sequence from a Class II solanaceous defensin having a Loop 1B region N-terminal to the second invariant cysteine residue wherein the Loop 1B region is modified by an amino acid substitution, addition and/or deletion to generate a defensin which has anti-pathogen activity.

Another embodiment provides an artificially created defensin comprising a backbone amino acid sequence from a Class II solanaceous defensin having a Loop 1B region N-terminal to the second invariant cysteine residue wherein the Loop 1B region is modified by an amino acid substitution, addition and/or deletion to generate a defensin which has enhanced anti-pathogen activity compared to the Class II solanaceous defensin prior to modification, wherein the Class II solanaceous defensin comprises a C-terminal portion of the mature domain having at least about 70% similarity to the amino acid sequence set forth in SEQ ID NO:52 after optimal alignment. Reference to "an amino acid substitution, addition and/or deletion" means one or more substitutions, additions and/or deletions.

In an embodiment, an artificially modified solanaceous Class II defensin having anti-pathogen activity comprising an amino acid sequence as set forth in SEQ ID NO:57 or an amino acid sequence having at least 70% similarity to SEQ ID NO:57 after optimal alignment, the modification being to the solanaceous Class II defensin Loop 1B region.

In an embodiment, an artificially modified solanaceous Class II defensin having anti-pathogen activity comprising an amino acid sequence as set forth in SEQ ID NO:84 or an amino acid sequence having at least 70% similarity to SEQ ID NO:84 after optimal alignment, the modification being to the solanaceous Class II defensin Loop 1B region.

In an embodiment, the anti-pathogen activity is enhanced with respect to inter alia one or more of level and/or spectrum of activity, stability and/or membrane permeabilization compared to the Class II solanaceous defensin, prior to modification. In an embodiment, the anti-pathogen activity is anti-fungal activity. In an embodiment, the anti-pathogen activity is anti-insecticidal activity.

In a further embodiment, an artificially created defensin is provided comprising a backbone amino acid sequence from a Class II solanaceous defensin having a loop region between the first β-strand and the α-helix on the N-terminal end portion of the Class II solanaceous defensin, the defensin selected from the list consisting of NaD1, NsD1, NsD2, PhD1, PhD2, TPP3, FST, NeThio1, NeThio2, NpThio1, Na-gth, Cc-gth, C20 and SL549 and wherein the loop region is modified by an amino acid substitution, addition and/or deletion to generate a loop region comprising the amino acid sequence $X_1 X_2 X_3 X_4 X_5 X_6$, SEQ ID NO:1, wherein each of $X_1$ through $X_6$ is an amino acid residue and wherein $X_1$ is A, R, N, D, C, Q, E, G, H, I, L, K, M, F, P, S, T, W, Y or V or a naturally occurring modified form thereof; $X_2$ is A, R, N, D, C, Q, E, G, H, I, L, K, M, F, P, S, T, W, Y or V or a naturally occurring modified form thereof; $X_3$ is A, R, N, D, C, Q, E, G, H, I, L, K, M, F, P, S, T, W, Y or V or a naturally occurring modified form thereof; $X_4$ is A, R, N, D, C, Q, E, G, H, I, L, K, M, F, P, S, T, W, Y or V or a naturally occurring modified form thereof; $X_5$ is A, R, N, D, C, Q, E, G, H, I, L, K, M, F, P, S, T, W, Y or V or a naturally occurring modified form thereof; and/or $X_6$ is A, R, N, D, C, Q, E, G, H, I, L, K, M, F, P, S, T, W, Y or V or a naturally occurring modified form thereof; wherein the amino acid sequence $X_1 X_2 X_3 X_4 X_5 X_6$ does not correspond to an amino acid sequence of a Loop 1B region from a Class II solanaceous defensin; thereby generating a defensin which has anti-pathogen activity. In an embodiment, the loop region is Loop 1B located on the N-terminal side of the second invariant cysteine residue.

In an embodiment, there is provided an artificially created defensin comprising a backbone amino acid sequence from a Class II solanaceous defensin having a loop region between the first β-strand and the α-helix on the N-terminal end portion of the Class II solanaceous defensin, the defensin selected from the list consisting of NaD1, NsD1, NsD2, PhD1, PhD2, TPP3, FST, NeThio1, NeThio2, NpThio1, Na-gth, Cc-gth, C20 and SL549 and wherein the loop region is modified by an amino acid substitution, addition and/or deletion to generate a loop region comprising the amino acid sequence $X_1 X_2 X_3 X_4 X_5 X_6$, SEQ ID NO:86, wherein each of $X_1$ through $X_6$ is an amino acid residue wherein $X_1$ is N, G, D, H, K, A, E, Q, T, P, L, M, S, or R; $X_2$ is K, R, G, H, L, N, F, I, S, T or Y; $X_3$ is W, Y, H, L, G, F or P; $X_4$ is P, K, S, R, H, T, E, V, N, Q, D or G; $X_5$ is S, K, Y, F, G or H; and $X_6$ is P, V, L, T, A, F, N, K, R, M, G, H, T or Y wherein the amino acid sequence $X_1 X_2 X_3 X_4 X_5 X_6$ does not correspond to an amino acid sequence of a Loop 1B region from a Class II solanaceous defensin; thereby generating a defensin which has anti-pathogen activity. In an embodiment, the loop region is Loop 1B located on the N-terminal of the second invariant cysteine residue.

In an embodiment, an artificially created defensin is provided comprising a backbone amino acid sequence from a Class II solanaceous defensin having a loop region between the first β-strand and the α-helix on the N-terminal end portion of the Class II solanaceous defensin, the defensin selected from the list consisting of NaD1, NsD1, NsD2, PhD1, PhD2, TPP3, FST, NeThio1, NeThio2, NpThio1, Na-gth, Cc-gth, C20 and SL549 wherein the loop region on the defensin backbone is replaced with a loop region from a defensin selected from the list consisting of NaD2 (SEQ ID NO:29)(HRFKGP), Zea2 (SEQ ID NO:30) (QHHSFP), PsD1 (SEQ ID NO:31)(DTYRGV), MsDef1 (SEQ ID NO:33) (DKYRGP), SoD2 (SEQ ID NO:34) (KTFKGI) and DmAMP1 (SEQ ID NO:35)(KTWSGN) or a modified form thereof or a Loop 1B sequence selected from SEQ ID NO:67 to 79, to generate a defensin which has anti-pathogen activity.

In an embodiment, the loop region is modified by 1 or 2 or 3 or 4 or 5 or 6 amino acid substitutions, additions and/or deletions. In an embodiment, the Class II solanaceous defensin comprises both a modified loop region and an amino acid substitution, addition and/or deletion in a region of the backbone outside the loop region. When present, from 1 to about 50 amino acid substitutions, additions and/or deletions may be made to outside the loop region.

The pathogen may be a fungus (filamentous or non-filamentous), microorganism, insect, arachnid, nematode, protozoa or virus. In an embodiment, the pathogen is a fungus. In another embodiment, the pathogen is an insect. The term "enhanced anti-pathogen activity" includes a broader spectrum of action, higher level of activity, greater stability and/or enhanced membrane permeabilization activity.

In an embodiment, the pathogen is a fungus including a plant fungus and an animal fungus. An "animal fungus" includes a fungus which infects mammals including humans, such as a basidiomycete and an ascomycete.

Compositions comprising the artificially created defensin molecule as well as nucleic acid molecules encoding same are also provided herein. The compositions may be for use in or on plants or in or on animals, such as mammals including humans. The compositions may contain additional agents such as a chemical pathogenicide, proteinaceous pathogenicide and/or a serine or cysteine proteinase inhibitor or a precursor thereof.

Further provided are protocols for generating pathogen-resistant plants as well as treating plants and animals including mammals such as humans to treat or prevent pathogen infestation, growth and/or maintenance. The present disclosure further teaches the use of an artificially created defensin comprising a backbone amino acid sequence from a Class II solanaceous defensin having a loop region between the first β-strand and the α-helix on the N-terminal end portion of the Class II solanaceous defensin wherein the loop region is modified by an amino acid substitution, addition and/or deletion in the manufacture of an anti-pathogen medicament. In as aspect, a chemical or proteinaceous pathogenicide and/or a proteinase inhibitor or precursor thereof is or are used in combination with the modified defensin. In one aspect, a single genetic construct encodes a modified defensin comprising an altered Loop 1B region and a proteinase inhibitor or precursor form thereof such as NaPin1A (from *Nicotiana alata*), bovine pancreatic trypsin inhibitor (BPTI), tomato cystatin, inhibitor, S1Cys9, or barley cystatin, HvCPI6. In another embodiment, multiple constructs are used each separately encoding one or more of a modified defensin and a proteinase inhibitor or precursor form thereof.

In an embodiment, the loop region is Loop 1B.

In an embodiment, there is provided an isolated defensin from the Australian native, *Nicotiana suaveolens*, and its use as a backbone defensin molecule. The *N. suaveolens* defensins include NsD1 and NsD2. The nucleotide sequence of NsD1 and corresponding amino acid sequence are set forth in SEQ ID NOs:48 and 49, respectively. The nucleotide sequence of NsD2 and corresponding amino acid sequence are set forth in SEQ ID NOs:49 and 51, respectively. An *N. suaveolens* defensin carrying a modified Loop 1B alone or in combination with from 1 to about 50 amino acid substitutions, additions and/or deletions to the backbone is also contemplated herein. An isolated nucleic acid molecule encoding the *N. suaveolens* defensin is also provided for example, operably linked to a heterologous promoter and/or to a vector nucleic acid molecule.

Accordingly, another aspect taught herein is an isolated defensin from *Nicotiana suaveolens* having an amino acid sequence as set forth in SEQ ID NO:49 [NsD1] or an amino acid sequence having at least 70% thereto after optimal alignment. Another aspect taught herein is directed to an isolated defensin from *Nicotiana suaveolens* having an amino acid sequence as set forth in SEQ ID NO:51 [NsD2] or an amino acid sequence having at least 70% thereto after optimal alignment.

According to these aspects, the *N. suaveolens* defensin may be in isolated, purified form or as part of a formulation or composition comprising the defensin and a diluent, carrier, excipient, preservative, stabilizer and/or a solid or liquid additive.

Isolated nucleic acid molecules encoding NsD1 (SEQ ID NO:48) and NsD2 (SEQ ID NO:50), are provided herein as well as nucleic acid molecules having a nucleotide sequence with at least 70% identity to SEQ ID NO:48 or SEQ ID NO:50 after optimal alignment or a nucleic acid molecule which hybridizes to SEQ ID NO:48 or SEQ ID NO:50 or a complementary form thereof under medium stringent conditions, for example, operably linked to a heterologous promoter and/or to a vector nucleic acid molecule.

When the modified defensin is used in combination with another agent such as a proteinase inhibitor or a cystatin, a single genetic construct encoding all the proteins may be used to transform a plant cell or multiple constructs, each encoding a protein. Alternatively, a plant modified to express a defensin, may be subject to the topical application of a proteinase inhibitor or chemical pathogenicide.

A summary of sequence identifiers used throughout the subject specification is provided in Table 1.

TABLE 1

Summary of sequence identifiers

| SEQUENCE ID NO: | DESCRIPTION |
|---|---|
| 1 | Generic amino acid sequence of Loop 1B region |
| 2 | Amino acid sequence of portion of NaD1 (*Nicotiana alata*) containing Loop 1B |
| 3 | Amino acid sequence of portion of PhD1 (*Petunia hybrida*) containing Loop 1B |
| 4 | Amino acid sequence of portion of PhD2 (*Petunia hybrida*) containing Loop 1B |
| 5 | Amino acid sequence of portion of TPP3 (*Solanum lycopersicum*) containing Loop 1B |
| 6 | Amino acid sequence of portion of FST (*Nicotiana tabacum*) containing Loop 1B |
| 7 | Amino acid sequence of portion of g-thionin (*Nicotiana excelsior*) containing Loop 1B [NeThio1] |
| 8 | Amino acid sequence of portion of g-thionin (*Nicotiana excelsior*) containing Loop 1B [NeThio2] |
| 9 | Amino acid sequence of portion of g-thionin (*Nicotiana attenuata*) containing Loop 1B [Na-gth] |
| 10 | Amino acid sequence of portion of g-thionin (*Nicotiana paniculata*) containing Loop 1B [NpThio1] |
| 11 | Amino acid sequence of portion of g-thionin (*Capsicum chinense*) containing Loop 1B [Cc-gth] |
| 12 | Amino acid sequence of Loop 1B from NaD1, NsD1 and NsD2 |
| 13 | Amino acid sequence of Loop 1B from PhD1 |
| 14 | Amino acid sequence of Loop 1B from PhD2 |
| 15 | Amino acid sequence of Loop 1B TPP3 |
| 16 | Amino acid sequence of Loop 1B FST |
| 17 | Amino acid sequence of Loop 1B g-thionin (*N. excelsior*) [NeThio1] |
| 18 | Amino acid sequence of Loop 1B g-thionin (*N. excelsior*) [NeThio2] |
| 19 | Amino acid sequence of Loop 1B g-thionin (*N. attenuata*) [Na-gth] |
| 20 | Amino acid sequence of Loop 1B g-thionin (*N. paniculata*) [NpThio1] |
| 21 | Amino acid sequence of Loop 1B g-thionin (*C. chinense*) [Cc-gth] |
| 22 | Amino acid sequence of defensin NaD2 containing Loop 1B |
| 23 | Amino acid sequence of defensin g1-H containing Loop 1B |
| 24 | Amino acid sequence of defensin Psd1 containing Loop 1B |
| 25 | Amino acid sequence of defensin MsDef1 containing Loop 1B |
| 26 | Amino acid sequence of defensin DmAMP1 containing Loop 1B |
| 27 | Amino acid sequence of defensin RsAFP2 containing Loop 1B |
| 28 | Amino acid sequence of defensin g-zeathionin2 (Zea2) containing Loop 1B |
| 29 | Amino acid sequence of Loop 1B from NaD2 |
| 30 | Amino acid sequence of Loop 1B from Zea2 |
| 31 | Amino acid sequence of Loop 1B from PsD1 |
| 32 | Amino acid sequence of Loop 1B from PsD2 |
| 33 | Amino acid sequence of Loop 1B from MsDef1 |
| 34 | Amino acid sequence of Loop 1B from SoD2 |
| 35 | Amino acid sequence of Loop 1B from DmAMP1 |
| 36 | Amino acid sequence of Loop 1B from VrD1 |
| 37 | Amino acid sequence of Loop 1B from RsAFP2 |
| 38 | Amino acid sequence of Loop 1B from g1-H |
| 39 | Amino acid sequence of HXP4 (NaD2 Loop 1B [NaD2L1B] in NaD1) |
| 40 | Amino acid sequence of HXP34 (Zea2 Loop 1B [Zea2L1B] in NaD1) |
| 41 | Amino acid sequence of HXP35 (PsD1 Loop 1B [PsDL1B] in NaD1) |
| 42 | Amino acid sequence of HXP91 (MsDeF1 Loop 1B [MsDef1L1B] in NaD1) |
| 43 | Amino acid sequence of HXP92 (SoD1 Loop 1B [SoD1L1B] in NaD1) |
| 44 | Amino acid sequence of HXP58 (DmAMP1 Loop 1B [DMAMPL1B] in NaD1) |
| 45 | Amino acid sequence of HXP37 (VrD1 Loop 1B [VrD1L1B] in NaD1) |
| 46 | Amino acid sequence of HXP72 (NaD2 Loop 1B [NaD2L1B] in PhD2) |
| 47 | Amino acid sequence of HXP95 (NaD2 Loop 1B [NaD2L1B] in NsD1 |
| 48 | Nucleotide sequence encoding defensin from *Nicotiana suaveolens* |
| 49 | Amino acid sequence of NsD1 |
| 50 | Nucleotide sequence encoding NsD2 from *Nicotiana suaveolens* |
| 51 | Amino acid sequence encoding NsD2 |
| 52 | Amino acid sequence of C-terminal end amino acid sequence of NaD1 which ends and includes the most C-terminal invariant cysteine residue |
| 53 | Amino acid sequence of NaD1 C-terminal tail |
| 54 | Amino acid sequence of variable region of Loop 1B region |
| 55 | Amino acid sequence of variable region of Loop 1B region |
| 56 | Amino acid sequence of variable region of Loop 1B region |
| 57 | Amino acid sequence of NaD1 backbone having a Loop 1B defined by $X_1$ through $X_6$ |
| 58 | Amino acid sequence of C20 |
| 59 | Amino acid sequence of SL549 |

TABLE 1-continued

| Summary of sequence identifiers | |
|---|---|
| SEQUENCE ID NO: | DESCRIPTION |
| 60 | Amino acid sequence of Loop 1B from C20 |
| 61 | Amino acid sequence of NaPin1A |
| 62 | Amino acid sequence of BPTI |
| 63 | Amino acid sequence of CI-1B |
| 64 | Amino acid sequence of HVCPI6 |
| 65 | Amino acid sequence of S1Cys9 |
| 66 | Amino acid sequence of OsIa |
| 67 | Amino acid sequence at replacement Loop 1B identified following high through put screen |
| 68 | Amino acid sequence at replacement Loop 1B identified following high through put screen |
| 69 | Amino acid sequence at replacement Loop 1B identified following high through put screen |
| 70 | Amino acid sequence at replacement Loop 1B identified following high through put screen |
| 71 | Amino acid sequence at replacement Loop 1B identified following high through put screen |
| 72 | Amino acid sequence at replacement Loop 1B identified following high through put screen |
| 73 | Amino acid sequence at replacement Loop 1B identified following high through put screen |
| 74 | Amino acid sequence at replacement Loop 1B identified following high through put screen |
| 75 | Amino acid sequence at replacement Loop 1B identified following high through put screen |
| 76 | Amino acid sequence at replacement Loop 1B identified following high through put screen |
| 77 | Amino acid sequence at replacement Loop 1B identified following high through put screen |
| 78 | Amino acid sequence at replacement Loop 1B identified following high through put screen |
| 79 | Amino acid sequence at replacement Loop 1B identified following high through put screen |
| 80 | Nucleotide sequence of construct expressing HvCPI6 for expression in corn |
| 81 | Amino acid sequence of HvCPI6 |
| 82 | Nucleotide sequence of construct comprising HvCPI6-L-HXP4-CTPP (NaD1) |
| 83 | Amino acid sequence of HvCPI6-L-HXP4-CTPP (NaD1) |
| 84 | Amino acid sequence of NaD1 backbone having a Loop 1B defined by $X_1$ through $X_6$ |
| 85 | Amino acid sequence of TPP3 backbone having a Loop 1B from NaD2 (HXP107) |

Table 2 provides a summary of the nomenclature used to describe the exemplified modified defensin.

TABLE 2

| Summary of nomenclature of modified defensins | |
|---|---|
| Nomenclature | Description |
| HXP4 | NaD2 Loop 1B in NaD1 backbone |
| HXP34 | Zea2 Loop 1B in NaD1 backbone |
| HXP35 | PSD1 Loop 1B in NaD1 backbone |
| HXP37 | VrD1 Loop 1B in NaD1 backbone |
| HXP91 | MsDeF1 Loop 1B in NaD1 backbone |
| HXP92 | SoD2 Loop 1B in NaD1 backbone |
| HXP58 | DmAMP1 Loop 1B in NaD1 backbone |
| HXP72 | NaD2 Loop 1B in PhD2 backbone |
| HXP95 | NaD2 Loop 1B in NsD1 backbone |
| HXP107 | NaD2 Loop 1B in TPP3 backbone |

Table 3 is a list of single and three letter code for amino acid residues used herein.

TABLE 3

| List of single and three letter abbreviations for amino acid residues | | |
|---|---|---|
| Amino Acid | Three-letter Abbreviation | One-letter Symbol |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

| | |
|---|---|
| ✹ Antifungal | ▣ Pollen recognition |
| ▲ Protein synthesis inhibitor | ◎ Sweet tasting |
| ■ Antibacterial | △ Zinc tolerance |
| ✳ α-amylase inhibitor | ☐ Trypsin inhibitor |
| ▲ Sodium channel blocker | |

Figure 3A:
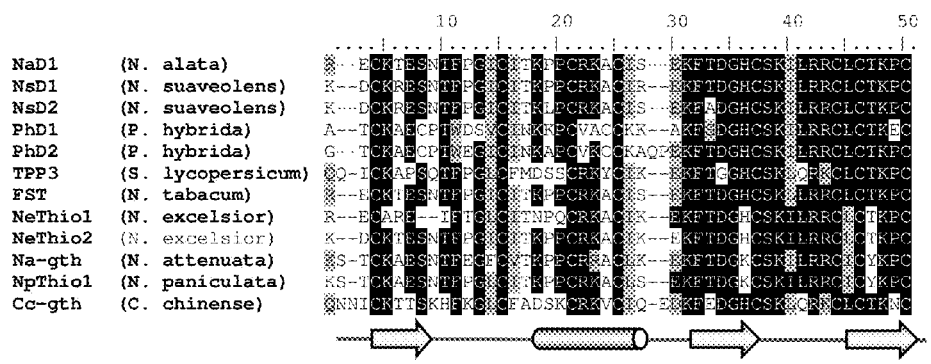

FIGS. 3A and B are representations of sequence alignments of the Class II solanaceous defensins NaD1, NsD1, NsD2, PhD1, PhD2, TPP3, FST, NeThio1, NeThio2, Na-gth, NpThio1 and Cc-gth. The amino acid sequences are given in the Sequence Listing as follows: NaD1, SEQ ID NO:2; NsD1, SEQ ID NO:49; NsD2, SEQ ID NO:51; PhD1, SEQ ID NO:3; PhD2, SEQ ID NO:4; TPP3, SEQ ID NO:5; FST, SEQ ID NO:6; NeThio1, SEQ ID NO:7; NeThio2, SEQ ID NO:8; Na-gth, SEQ ID NO:9; NpThio1, SEQ ID NO:10; and Cc-gth, SEQ ID NO:11. The shading in FIG. 3A depicts the high level of conservation between the sequences.

Figure 4:
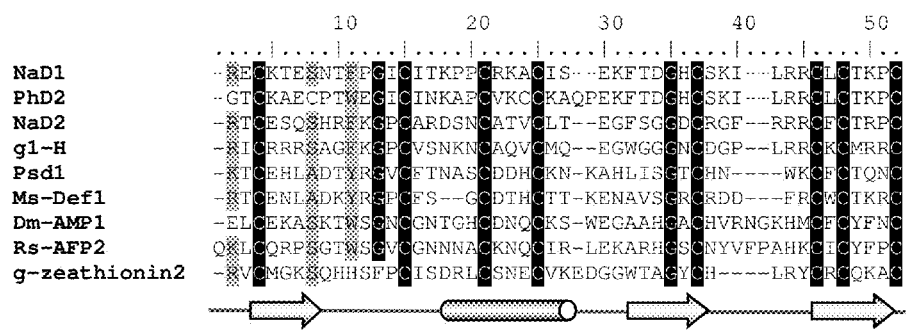

FIG. 4 is a representation of sequence alignment of defensins of different classes which reveals, apart from the eight cysteine residues which are conserved, only the amino acids at positions 7 and 10 are highly conserved. Numbering is based relative to NaD1. The sequences are given in the Sequence Listing as follows: NaD1, SEQ ID NO:2; PhD2, SEQ ID NO:4; NaD2, SEQ ID NO:22; g1-H, SEQ ID NO 23; Psd1, SEQ ID NO 24; Ms-Def1, SEQ ID NO 25; Dm-AMP1, SEQ ID NO 26; Rs-AFP2, SEQ ID NO 27; and g-zeathionin2, SEQ ID NO 28.

Figure 5:
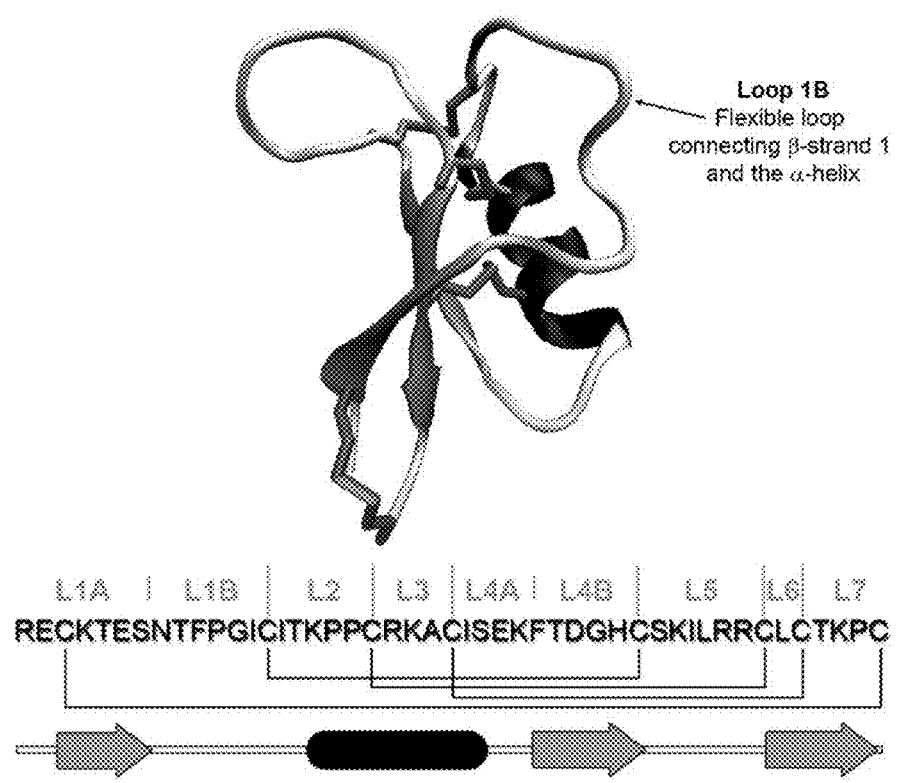

FIG. 5 is a diagrammatic representation of the loop structure of NaD1 showing the location of Loop 1B connecting β-strand 1 and the α-helix. The amino acid sequence is also given in SEQ ID NO:2.

Figure 6A:
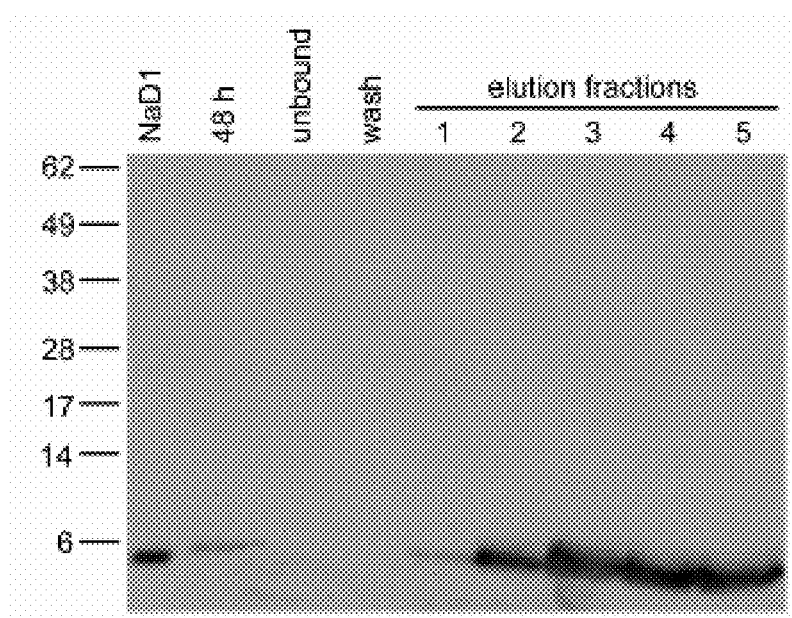

FIG. 6A is a representative of an immunoblot depicting expression and purification of recombinant NaD1 (rNaD1). P. pastoris expression medium collected at 48 hours (30 μL) as well as samples from various stages of SP sepharose purification including the unbound fraction (30 μL), wash fraction (30 μL) and the first five 1.5 mL elution fractions (30 μL of each) were separated by SDS-PAGE and examined by immunoblotting with the α-NaD1 antibody. NaD1 from flowers (200 ng) was used as a positive control. rNaD1 could be detected in the 48 hour expression media as well as the SP sepharose elution fractions.

Figure 6B:
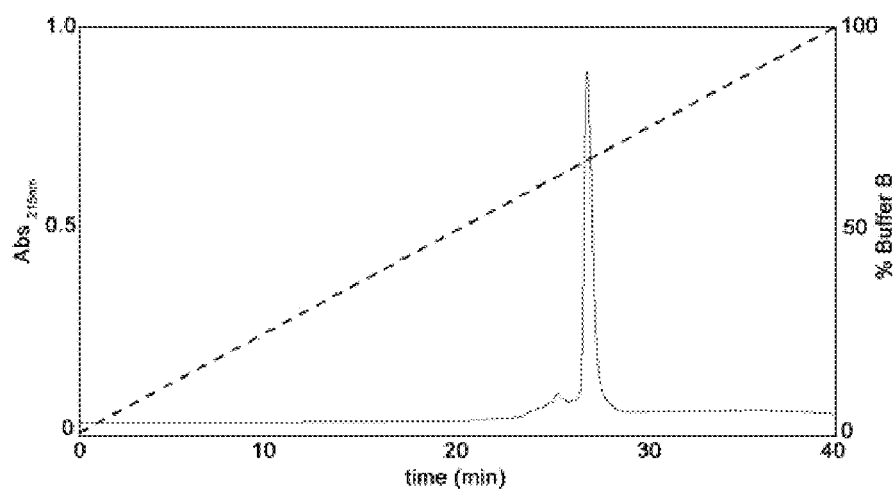

FIG. 6B is a representation of a reverse phase HPLC trace illustrating purity of rNaD1 purified from P. pastoris using SP sepharose. SP sepharose elution fractions containing rNaD1 were loaded onto an analytical C8 RP-HPLC column and eluted using a 40 min linear gradient (0-100% buffer B). Proteins were detected by absorbance at 215 nm. A single major protein was detected indicating the protein was highly pure.

Figure 6C:
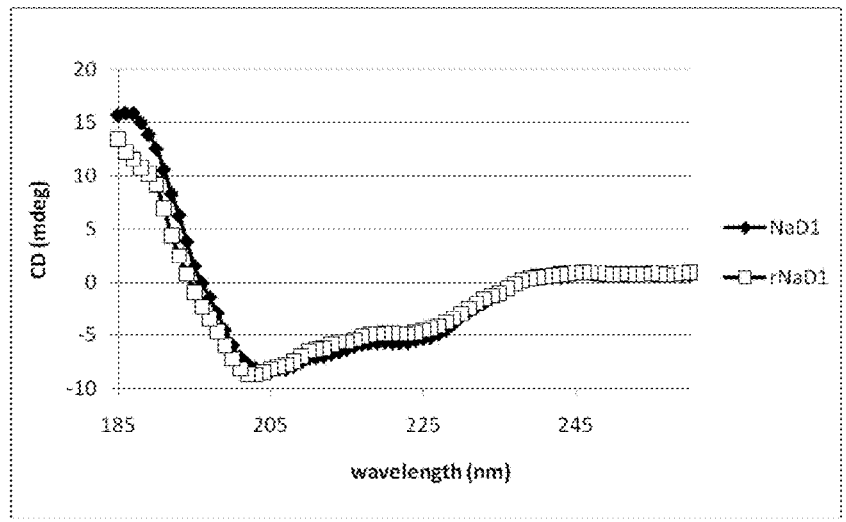

FIG. 6C is a representation of the structure of rNaD1 to native NaD1 purified from flowers. The far UV circular dichroism spectra of rNaD1 (Open squares) and native NaD1 (closed diamonds) was compared and demonstrated no significant differences indicating that rNaD1 was correctly folded.

Figure 6D:
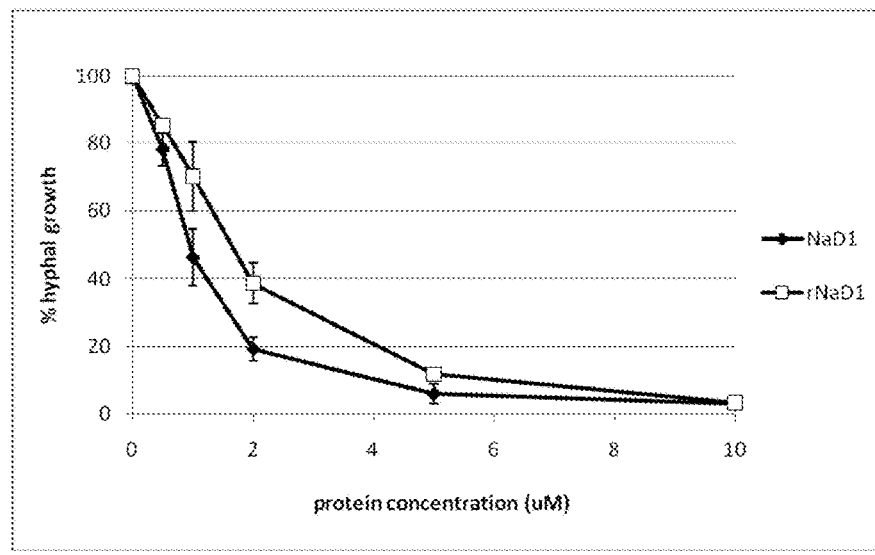

FIG. 6D is a representation of the anti-fungal activity of rNaD1 to native NaD1 purified from flowers. Hyphal growth of *Fusarium oxysporum* f. sp. *vasinfectum* in the presence of rNaD1 (open squares) or native NaD1 (closed diamonds) is plotted relative to the growth of a no protein control for the same period. Graph represents data from three separate experiments performed in quadruplicate. Error bars represent standard error of the mean.

Figure 7:
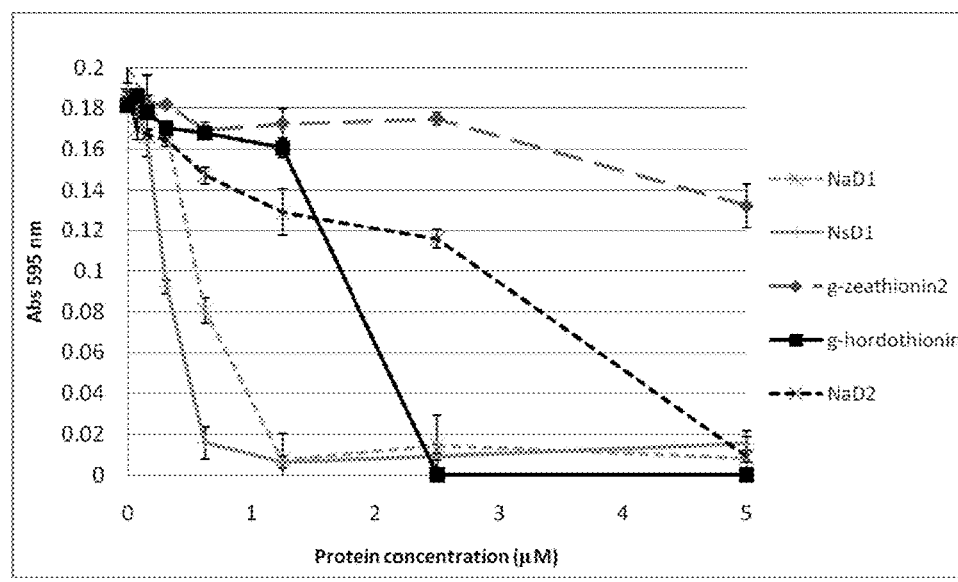

FIG. 7 is a graphical representation of the anti-fungal activity against *Fusarium graminearum* of Class I defensins used for the loop swaps compared to NaD1 and NsD1.

Figure 8:
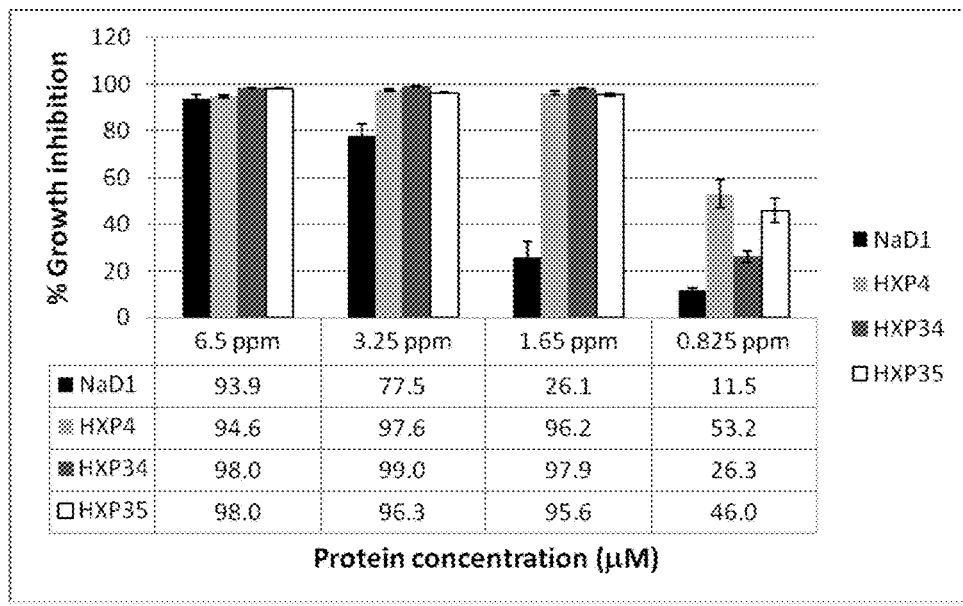

FIG. 8 is a graphical representation of the relative antifungal activity of loop variants HXP4, HXP34 and HXP35 compared to NaD1 against *F. graminearum* (Fgr).

Figure 9:
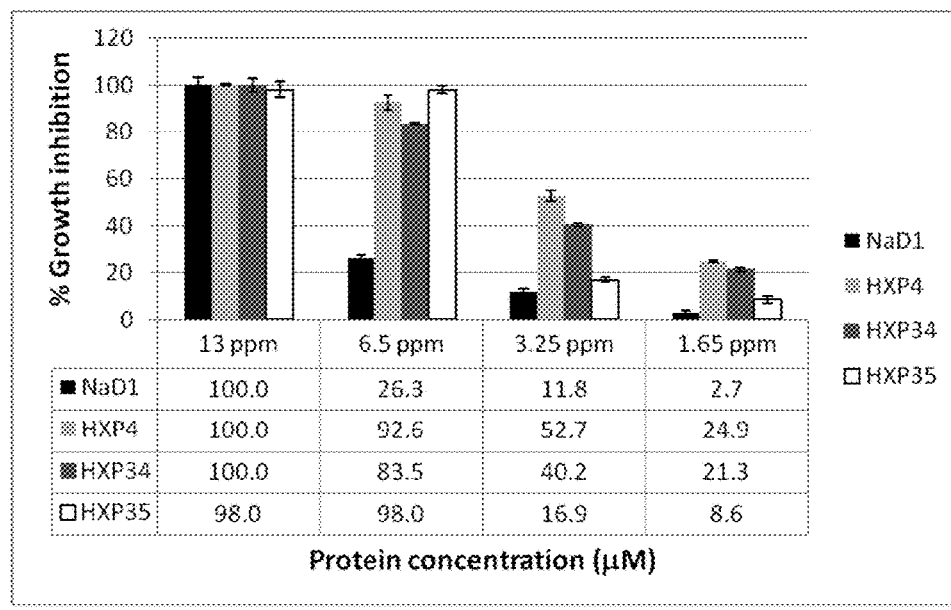

FIG. 9 is a graphical representation of the relative anti-fungal activity of loop variants HXP4, HXP34 and HXP35 compared to NaD1 against *F. verticilloides* (Fve).

Figure 10:
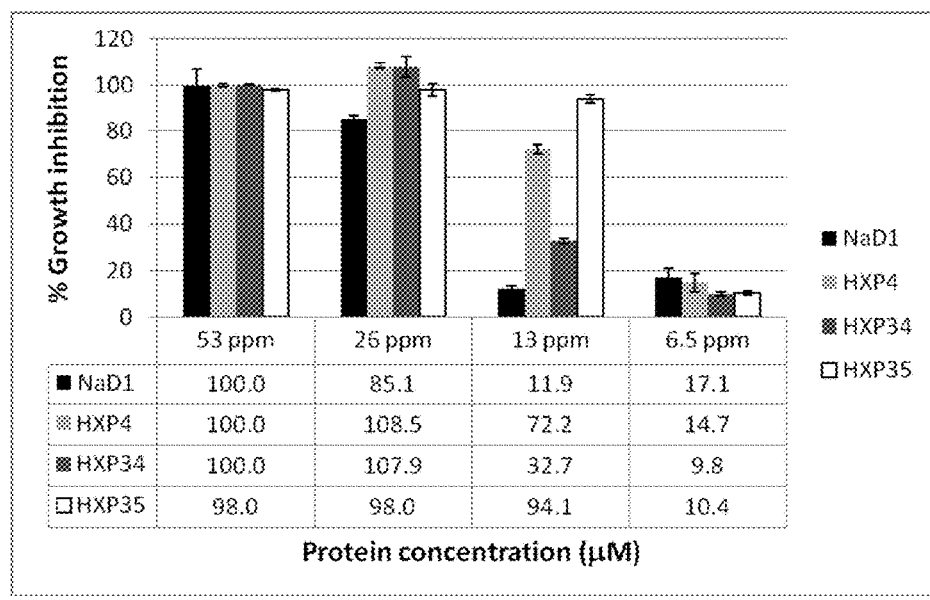

FIG. 10 is a graphical representation of the relative anti-fungal activity of loop variants HXP4, HXP34 and HXP35 compared to NaD1 against *C. graminicola* (Cgr).

FIG. 11 is a diagrammatic representation of pHEX138 construct. The DNA was inserted between the left and right borders of the binary vector pBIN19 (Bevan (1984) *Nucleic Acids Research* 12:8711-8721). The DNA was produced by modifying the NaD1 gene.

Abbreviations in clockwise order are:

oriV: origin of vegetative replication

ColE1 orl: replication origin derived from colicin E1;

TDNA RB: right border of *Agrobacterium tumefaciens* TDNA;

Nos promoter: promoter of nopaline synthase Nos gene;

NPTII: genetic sequence encoding neomycin phosphotransferase II;

Nos terminator: terminator sequence of Nos gene;

Disrupted lacZ: DNA segment encoding partial sequence of B-galactosidase;

CaMV 35S promoter: promoter of Cauliflower mosaic virus (CaMV) 35S protein;

HXP4: DNA encoding NaD2 Loop 1B [NaD2L1B] in NaD1 plus the CTPP;

CaMV 35S terminator: terminator sequence of genes encoding CaMV 35S protein;

M13 on: origin of M13 virus replication;

TDNA LB: TDNA left border;

All arrows indicate direction of transcription.

FIG. 12 is a graphical representation of the relative anti-fungal activity of the loop variant HXP4 compared to NaD1 against *Aspergillus niger.*

FIGS. 13A through C are graphical representations of the relative anti-fungal activity of HXP4 compared to NaD1 against *Cryptococcus* spp.

FIG. 14A through C are graphical representations of the effects of HXP4 on germination (24 hours, A), appresorium (24 hours, B) and post-appresorium structure (48 hours, C) on Asian soybean rust (*Phakopsora pachyrhizi*) compared to NaD1.

FIG. 15 is a representation of the nucleotide sequences (SEQ ID NO:80) of a construct comprising a nucleotide sequence encoding HvCPI6 (a barley cystatin) for use in corn. The amino acid sequence of HvCPI6 (SEQ ID NO:81) is also provided.

FIG. 16 is a representation of the nucleotide sequence (SEQ ID NO:82) of a construct comprising a nucleotide sequence encoding HvCPI6 (a barley cystatin) and the modified defensin HXP4 for use in corn. The amino acid sequence of HvCPI6 and HXP4 (SEQ ID NO:83) is also given.

DETAILED DESCRIPTION

A modified defensin molecule is provided with antipathogen activity. The terms "modified defensin", "variant defensin", "mutated defensin" and "chimeric defensin" may all be used to describe the modified class II solanaceous defensins herein described. In an embodiment, a Class II solanaceous defensin is modified at the loop region between the first β-strand (β-strand 1) and the α-helix at the N-terminal end portion of the defensin. In an embodiment, the loop region comprises the 6 amino acids N-terminal of the second invariant cysteine residue or its equivalent. This region is defined as "Loop 1B" (see FIG. 5). A Class II solanaceous defensin is distinguished from other defensins by a relatively conserved C-terminal end portion of the mature domain. Reference to a "Class II solanaceous defensin" includes any defensin having at least 70% amino acid sequence similarity to the C-terminal end portion of the NaD1 mature domain, the C-terminal portion of NaD1 comprising approximately 20 contiguous amino acid residues ending and including the most C-terminal invariant cysteine in the NaD1 mature domain (for example, SEQ ID NO:52). By "at least 70%" means at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%. Table 4 provides the percentage identities between the C-terminal amino acid sequence of NaD1 and a number of Class II solanaceous defensins mature domains.

The Loop 1B amino acid sequence in a Class II solanaceous defensin is modified to the sequence $X_1 X_2 X_3 X_4 X_5 X_6$ (SEQ ID NO:1) wherein:
  $X_1$ is A, R, N, D, C, Q, E, G, H, I, L, K, M, F, P, S, T, W, Y or V or a naturally occurring modified form thereof;
  $X_2$ is A, R, N, D, C, Q, E, G, H, I, L, K, M, F, P, S, T, W, Y or V or a naturally occurring modified form thereof;
  $X_3$ is A, R, N, D, C, Q, E, G, H, I, L, K, M, F, P, S, T, W, Y or V or a naturally occurring modified form thereof;
  $X_4$ is A, R, N, D, C, Q, E, G, H, I, L, K, M, F, P, S, T, W, Y or V or a naturally occurring modified form thereof;
  $X_5$ is A, R, N, D, C, Q, E, G, H, I, L, K, M, F, P, S, T, W, Y or V or a naturally occurring modified form thereof; and/or
  $X_6$ is A, R, N, D, C, Q, E, G, H, I, L, K, M, F, P, S, T, W, Y or V;
using single letter amino acid nomenclature, wherein the amino acid sequence $X_1 X_2 X_3 X_4 X_5 X_6$ does not correspond to an amino acid sequence of the Loop 1B region from the Class II solanaceous defensin prior to modification.

In an embodiment, the Loop 1B sequence in a Class II solanaceous defensin is modified to the sequence $X_1 X_2 X_3 X_4 X_5 X_6$ (SEQ ID NO:86) wherein:
  $X_1$ is N, G, D, H, K, A, E, Q, T, P, L, M, S, or R;
  $X_2$ is K, R, G, H, L, N, F, I, S, T or Y;
  $X_3$ is W, Y, H, L, G, F or P;
  $X_4$ is P, K, S, R, H, T, E, V, N, Q, D or G;
  $X_5$ is S, K, Y, F, G or H; and/or
  $X_6$ is P, V, L, T, A, F, N, K, R, M, G, H, I or Y;
wherein the amino acid sequence $X_1 X_2 X_3 X_4 X_5 X_6$ does not correspond to an amino acid sequence of the Loop 1B region from the Class II solanaceous defensin prior to modification.

In an embodiment, the Loop 1B sequence in a Class II solanaceous defensin is modified to the sequence $X_1 X_2 X_3 X_4 X_5 X_6$ (SEQ ID NO:55) wherein:
  $X_1$ is N, H, Q, D, K or E;
  $X_2$ is R, H, T, K or G;
  $X_3$ is F, H, Y or W;
  $X_4$ is P, K, S or R;
  $X_5$ is G or F; and
  $X_6$ is P, V, I or N;
wherein the amino acid sequence $X_1 X_2 X_3 X_4 X_5 X_6$ does not correspond to an amino acid sequence of the Loop 1B region from the Class II solanaceous defensin prior to modification.

Reference to "$X_1 X_2 X_3 X_4 X_5 X_6$" means 6 contiguous amino acid residues corresponding to a Loop 1B region.

In an embodiment, the artificially created or modified defensin comprises the amino acid sequence as set forth in SEQ ID NO:57. In this sequence, the Loop 1B region is defined as $X_1 X_2 X_3 X_4 X_5 X_6$ wherein:
  $X_1$ is an amino acid selected from the list consisting of: L, F, S, I, A, H, Y, Q, D, K, G;
  $X_2$ is an amino acid selected from the list consisting of: S, V, F, I, K, L, A, P, N, T, R, H, G;
  $X_3$ is an amino acid selected from the list consisting of: A, F, W, N, I, S, Y, P, L, H;
  $X_4$ is an amino acid selected from the list consisting of: K, G, E, R, A, P, F, Q, V, S;
  $X_5$ is an amino acid selected from the list consisting of: M, G, K, D, S, Y, P, E, N, F; and
  $X_6$ is an amino acid selected from the list consisting of: V, T, M, S, W, A, P, G, E, K, L, H, I, N.

In an embodiment, the artificially created or modified defensin comprises the amino acid sequence as set forth in SEQ ID NO:84. In this sequence, the Loop 1B region is defined as $X_1 X_2 X_3 X_4 X_5 X_6$ wherein:
  $X_1$ is an amino acid selected from the list consisting of: N, H, Q, d, K, E;
  $X_2$ is an amino acid selected from the list consisting of: R, H, T, K, G;
  $X_3$ is an amino acid selected from the list consisting of: F, H, Y W;
  $X_4$ is an amino acid selected from the list consisting of: P, K, S, R;
  $X_5$ is an amino acid selected from the list consisting of: G, F; and
  $X_6$ is an amino acid selected from the list consisting of: P, V, I, N.

In the case of NaD1, a Class II solanaceous defensin, the Loop 1B amino acid sequence is NTFPGI (SEQ ID NO:12). Consequently, the NTFPGI is modified such that N is replaced by one of $X_1$ is A, R, D, C, Q, E, G, H, I, L, K, M, F, P, S, T, W, Y or V or a naturally occurring modified form thereof; the T is replaced by $X_2$ is A, R, N, D, C, Q, E, G, H, I, L, K, M, F, P, S, W, Y or V or a naturally occurring modified form thereof; the F is replaced by $X_3$ is A, R, N, D, C, Q, E, G, H, I, L, K, M, P, S, T, W, Y or V or a naturally occurring modified form thereof; the P is replaced by $X_4$ is A, R, N, D, C, Q, E, G, H, I, L, K, M, F, S, T, W, Y or V or a naturally occurring modified form thereof; the G is replaced by $X_5$ is A, R, N, D, C, Q, E, H, I, L, K, M, F, P, S, T, W, Y or V or a naturally occurring modified form thereof; and/or the I is replaced by $X_6$ is A, R, N, D, C, Q, E, G, H, L, K, M, F, P, S, T, W, Y or V; with the proviso that the Loop 1B amino acid sequence does not correspond to the Loop 1B from NaD1. In an embodiment, the Loop 1B region is defined as $X_1 X_2 X_3 X_4 X_5 X_6$ (SEQ ID NO:56) wherein $X_1$ is an amino acid selected from the list consisting of: L, F, S, I, A, H, Y, Q, D, K, G; $X_2$ is an amino acid selected from the list consisting of: S, V, F, I, K, L, A, P, N, T, R, H, G; $X_3$ is an amino acid selected from the list consisting of: A, F, W, N, I, S, Y, P, L, H; $X_4$ is an amino acid selected from the list consisting of: K, G, E, R, A, P, F, Q, V, S; $X_5$ is an amino acid selected from the list consisting of: M, G, K, D, S, Y, P, E, N, F; and $X_6$ is an amino acid selected from the list consisting of: V, T, M, S, W, A, P, G, E, K, L, H, I, N. The Loop 1B sequence may have a single amino acid change or 2 or 3 or 4 or 5 or all 6 amino acids may be altered. This is encompassed by the expression "single or multiple amino acid substitutions, additions and/or deletions".

The Class II solanaceous defensin may be modified by any number of amino acid changes to the Loop 1B region alone or in combination with other mutations. Other mutations include amino acid substitutions, additions and/or deletions. Mutations outside the Loop 1B region may number from 1 to about 50. A "change" includes a graft of a Loop 1B region from one defensin onto a Class II solanaceous defensin Loop 1B region. The source may be a Class I defensin Loop 1B or a Loop 1B from another Class II defensin. These aspects are based on the proviso that anti-pathogen activity of the modified defensin against at least one plant or animal pathogen is maintained. In an embodiment, the anti-pathogen activity is enhanced relative to the Class II defensin prior to modification in terms of level or spectrum of activity, stability and/or permeabilization.

Provided herein is an artificially created defensin comprising a modified Class II solanaceous defensin backbone wherein the loop region between β-strand 1 and the α-helix on the N-terminal end portion is modified by a single or multiple amino acid substitution, addition and/or deletion to generate a variant defensin which has anti-pathogen activity. In an embodiment, the loop region is Loop 1B defined by the 6 amino acid residues N-terminal to the second invariant cysteine residue. Reference may be made to FIGS. 3 to 5. Its equivalent region in any defensin is contemplated herein. From 1 to about 6 amino acid changes may be made to the Loop 1B region. In an embodiment, the anti-pathogen activity is anti-fungal or anti-insect activity. In an embodiment, anti-pathogen activity is enhanced in the modified Class II solanaceous defensins with respect to inter alia one or more of level and/or spectrum of activity, stability and/or membrane permeabilization capacity compared to Class II solanaceous defensin prior to modification.

Another aspect taught herein provides an artificially created defensin comprising a backbone amino acid sequence from a Class II solanaceous defensin having a Loop 1B region N-terminal to the second invariant cysteine residue wherein the Loop 1B region is modified by an amino acid substitution, addition and/or deletion to generate a defensin which has anti-pathogen activity.

A "single or multiple amino acid substitution, addition and/or deletion" is encompassed by the expression "an amino acid substitution, addition and/or deletion". The artificially created defensin represents a new family of defensins. It is taught herein that the modified defensins be used in horticulture and/or agriculture to control pathogen infestation and growth and as medicaments for use in animals or humans. The modified defensins may be used alone or in combination with a chemical pathogenicide, a proteinaceous anti-pathogen agent and/or a serine or cysteine proteinase inhibitor or a precursor form thereof. The ability to select from a panel of defensins helps combat the development of pathogen resistance to a defensin.

When used in combination with a proteinase inhibitor or anti-pathogen agent, these may be separately topically applied or one expressed in a genetically modified plant and another topically applied or all of the modified defensin and proteinase inhibitor and/or anti-pathogen agent expressed on a single or multiple genetic constructs.

By "Loop 1B" is meant the 6 amino acid residues N-terminal of the second invariant cysteine residue or its equivalent as depicted in FIG. 5. Some defensins such as VrD1 and NeThio1 only have five amino acid residues. However, in that case, the Loop 1B region comprises the five residues. It is also be described as the first flexible loop region between β-strand 1 and the α-helix. Loop 1A (see FIG. 5) is the β-strand.

Figure 1:
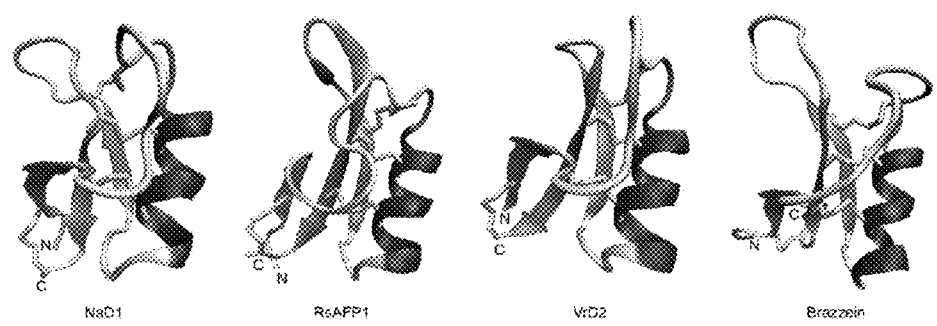
FIG. 1 is a schematic representation of the defensins, NaD1, RsAFP1, VrD2 and Brazzein showing common disulfide bonding pattern and common structural fold in which a triple-stranded, anti-parallel β-sheet is tethered to an α-helix by three disulfide bonds, forming a cysteine-stabilized αβ motif (CSαβ). A fourth disulfide bond also joins the N- and C-termini leading to a stable structure.
Figure 2:
FIG. 2 is a diagrammatic representation showing breakdown of defensins into 16 groups based on sequence similarity.

As indicated above, reference to "an amino acid substitution, addition and/or deletion" includes a single or multiple amino acid substitution, addition and/or deletion which encompasses a replacement of a Loop 1B with a Loop 1B from another defensin. Such a replacement is referred to herein as a domain swap, loop swap, grafting or other similar expression. Reference to "another defensin" includes any defensin whether a Class I or Class II defensin (see also FIG. 2). The Class II defensin backbone is optionally further modified by modified by removal of a C-terminal tail (i.e. the CTPP) or by swapping an existing CTPP with another tail and/or the backbone may have a single or multiple amino acid substitution, addition and/or deletion at a location on the backbone outside the loop region referred to above. A "Class II solanaceous defensin" includes any defensin having at least 70% similarity to SEQ ID NO:52 after optimal alignment. SEQ ID NO:52 represents the 20 contiguous amino acid residues ending at and including the most C-terminal cysteine residue in the NaD1 mature domain. Examples of such Class II solanaceous defensins having at least 70% similarity to SEQ ID NO:52 are listed in Table 4.

Hence, taught herein is a modified defensin comprising a Class II solanaceous defensin back bone having an amino acid substitution, addition and/or deletion to its Loop 1B region to generate a modified defensin which has anti-pathogen activity. In an embodiment, the anti-pathogen activity is enhanced relative to the Class II defensin prior to modification.

In an embodiment, a modified defensin is provided comprising a Class II solanaceous defensin back bone having an amino acid substitution, addition and/or deletion to its Loop 1B region to generate a modified defensin which has anti-pathogen activity, the Class II solanaceous defensin comprising an amino acid sequence at its C-terminal end region of its mature domain having at least 70% similarity to SEQ ID NO:52 after optimal alignment.

In an embodiment, an isolated solanaceous Class II defensin having anti-pathogen activity is taught herein comprising an amino acid sequence as set forth in SEQ ID NO:39 or an amino acid sequence having at least 70% similarity to SEQ ID NO:39, the modification being an amino acid substitution, addition or deletion to a Loop 1B amino acid sequence in the Class II solanaceous defensin. In an embodiment, the anti-pathogen activity is anti-fungal activity.

Also taught herein is an artificially modified solanaceous Class II defensin having anti-pathogen activity comprising an amino acid sequence as set forth in SEQ ID NO:57 or an amino acid sequence having at least 70% similarity to SEQ ID NO:57 after optimal alignment, the modification being to the solanaceous Class II defensin Loop 1B region.

In an embodiment, taught herein is an artificially modified solanaceous Class II defensin having anti-pathogen activity comprising an amino acid sequence as set forth in SEQ ID NO:84 or an amino acid sequence having at least 70% similarity to SEQ ID NO:84 after optimal alignment, the modification being to the solanaceous Class II defensin Loop 1B region.

Reference to "at least 70% similarity" includes 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100% similarity. In an embodiment, this may be referred to as identity.

The present disclosure further provides an artificially created defensin comprising a backbone amino acid sequence from a Class II solanaceous defensin having a loop region between the first β-strand (β-strand 1) and the α-helix on the N-terminal end portion of the Class II solanaceous defensin, the defensin selected from the list consisting of NaD1, NsD1, NsD2, PhD1, PhD2, TPP3, FST, NeThio1, NeThio2, NpThio1, Na-gth, Cc-gth, C20 and SL549 wherein the Loop 1B region is modified by an amino acid substitution, addition and/or deletion to generate a region comprising the amino acid sequence $X_1$ $X_2$ $X_3$ $X_4$ $X_5$ $X_6$ (SEQ ID NO:1) each of $X_1$ through $X_6$ is an amino acid residue and wherein $X_1$ is A, R, N, D, C, Q, E, G, H, I, L, K, M, F, P, S, T, W, Y or V or a naturally occurring modified form thereof; $X_2$ is A, R, N, D, C, Q, E, G, H, I, L, K, M, F, P, S, T, W, Y or V or a naturally occurring modified form thereof; $X_3$ is A, R, N, D, C, Q, E, G, H, I, L, K, M, F, P, S, T, W, Y or V or a naturally occurring modified form thereof; $X_4$ is A, R, N, D, C, Q, E, G, H, I, L, K, M, F, P, S, T, W, Y or V or a naturally occurring modified form thereof; $X_5$ is A, R, N, D, C, Q, E, G, H, I, L, K, M, F, P, S, T, W, Y or V or a naturally occurring modified form thereof; and/or $X_6$ is A, R, N, D, C, Q, E, G, H, I, L, K, M, F, P, S, T, W, Y or V or a naturally occurring modified form thereof; wherein the amino acid sequence $X_1$ $X_2$ $X_3$ $X_4$ $X_5$ $X_6$ does not correspond to an amino acid sequence of the Loop 1B region from the Class II solanaceous defensin prior to modification to thereby generate a defensin which has anti-pathogen activity. In an embodiment, the Loop 1B region is modified by an amino acid substitution, addition and/or deletion to generate a region comprising the amino acid sequence $X_1$ $X_2$ $X_3$ $X_4$ $X_5$ $X_6$ (SEQ ID NO:56) each of $X_1$ through $X_6$ is an amino acid residue and wherein $X_1$ is an amino acid selected from the list consisting of: L, F, S, I, A, H, Y, Q, D, K, G; $X_2$ is an amino acid selected from the list consisting of: S, V, F, I, K, L, A, P, N, T, R, H, G; $X_3$ is an amino acid selected from the list consisting of: A, F, W, N, I, S, Y, P, L, H; $X_4$ is an amino acid selected from the list consisting of: K, G, E, R, A, P, F, Q, V, S; $X_5$ is an amino acid selected from the list consisting of: M, G, K, D, S, Y, P, E, N, F; and $X_6$ is an amino acid selected from the list consisting of: V, T, M, S, W, A, P, G, E, K, L, H, I, N or a naturally occurring modified form thereof; wherein the amino acid sequence $X_1$ $X_2$ $X_3$ $X_4$ $X_5$ $X_6$ does not correspond to an amino acid sequence of the Loop 1B region from the Class II solanaceous defensin prior to modification.

The present disclosure further provides an artificially created defensin comprising a backbone amino acid sequence from a Class II solanaceous defensin having a loop region between the first β-strand (β-strand 1) and the α-helix on the N-terminal end portion of the Class II solanaceous defensin, the defensin selected from the list consisting of NaD1, NsD1, NsD2, PhD1, PhD2, TPP3, FST, NeThio1, NeThio2, NpThio1, Na-gth, Cc-gth, C20 and SL549 wherein the Loop 1B region is modified by an amino acid substitution, addition and/or deletion to generate a region comprising the amino acid sequence $X_1$ $X_2$ $X_3$ $X_4$ $X_5$ $X_6$, (SEQ ID NO:86) wherein each of $X_1$ through $X_6$ is an amino acid residue and $X_1$ is N, G, D, H, K, A, E, Q, T, P, L, M, S, or R; $X_2$ is K, R, G, H, L, N, F, I, S, T or Y; $X_3$ is W, Y, H, L, G, F or P; $X_4$ is P, K, S, R, H, T, E, V, N, Q, D or G; $X_5$ is S, K, Y, F, G or H; and $X_6$ is P, V, L, T, A, F, N, K, R, M, G, H, I or Y; wherein the amino acid sequence $X_1$ $X_2$ $X_3$ $X_4$ $X_5$ $X_6$ does not correspond to an amino acid sequence of the Loop 1B region from the Class II solanaceous defensin prior to modification to thereby generate a defensin which has anti-pathogen activity.

In an embodiment, $X_1$ is N, H, Q, D, K or E; $X_2$ is R, H, T, K or G; $X_3$ is F, H, Y or W; $X_4$ is P, K, S or R; $X_5$ is G or F; and/or $X_6$ is P, V, I or N, wherein the amino acid sequence $X_1$ $X_2$ $X_3$ $X_4$ $X_5$ $X_6$ (SEQ ID NO:55) does not correspond to an amino acid sequence of a Loop 1B region from a Class II solanaceous defensin. Examples of Loop 1B sequences from a Class II solanaceous defensin include NTFPGI from NaD1 (*N. alata*), NsD1 (*N. suaveolens*), NsD2 (*N. suaveolens*), NeThio2 (*N. excelsior*) and FST (*N. tabacum*); PTWDSV from PhD1 (*P. hybrida*); PTWEGI from PhD2 (*P. hybrida*); QTFPGL from TPP3 (*S. lycopersicum*); NTFEGF from Na-gth (*N. attenuata*); NTFPGL from Np-Thio 1 (*N. paniculata*); IFTGL from NeThio1 (*N. excelsior*) and KHFKGL from Cc-gth (*C. chinese*). Another Loop 1B sequence is KYFKGL (SEQ ID NO:60).

Still another aspect taught herein relates to an artificially created defensin comprising a backbone amino acid sequence from a Class II solanaceous defensin having a loop region between β-strand 1 and the α-helix on the N-terminal end portion of the Class II solanaceous defensin, the defensin selected from the list consisting of NaD1, NsD1, NsD2, PhD1, PhD2, TPP3, FST, NeThio1, NeThio2, NpThio1, Na-gth and Cc-gth wherein the loop region on the defensin backbone is replaced with a loop region from a defensin selected from the list consisting of NaD2 (HRFKGP), Zea2 (QHHSFP), PSD1 (DTYRGV), MsDef1 (DKYRGP), SoD2 (KTFKGI) and DmAMP1 (KTWSGN) or a modified form thereof, or a Loop 1B sequence selected from SEQ ID NO:67 to 79 to generate a defensin which has anti-pathogen activity.

In an embodiment, the anti-pathogen activity is enhanced compared to the Class II solanaceous defensin prior to modification. Parameters for determining enhanced activity include level and/or spectrum of activity degree of stability and/or level of permeabilization activity. In an embodiment, the loop region is Loop 1B as herein defined. This is the first flexible loop in a defensin.

As indicated above, the Loop 1B region on the Class II solanaceous defensin comprises the amino acid sequence $X_1$ $X_2$ $X_3$ $X_4$ $X_5$ $X_6$, each X as hereinbefore defined, wherein at least one or more including in an aspect all 6 (or corresponding 5) amino acid residues is/are replaced, generally but not exclusively, to the sequence corresponding to a Loop 1B or a derivative thereof from another defensin such as a Class I defensin or another Class II defensin.

Also provided is a modified defensin having anti-pathogen activity the modified defensin comprising:

(i) a backbone amino acid sequence derived from a Class II solanaceous defensin, the defensin comprising a Loop 1B region between β-strand 1 and the α-helix on the N-terminal end portion of the defensin;

(ii) the Loop 1B region on the defensin modified by an amino acid substitution, addition, deletion or swap to generate a Loop 1B region analogous or homologous or otherwise functionally similar to another defensin Loop 1B;

(iii) wherein the resulting Loop 1B comprises the amino acid sequence $X_1$ $X_2$ $X_3$ $X_4$ $X_5$ $X_6$ (SEQ ID NO:1) wherein:

$X_1$ is A, R, N, D, C, Q, E, G, H, I, L, K, M, F, P, S, T, W, Y or V or a naturally occurring modified form thereof;

$X_2$ is A, R, N, D, C, Q, E, G, H, I, L, K, M, F, P, S, T, W, Y or V or a naturally occurring modified form thereof;

$X_3$ is A, R, N, D, C, Q, E, G, H, I, L, K, M, F, P, S, T, W, Y or V or a naturally occurring modified form thereof;

$X_4$ is A, R, N, D, C, Q, E, G, H, I, L, K, M, F, P, S, T, W, Y or V or a naturally occurring modified form thereof;

$X_5$ is A, R, N, D, C, Q, E, G, H, I, L, K, M, F, P, S, T, W, Y or V; or a naturally occurring modified form thereof and/or $X_6$ is A, R, N, D, C, Q, E, G, H, I, L, K, M, F, P, S, T, W, Y or V or a naturally occurring modified form thereof, using single letter amino acid nomenclature, wherein the amino acid sequence $X_1 X_2 X_3 X_4 X_5 X_6$ does not correspond to an amino acid sequence of the Loop 1B region from the Class II solanaceous defensin prior to modification.

Also provide is a modified defensin having anti-pathogen activity the modified defensin comprising:

(i) a backbone amino acid sequence derived from a Class II solanaceous defensin, the defensin comprising a Loop 1B region between β-strand 1 and the α-helix on the N-terminal end portion of the defensin;

(ii) the Loop 1B region on the defensin modified by an amino acid substitution, addition, deletion or swap to generate a Loop 1B region analogous or homologous or otherwise functionally similar to another defensin Loop 1B;

(iii) wherein the resulting Loop 1B comprises the amino acid sequence $X_1 X_2 X_3 X_4 X_5 X_6$ (SEQ ID NO:86) wherein:

$X_1$ is N, G, D, H, K, A, E, Q, T, P, L, M, S, or R;
$X_2$ is K, R, G, H, L, N, F, I, S, T or Y;
$X_3$ is W, Y, H, L, G, F or P;
$X_4$ is P, K, S, R, H, T, E, V, N, Q, D or G;
$X_5$ is S, K, Y, F, G or H; and/or
$X_6$ is P, V, L, T, A, F, N, K, R, M, G, H, I or Y, wherein the amino acid sequence $X_1 X_2 X_3 X_4 X_5 X_6$ does not correspond to an amino acid sequence of the Loop 1B region from the Class II solanaceous defensin prior to modification.

The backbone amino acid sequence may further comprise an amino acid substitution, addition and/or deletion to a region outside the Loop 1B region. If present, from about 1 to about 50 amino acid substitutions, additions and/or deletions may be made to the backbone amino acid sequence outside the Loop 1B region. By "1 to 50" means 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In an embodiment, the additional mutation is in the C-terminal tail (the CTPP) of the Type II solanaceous defensin.

Also provided is a modified defensin comprising a backbone defensin molecule from *Nicotiana suaveolens* (an Australian native) having a Loop 1B region or its equivalent modified by an amino acid substitution, addition and/or deletion to introduce a Loop 1B sequence comprising $X_1 X_2 X_3 X_4 X_5 X_6$ (SEQ ID NO:1) wherein:

$X_1$ is A, R, N, D, C, Q, E, G, H, I, L, K, M, F, P, S, T, W, Y or V or a naturally occurring modified form thereof;

$X_2$ is A, R, N, D, C, Q, E, G, H, I, L, K, M, F, P, S, T, W, Y or V or a naturally occurring modified form thereof;

$X_3$ is A, R, N, D, C, Q, E, G, H, I, L, K, M, F, P, S, T, W, Y or V or a naturally occurring modified form thereof;

$X_4$ is A, R, N, D, C, Q, E, G, H, I, L, K, M, F, P, S, T, W, Y or V or a naturally occurring modified form thereof;

$X_5$ is A, R, N, D, C, Q, E, G, H, I, L, K, M, F, P, S, T, W, Y or V or a naturally occurring modified form thereof; and/or $X_6$ is A, R, N, D, C, Q, E, G, H, I, L, K, M, F, P, S, T, W, Y or V or a naturally occurring modified form thereof, using single letter amino acid nomenclature, wherein the amino acid sequence $X_1 X_2 X_3 X_4 X_5 X_6$ does not correspond to an amino acid sequence of the Loop 1B region from the Class II solanaceous defensin prior to modification and wherein the modified defensin has anti-pathogen activity. In an embodiment, the *N. suaveolens* defensin is selected from NsD1 and NsD2.

Another embodiment provided herein comprises a modified defensin comprising a backbone defensin molecule from *Nicotiana suaveolens* (an Australian native) having a Loop 1B region or its equivalent modified by a single or multiple amino acid substitution, addition and/or deletion to introduce a Loop 1B sequence comprising $X_1 X_2 X_3 X_4 X_5 X_6$ (SEQ ID NO:86) wherein:

$X_1$ is N, G, D, H, K, A, E, Q, T, P, L, M, S, or R;
$X_2$ is K, R, G, H, L, N, F, I, S, T or Y;
$X_3$ is W, Y, H, L, G, F or P;
$X_4$ is P, K, S, R, H, T, E, V, N, Q, D or G;
$X_5$ is S, K, Y, F, G or H; and/or
$X_6$ is P, V, L, T, A, F, N, K, R, M, G, H, I or Y, wherein the amino acid sequence $X_1 X_2 X_3 X_4 X_5 X_6$ does not correspond to an amino acid sequence of the Loop 1B region from the Class II solanaceous defensin prior to modification and wherein the modified defensin has anti-pathogen activity. In an embodiment, the *N. suaveolens* defensin is selected from NsD1 and NsD2.

In an embodiment, $X_1 X_2 X_3 X_4 X_5 X_6$ (SEQ ID NO:56) comprises an amino acid residue selected from:

$X_1$ is an amino acid selected from the list consisting of: L, F, S, I, A, H, Y, Q, D, K, G;

$X_2$ is an amino acid selected from the list consisting of: S, V, F, I, K, L, A, P, N, T, R, H, G;

$X_3$ is an amino acid selected from the list consisting of: A, F, W, N, I, S, Y, P, L, H;

$X_4$ is an amino acid selected from the list consisting of: K, G, E, R, A, P, F, Q, V, S;

$X_5$ is an amino acid selected from the list consisting of: M, G, K, D, S, Y, P, E, N, F; and $X_6$ is an amino acid selected from the list consisting of: V, T, M, S, W, A, P, G, E, K, L, H, I, N.

In this regard, the present disclosure further provides an isolated defensin from *Nicotiana suaveolens* having an amino acid sequence as set forth in SEQ ID NO:49 [NsD1] or an amino acid sequence having at least 70% thereto after optimal alignment. Another aspect of the present disclosure is directed to an isolated defensin from *Nicotiana suaveolens* having an amino acid sequence as set forth in SEQ ID NO:51 [NsD2] or an amino acid sequence having at least 70% thereto after optimal alignment. Nucleotide sequences encoding NsD1 and NsD2 such as SEQ ID NO:48 or SEQ ID NO:50, respectively, or a nucleotide sequence having at least 70% identity to SEQ ID NO:48 or SEQ ID NO:50 after optimal alignment or which is capable of hybridizing to SEQ ID NO:48 or SEQ ID NO:50 or a complementary form of SEQ ID NO:48 or SEQ ID NO:50 under medium stringency conditions are also contemplated herein. By "at least 70% identity" means at least 70, 71, 72, 73, 74, 75, 76, 77, 78, 79, 80, 81, 82, 83, 84, 85, 86, 87, 88, 89, 90, 91, 92, 93, 94, 95, 96, 97, 988, 99 or 100%. In an aspect, the anti-pathogen activity is enhanced based on spectrum or level of activity, level of stability and/or ability to induce permeabilization compared to NsD1 or NsD2 prior to modification.

In an embodiment, the loop region on the Class II defensin is substituted by $X_1 X_2 X_3 X_4 X_5 X_6$ (SEQ ID NO:55) wherein:

$X_1$ is N, H, Q, D, K or E;
$X_2$ is R, H, T, K or G;

$X_3$ is F, H, Y or W;
$X_4$ is P, K, S or R;
$X_5$ is G or F; and/or
$X_6$ is P, V, I or N,
wherein the amino acid sequence $X_1$ $X_2$ $X_3$ $X_4$ $X_5$ $X_6$ does not correspond to an amino acid sequence of the Loop 1B region from the Class II solanaceous defensin prior to modification.

Insofar as the backbone defensin is NaD1, then the Loop 1B may be modified, wherein the modification comprises:

the N is substituted with an amino acid residue selected from A, R, D, C, Q, E, G, H, I, L, K, M, F, P, S, T, W, Y and V or a naturally occurring modified form thereof;

the T is substituted with an amino acid residue selected from A, R, N, D, C, Q, E, G, H, I, L, K, M, F, P, S, W, Y and V or a naturally occurring modified form thereof;

the F is substituted with an amino acid residue selected from A, R, N, D, C, Q, E, G, H, I, L, K, M, P, S, T, W, Y and V or a naturally occurring modified form thereof;

the P is substituted with an amino acid residue selected from A, R, N, D, C, Q, E, G, H, I, L, K, M, F, S, T, W, Y and V or a naturally occurring modified form thereof;

the G is substituted with an amino acid residue selected from A, R, N, D, C, Q, E, H, I, L, K, M, F, P, S, T, W, Y and V or a naturally occurring modified form thereof; and/or the I is substituted by an amino acid residue selected from A, R, N, D, C, Q, E, G, H, L, K, M, F, P, S, T, W, Y and V or a naturally occurring modified form thereof, (See also SEQ ID NO:1)

wherein the amino acid sequence $X_1$ $X_2$ $X_3$ $X_4$ $X_5$ $X_6$ does not correspond to an amino acid sequence of the Loop 1B region from NaD1.

Insofar as the backbone defensin is NaD1, then the Loop 1B may be modified, wherein the modification comprises one or more of:

the N substituted with an amino acid residue selected from G, D, H, K, A, E, Q, T, P, L, M, S, T and R;

the T substituted with an amino acid residue selected from K, R, G, H, L, N, F, I, S and Y;

the F substituted with an amino acid residue selected from W, Y, H, L, G and P;

the P substituted with an amino acid residue selected from K, S, R, H, T, E, V, N, Q, D or G;

the G substituted with an amino acid residue selected from S, K, Y, F and H; and/or the I substituted by an amino acid residue selected from P, V, L, T, A, F, N, K, R, M, G, H and Y. See also SEQ ID NO:87.

In an embodiment, $X_1$ $X_2$ $X_3$ $X_4$ $X_5$ $X_6$ comprises an amino acid residue selected from:

$X_1$ is an amino acid selected from the list consisting of: L, F, S, I, A, H, Y, Q, D, K, G;

$X_2$ is an amino acid selected from the list consisting of: S, V, F, I, K, L, A, P, N, T, R, H, G;

$X_3$ is an amino acid selected from the list consisting of: A, F, W, N, I, S, Y, P, L, H;

$X_4$ is an amino acid selected from the list consisting of: K, G, E, R, A, P, F, Q, V, S;

$X_5$ is an amino acid selected from the list consisting of: M, G, K, D, S, Y, P, E, N, F; and $X_6$ is an amino acid selected from the list consisting of: V, T, M, S, W, A, P, G, E, K, L, H, I, N. See also SEQ ID NO:56.

By "one or more" of $X_1$ through $X_6$ means 1 or 2 or 3 or 4 or 5 or all 6 amino acid residues are modified. A mutation outside the Loop 1B region includes, if present, from 1 to about 50 amino acid substitutions, additions and/or deletions.

Reference to a "pathogen" includes a fungus, microorganism including a bacterium, an insect, an arachnid, a virus and a nematode as well as a protozoan. In an embodiment, the pathogen is a fungus or an insect.

Reference to a "fungus" includes fungi which infect and are otherwise pathogens of plants or animals. Animal fungal pathogens include mammalian including human fungal pathogens. Particular fungal pathogens include *Colletotrichum graminicola, Diplodia maydis, Fusarium graminearum* and *Fusarium verticilloides*. Specific pathogens for the major crops include: Corn: *Gibberella zeae* (*Fusarium graminearum*), *Colletotrichum graminicola, Stenocarpella maydi* (*Diplodia maydis*), *Fusarium moniliforme* var. *subglutinans, Fusarium verticilloides, Bipolaris maydis* O, T (*Cochliobolis heterostrophus*), *Exserohilum turcicum* I, II and III, *Cercospora zeae-maydis, Pythium irregulare, Pythium debaryanum, Pythium graminicola, Pythium splendens, Pythium ultimum, Pythium aphanidermatum, Aspergillus* spp, *Aspergillus flavus, Helminthosporium carbonum* I, II and III (*Cochliobolus carbonum*), *Helminthosporium pedicellatum, Physoderma maydis, Phyllosticta maydis, Kabatiella maydis, Cercospora sorghi, Ustilago maydis, Ustilago zeae, Puccinia sorghi, Puccinia polysora, Macrophomina phaseolina, Penicillium oxalicum, Nigrospora oryzae, Cladosporium herbarium, Curvularia lunata, Curvularia inaequalis, Curvularia pallescens, Trichoderma viride, Claviceps sorghi, Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporum maydis, Cephalosporum acremonium*; Soybeans: *Fusarium virgululiforme, Fusarium solani, Sclerotinia sclerotiorum, Fusarium oxysporum, Fusarium tucumaniae, Phakopsora pachyrhizi, Phytophthora megasperma* f. sp. *glycinea, Phytophthora sojae, Macrophomina phaseolina, Rhizoctonia solani, Sclerotinia sclerotiorum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotrichum truncatum*), *Corynespora cassiicola, Septoria glycines, Phyllosticta sojicola, Alternaria alternata, Microsphaera diffusa, Fusarium semitectum, Phialophora gregata, Glomerella glycines, Pythium aphanidermatum, Pythium ultimum, Pythium debaryanum*; Canola: *Albugo candida, Alternaria brassicae, Leptosphaeria maculans, Rhizoctonia solani, Sclerotinia sclerotiorum, Mycosphaerella brassicicola, Pythium ultimum, Peronospora parasitica, Fusarium oxysporum, Fusarium avenaceum, Fusarium roseum, Alternaria alternata*; Cotton: *Fusarium oxysporum* f. sp. *vasinfectum, Verticillium dahliae, Thielaviopsis basicola, Alternaria macrospora, Cercospora gossypina, Phoma exigua* (*Ascochyta gossypii*), *Pythium* spp *Rhizoctonia solani, Puccinia scheddardii, Puccinia cacabata, Phymatotrichopsis omnivore*; Canola: *Leptosphaeria maculans, Sclerotinia sclerotiorum, Alternaria brassicae, Alternaria brasicicola, Plasmodiophora brassicae, Rhizoctonia solani, Fusarium* spp, *Pythium* spp, *Phytophthora* spp, *Alternaria* spp, *Peronospora parasitica, Mycosphaerella capsellae* (*Pseudocercosporella capsellae*), *Albugo candida, Phytophthora megasperma* var. *megasperma, Botrytis cinerea, Erysiphe cruciferarum*; Wheat: *Cochliobolus sativus, Drechslera wirreganensis, Mycosphaerella graminicola, Phaeosphaeria avenaria* f. sp. *triticea, Phaeosphaeria nodorum, Blumeria graminis* f. sp. *tritici, Urocystis agropyri, Alternaria alternata, Cladosporium herbarum, Fusarium graminearum, Fusarium avenaceum, Fusarium*

*culmorum, Fusarium pseudograminearum, Ustilago tritici, Ascochyta tritici, Cephalosporium gramineum, Colletotrichum graminicola, Erysiphe graminis* f. sp. *tritici, Puccinia graminis* f. sp. *tritici, Puccinia recondita* f. sp. *tritici, Puccinia striiformis, Puccinia triticina, Sclerophthora macrospora, Urocystis agropyri, Pyrenophora tritici-repentis, Pyrenophora semeniperda, Phaeosphaeria nodorum, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium* spp, *Pythium aphanidermatum, Pythium arrhenomannes, Pythium gramicola, Pythium ultimum, Bipolaris sorokiniana, Claviceps purpurea, Tapesia yallundae, Tilletia tritici, Tilletia laevis, Tilletia caries, Tilletia indica, Ustilago tritici, Wojnowicia graminis, Cochliobolus sativus*; Sorghum: *Exserohilum turcicum, Colletotrichum sublineolum, Cercospora sorghi, Gloeocercospora sorghi, Ascochyta sorghina, Puccinia purpurea, Macrophomina phaseolina, Perconia circinata, Fusarium mondiforme, Alternaria alternata, Bipolaris sorghicola, Helminthosporium sorghicola, Curvularia lunata, Phoma insidiosa, Ramulispora sorghi, Ramulispora sorghicola, Phyllachara saccari, Sporisorium reilianum (Sphacelotheca reiliana), Sphacelotheca cruenta, Sporisorium sorghi, Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*; Sunflower: *Plasmopara halstedii, Sclerotinia sclerotiorum, Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthe, Verticillium dahliae, Cephalosporum acremonium, Phytophthora cryptogea, Albugo tragopogonis*; Alfalfa: *Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Verticillium albo-atrum, Aphanomyces euteiches, Stemphylium herbarum, Stemphylium alfalfae, Colletotrichum trifolii, Leptosphaerulina briosiana, Uromyces striatus, Sclerotinia trifoliorum, Stagonospora meliloti, Stemphylium botryosum* and Leptotrichila medicaginis.

In an embodiment, fungal pathogens in corn include *Fusarium graminearum, Colletotrichum graminicola, Stenocarpella maydis, Fusarium verticilloides, Cochliobolis heterostrophus, Exserohilum turcicum, Cercospora zeamaydis.*

In an embodiment, fungal pathogens in soybean include *Fusarium virguliforme, Fusarium solanai, Sclerotinia sclerotiorum, Fusarium oxysporum, Fusarium tucumaniae, Phakopsora pachirhizi.*

Animal including mammalian and in particular human fungal pathogens include species of *Alternaeria* spp, *Aspergillus* spp, *Candida* spp, *Fusarium* spp, *Trychophyton* spp, *Cryptococcus* spp, *Microsporum* spp, *Penicillium* spp, *Trichosporon* spp, *Scedosporium* spp, *Paeciliomyces* spp, *Acremonium* spp and Dermatiaceous molds. Specific animal, including mammalian and in particular human pathogens include *Alternaria alternata, Aspergillus fumigatus, Aspergillus niger, Aspergillus flavus, Aspergillus nidulans, Aspergillus paraciticus, Candida albicans, Candida dubliniensis, Candida famata, Candida glabrata, Candida guilliermondii, Candida haemulonii, Candida kefyr, Candida krusei, Candida lusitaniae, Candida norvegensis, Candida parapsilosis, Candida tropicalis, Candida viswanathii, Fusarium oxysporum, Fusarium solani, Fusarium monoliforme, Trycophyton rubrum, Trycophyton mentagrophytes, Trycophyton interdigitales, Trycophyton tonsurans, Cryptococcus neoformans, Cryptococcus gattii, Cryptococcus grubii, Microsporum canis, Microsporum gypseum, Penicillium mameffei, Tricosporon beigelii, Trichosporon asahii, Trichosporon inkin, Trichosporon asteroides, Trichosporon cutaneum, Trichosporon domesticum, Trichosporon mucoides, Trichosporon ovoides, Trichosporon pullulans, Trichosporon loubieri, Trichosporon japonicum, Scedosporium apiospermum, Scedosporium prolificans, Paecilomyces variotii, Paecilomyces lilacinus, Acremonium strucutm, Cladophialophora bantiana, Wangiella dermatitidis, Ramichloridium obovoideum, Chaetomium atrobrunneum, Dactlaria gallopavum, Bipolaris* spp, *Exserohilum rostratum* as well as *Absidia corymbifera, Apophysomyces elegans, Mucor indicus, Rhizomucor pusillus, Rhizopus oryzae, Cunninghamella bertholletiae, Cokeromyces recurvatus, Saksenaea vasiformis, Syncephalastrum racemosum, Basidiobolus ranarum, Conidiobolus coronatus/Conidiobolus incongruus, Blastomyces dermatitidis, Coccidioides immitis, Coccidioides posadasii, Histoplasma capsulatum, Paracoccidioides brasiliensis, Pseudallescheria boydii* and *Sporothrix schenckii.*

Reference to a "fungus" also includes oomycetes such as *Pythium* spp and *Phytophthora* spp. The term "fungus" also encompasses a rust.

Bacterial pathogens include *Xanthomonas* spp and *Pseudomonas* spp. Other microorganisms include *Phytoplasma* spp and *Spiroplasma* spp. Other pathogens include viruses, nematodes and protozoa. Insect pathogens include *Diatraea grandiosella, Ostrinia nubialis, Rhopalosiphum* spp, *Helicoverpa* spp, *Plutella xylostella* and *Lygus* spp.

Also provided herein are isolated nucleic acid molecules encoding the modified Class II solanaceous defensin. In an embodiment, the nucleic acid comprises a nucleotide sequence which encodes an amino acid sequence set forth SEQ ID NO:57. In an embodiment, the nucleic acid comprises a nucleotide sequence which encodes an amino acid sequence set forth SEQ ID NO:84.

Hence, an isolated nucleic acid molecule is provided encoding an artificially created defensin comprising:

(i) an amino acid backbone derived from or corresponding to a Class II solanaceous defensin;

(ii) a Loop 1B on the backbone or its equivalent being subjected to one or more of: (a) an amino acid substitution, addition and/or deletion; and/or (b) replacement of all or part by Loop 1B or a modified form thereof from another defensin; and optionally (c) another an amino acid substitution, addition and/or deletion outside the Loop 1B region on the backbone;

wherein the artificially created defensin exhibits anti-pathogen activity Loop 1B.

Another aspect taught herein is an isolated nucleic acid molecule encoding an artificially created defensin comprising a backbone amino acid sequence from a Class II solanaceous defensin having a loop region between β-strand 1 and the α-helix on the N-terminal end portion of the Class II solanaceous defensin wherein the loop region is modified by an amino acid substitution, addition and/or deletion to generate a defensin which has anti-pathogen activity.

In an aspect, the loop region is Loop 1B. Another aspect is directed to an isolated nucleic acid molecule encoding an artificially created defensin comprising a backbone amino acid sequence from a Class II solanaceous defensin having a Loop 1B region between β-strand 1 and the α-helix on the N-terminal end portion of the Class II solanaceous defensin, the defensin selected from the list consisting of NaD1, NsD1, NsD2, PhD1, PhD2, TPP3, FST, NeThio1, NeThio2, NpThio1, Na-gth, Cc-gth, C20 and SL549 wherein the Loop 1B region is modified by an amino acid substitution, addition and/or deletion to generate a region comprising the amino acid sequence $X_1 X_2 X_3 X_4 X_5 X_6$, (SEQ ID NO:86) wherein each of $X_1$ through $X_6$ is an amino acid residue and wherein $X_1$ is N, G, D, H, K, A, E, Q, T, P, L, M, S, or R; $X_2$ is K, R, G, H, L, N, F, I, S, T or Y; $X_3$ is W, Y, H, L, G, F or P; $X_4$ is P, K, S, R, H, T, E, V, N, Q, D or G; $X_5$ is S, K, Y, F, G or H; and/or $X_6$ is P, V, L, T, A, F, N, K, R, M, G, H or Y; wherein the amino acid sequence $X_1 X_2 X_3 X_4 X_5 X_6$ does not correspond to an amino acid sequence of the Loop 1B region from the Class II solanaceous defensin prior to modification to thereby artificially generate a defensin which has anti-pathogen activity. In an embodiment, $X_1 X_2 X_3 X_4 X_5 X_6$ (SEQ ID NO:56) comprises an amino acid residue selected from L, F, S, I, A, H, Y, Q, D, K, G; $X_2$ is an amino acid selected from the list consisting of: S, V, F, I, K, L, A, P, N, T, R, H, G; $X_3$ is an amino acid selected from the list consisting of: A, F, W, N, I, S, Y, P, L, H; $X_4$ is an amino acid selected from the list consisting of: K, G, E, R, A, P, F, Q, V, S; $X_5$ is an amino acid selected from the list consisting of: M, G, K, D, S, Y, P, E, N, F; and $X_6$ is an amino acid selected from the list consisting of: V, T, M, S, W, A, P, G, E, K, L, H, I, N.

Another aspect is directed to an isolated nucleic acid molecule encoding an artificially created defensin comprising a backbone amino acid sequence from a Class II solanaceous defensin having a Loop 1B region between β-strand 1 and the α-helix on the N-terminal end portion of the Class II solanaceous defensin, the defensin having a C-terminal end amino acid sequence of the mature domain with at least 70% similarity to SEQ ID NO:52, wherein the Loop 1B region is modified by an amino acid substitution, addition and/or deletion to generate a region comprising the amino acid sequence $X_1 X_2 X_3 X_4 X_5 X_6$, SEQ ID NO:1, wherein each of $X_1$ through $X_6$ is an amino acid residue and wherein $X_1$ is A, R, N, D, C, Q, E, G, H, I, L, K, M, F, P, S, T, W, Y or V or a naturally occurring modified form thereof; $X_2$ is A, R, N, D, C, Q, E, G, H, I, L, K, M, F, P, S, T, W, Y or V or a naturally occurring modified form thereof; $X_3$ is A, R, N, D, C, Q, E, G, H, I, L, K, M, F, P, S, T, W, Y or V or a naturally occurring modified form thereof; $X_4$ is A, R, N, D, C, Q, E, G, H, I, L, K, M, F, P, S, T, W, Y or V; $X_5$ is A, R, N, D, C, Q, E, G, H, I, L, K, M, F, P, S, T, W, Y or V or a naturally occurring modified form thereof; and/or $X_6$ is A, R, N, D, C, Q, E, G, H, I, L, K, M, F, P, S, T, W, Y or V or a naturally occurring modified form thereof; wherein the amino acid sequence $X_1 X_2 X_3 X_4 X_5 X_6$ does not correspond to an amino acid sequence of the Loop 1B region from the Class II solanaceous defensin prior to modification, to thereby artificially generate a defensin which has anti-pathogen activity.

Another aspect is an isolated nucleic acid molecule encoding an artificially created defensin having a backbone amino acid sequence derived from a *Nicotiana suaveolens* defensin with a Loop 1B region or its equivalent modified by a single or multiple amino acid substitution, addition and/or deletion to generate a region comprising the amino acid sequence $X_1 X_2 X_3 X_4 X_5 X_6$, SEQ ID NO:1, wherein each of $X_1$ through $X_6$ is an amino acid residue and $X_1$ is A, R, N, D, C, Q, E, G, H, I, L, K, M, F, P, S, T, W, Y or V or a naturally occurring modified form thereof; $X_2$ is A, R, N, D, C, Q, E, G, H, I, L, K, M, F, P, S, T, W, Y or V or a naturally occurring modified form thereof; $X_3$ is A, R, N, D, C, Q, E, G, H, I, L, K, M, F, P, S, T, W, Y or V or a naturally occurring modified form thereof; $X_4$ is A, R, N, D, C, Q, E, G, H, I, L, K, M, F, P, S, T, W, Y or V or a naturally occurring modified form thereof; $X_5$ is A, R, N, D, C, Q, E, G, H, I, L, K, M, F, P, S, T, W, Y or V or a naturally occurring modified form thereof; and/or $X_6$ is A, R, N, D, C, Q, E, G, H, I, L, K, M, F, P, S, T, W, Y or V or a naturally occurring modified form thereof; wherein the amino acid sequence $X_1 X_2 X_3 X_4 X_5 X_6$ does not correspond to an amino acid sequence of the Loop 1B region from the Class II solanaceous defensin prior to modification to artificially generate a defensin which has anti-pathogen activity. Examples of defensins for *N. suaveolens* include NsD1 and NsD2.

Still another aspect provides an isolated nucleic acid molecule encoding an artificially created defensin having a backbone amino acid sequence derived from a *Nicotiana suaveolens* defensin with a Loop 1B region or its equivalent modified by a single or multiple amino acid substitution, addition and/or deletion to generate a region comprising the amino acid sequence $X_1 X_2 X_3 X_4 X_5 X_6$, SEQ ID NO:86, wherein each of $X_1$ through $X_6$ is an amino acid residue and $X_1$ is N, G, D, H, K, A, E, Q, T, P, L, M, S, or R; $X_2$ is K, R, G, H, L, N, F, I, S, T or Y; $X_3$ is W, Y, H, L, G, F or P; $X_4$ is P, K, S, R, H, T, E, V, N, Q, D or G; $X_5$ is S, K, Y, F, G or H; and/or $X_6$ is P, V, L, T, A, F, N, K, R, M, G, H, I or Y; wherein the amino acid sequence $X_1 X_2 X_3 X_4 X_5 X_6$ does not correspond to an amino acid sequence of the Loop 1B region from the Class II solanaceous defensin prior to modification to artificially generate a defensin which has anti-pathogen activity. Examples of defensins for *N. suaveolens* include NsD1 and NsD2.

In yet another embodiment, the isolated nucleic acid molecule encodes an artificially created defensin comprising a backbone amino acid sequence from a Class II solanaceous defensin having a Loop 1B region between β-strand 1 and the α-helix on the N-terminal end portion of the solanaceous defensin, the defensin selected from the list consisting of NaD1, NsD1, NsD2, PhD1, PhD2, TPP3, FST, NeThio1, NeThio2, NpThio1, Na-gth, Cc-gth, C20 and SL549 wherein the Loop 1B region on the Class II solanaceous defensin backbone is replaced with a Loop 1B region from a defensin selected from the list consisting of NaD2 (SEQ ID NO:29)(HRFKGP), Zea2 (SEQ ID NO:30)(QHHSFP), PsD1 (SEQ ID NO:31)(DTYRGV)), MsDef1 (SEQ ID NO:33)(DKYRGP), SoD2 (SEQ ID NO:34)(KTFKGI) and DmAMP1 (SEQ ID NO:35)(KTWSGN) or a Loop 1B sequence selected from SEQ ID NO:67 to 79 to generate a defensin which has anti-pathogen activity.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (1997) *Nucl. Acids. Res.* 25: 3389). A detailed discussion of sequence analysis can be found in Unit 19.3 of Ausubel et al. (1998) In: *Current Protocols in Molecular Biology, John Wiley & Sons Inc.* 1994-1998.

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present disclosure, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity. By "at least 70%" means 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100%.

The instant disclosure extends to nucleic acid molecules which hybridize under low stringency conditions to the nucleic acid molecule encoding the modified defensin.

Stringency conditions can be defined by, for example, the concentrations of salt or formamide in the pre-hybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the present disclosure are defined by their ability to hybridize under various stringency conditions (e.g. high, medium, and low).

Reference herein to a "low stringency" includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as "medium stringency", which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or "high stringency", which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C) % (Marmur and Doty (1962) *J Mol Biol* 5:109-118). However, the $T_m$ of a duplex nucleic acid molecule decreases by 1° C. with every increase of 1% in the number of mismatch base pairs (Bonner and Laskey (1974) *Eur J Biochem* 46:83-88). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

The terms "sequence similarity" and "sequence identity" as used herein refer to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e. the window size), and multiplying the result by 100 to yield the percentage of sequence identity. For the purposes of the present disclosure, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

The nucleic acid molecules taught herein are also capable of hybridizing to other genetic molecules. Reference herein to "hybridizes" refers to the process by which a nucleic acid strand joins with a complementary strand through base pairing. Hybridization reactions can be sensitive and selective so that a particular sequence of interest can be identified even in samples in which it is present at low concentrations. Stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, the present nucleic acids are defined by their ability to hybridize under various stringency conditions (e.g. high, medium, and low).

The isolated nucleic acid molecule may also be in a vector including an expression or transfer vector suitable for use in plant cells, microbial cells and non-human animal cells. Reference to a "vector" includes a multi-gene expression vector (MGEV) such as described by PCT/AU02/00123.

In accordance with the latter aspect, there is provided a multigene expression vehicle (MGEV) comprising a polynucleotide having 2 to 8 domain segments each domain encoding a functional protein, each domain being joined to the next in a linear sequence by a linker segment, the domain and segments all being in the same reading frame, and wherein at least one of the domains is a modified Class II solanaceous defensin as described herein. In an embodiment, at least one other domain is a proteinase inhibitor or precursor thereof. In yet another embodiment, at least one domain is a modified Class II solanaceous defensin as contemplated herein, and at least one domain is a proteinase inhibitor or precursor form thereof. By "proteinase inhibitor" includes a serine proteinase inhibitor and a cysteine proteinase inhibitor.

The nucleic acid sequence encoding the modified defensin may be incorporated into a DNA construct or vector in combination with suitable regulatory sequences (promoter, terminator, transit peptide, etc). The nucleic acid may also be operably linked to a heterologous promoter. For some applications, the nucleic acid sequence encoding the modified defensin may be inserted within a coding region expressing another protein to form a defensin fusion protein or may be used to replace a domain of a protein to give that protein anti-pathogen activity. The nucleic acid sequence may be placed under the control of a homologous or heterologous promoter which may be a constitutive or an inducible promoter (stimulated by, for example, environmental conditions, presence of a pathogen, presence of a chemical). The transit peptide may be homologous or heterologous to the modified defensin and is chosen to ensure secretion to the desired organelle or to the extracellular space. The transit peptide may be naturally associated with a particular defensin. Such a DNA construct may be cloned or transformed into a biological system which allows expression of the encoded modified defensin or an active part of the defensin. Suitable biological systems include microorganisms (for example, the *Pichia pastoris* expression system, *Escherichia coli, Pseudomonas*, endophytes such as *Clavibacter xyli* subsp. cynodontis (Cxc); yeast; viruses; bacteriophages; etc), cultured cells (such as insect cells, mammalian cells) and plants. In some cases, the expressed defensin is subsequently extracted and isolated for use.

The modified defensin taught herein is useful for combating pathogen diseases in plants and animals including mammals such as humans. Hence, the modified Class II solanaceous defensins have horticultural and agricultural applications as well as applications as medicaments for animal including mammalian such as human use. Further provided is a process of combating pathogens whereby they are exposed to the modified defensin herein described. The modified defensin may be used in the form of a composition. The modified defensin may be used alone or in combination with a chemical pathogenicide, an anti-pathogen protein and/or a Type II serine or cysteine proteinase inhibitor or precursor form thereof.

Whilst the modified defensin herein described is useful for protecting plants against pathogen infestation, growth, maintenance or spread, the modified defensin also has application as medicaments, including topical medicaments, for non-plants such as animals including mammals such as humans.

Hence, another aspect taught herein is a composition comprising the modified defensin as described herein together with one or more pharmaceutically or veterinarilly or horticulturally acceptable carriers, diluents or excipients and/or one or more other anti-pathogen agents such as a chemical pathogenicide, a proteinaceous anti-pathogen agent and/or a proteinase inhibitor or a precursor form thereof. In an embodiment, the composition is in the form of a spray, mist, micro- or nano-particles, aqueous solution, powder, cream, ointment, gel, impregnated bandage, liquid, formulation, paint or other suitable distribution medium including oral forms of the composition.

For pharmaceutical applications, the modified defensin (including any product derived from it) may be used as a pathogenicide or a pathogenostat to treat mammalian infections (for example, to combat yeasts such as *Candida*).

The modified defensin (including any product derived from it) according to the present disclosure may also be used as a preservative (for example, as a food additive) or as part of a soil or growth medium preparation program.

For agricultural applications, the modified defensin may be used to improve the disease-resistance or disease-tolerance of crops either during the life of the plant or for post-harvest crop protection. Pathogens exposed to the peptides are inhibited. The modified defensin may eradicate a pathogen already established on the plant or may protect the plant from future pathogen attack. The eradicant effect of the peptide is particularly advantageous. Reference to a "plant" includes a crop plant such as sorghum, wheat, barley, maize, cotton, rice, canola, corn, abaca, alfalfa, almond, apple, asparagus, banana, bean-*phaseolus*, blackberry, broad bean, cashew, cassava, chick pea, citrus, coconut, coffee, fig, flax, grapes, groundnut, hemp, lavender, mushroom, olive, onion, pea, peanut, pear, pearl millet, potato, rapeseed, ryegrass, soybean, strawberry, sugar beet, sugarcane, sunflower, sweetpotato, taro, tea, tobacco, tomato, triticale, truffle and yam.

Exposure of a plant pathogen to the modified defensin may be achieved in various ways, for example:

(a) The modified defensin may be applied to plant parts or to the soil or other growth medium surrounding the roots of the plants or to the seed of the plant before it is sown using standard agricultural techniques (such as spraying). The defensin may have been chemically synthesized or extracted from microorganisms or plants genetically modified to express the protein. The protein may be applied to plants or to the plant growth medium in the form of a composition comprising the defensin in admixture with a solid or liquid diluent and optionally various adjuvants such as surface-active agents. Solid compositions may be in the form of dispersible powders, granules, or grains.

(b) A composition comprising a microorganism genetically modified to express the anti-pathogen defensin may be applied to a plant or the soil in which a plant grows.

(c) An endophyte genetically modified to express the anti-pathogen defensin may be introduced into the plant tissue (for example, via a seed treatment process). An endophyte is defined as a microorganism having the ability to enter into non-pathogenic endo symbiotic relationships with a plant host. A method of endophyte-enhanced protection of plants has been described in a series of patent applications by Crop Genetics International Corporation (for example, International Application Publication Number WO90/13224, European Patent Publication Number EP-125468-B1, International Application Publication Number WO91/10363, International Application Publication Number WO87/03303). The endophyte may be genetically modified to produce agricultural chemicals. International Patent Application Publication Number WO94/16076 (ZENECA Limited) describes the use of endophytes which have been genetically modified to express a plant-derived anti-fungal peptide.

(d) DNA encoding an anti-pathogen defensin may be introduced into the plant genome so that the peptide is expressed within the plant body (the DNA may be cDNA, genomic DNA or DNA manufactured using a standard nucleic acid synthesizer).

For compositions comprising the modified defensin described herein, generally include a carrier, excipient, diluent, preservative, stabilizer and/or a solid or liquid additive. Optionally, another anti-pathogenic agent is also included.

The composition may take a wide variety of forms depending on the intended method of administration. Generally, but not exclusively, topical compositions are used for plant and animals. In preparing the compositions, usual media may be employed such as, for example, water, glycols, oils, alcohols, preservatives and/or coloring agents. The compositions may take the form of a liquid preparation such as, for example, suspensions, elixirs and solutions. Carriers such as starches, sugars, microcrystalline cellulose, diluents, granulating agents, lubricants, binders, disintegrating agents and the like may also be used. The composition may also be in the form of a power, capsule and tablet.

The modified defensins herein may be administered directly to a plant or part thereof or to the root system or soil or medium surrounding the root system or to the skin, hair or fur of an animal including a mammal such as a human.

When administered by aerosol or spray, the compositions are prepared according to techniques well-known in the art of agricultural and pharmaceutical formulation and may be prepared as solutions in saline, employing benzyl alcohol or other suitable preservatives, absorption promoters to enhance bioavailability, fluorocarbons and/or other solubilizing or dispersing agents known in the art.

The effective dosage of the modified defensins may vary depending on the particular defensin employed, the mode of administration, the pathogen being treated and the severity of the pathogen infestation. Thus, the dosage regimen utilizing the modified defensin is selected in accordance with a variety of factors including type, species, age, weight, sex and medical condition of the plant or subject; the severity of the condition to be treated; the route of administration; and the particular defensin thereof employed. A horticulturist, physician, clinician or veterinarian of ordinary skill can readily determine and prescribe the effective amount of the defensin required to prevent, counter or arrest the progress of pathogen infestation. Slow release formulations are also contemplated herein.

Dragee cores are provided with suitable coatings. For this purpose, concentrated sugar solutions may be used, which may optionally contain gum arabic, talc, polyvinyl pyrrolidone, carbopol gel, polyethylene glycol and/or titanium dioxide, lacquer solutions, and suitable organic solvents or solvent mixtures. Dyestuffs or pigments may be added to the tablets or dragee coatings for identification or to characterize different combinations of active compound doses.

Defensin preparations include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The modified defensin composition or expression vector encoding same may also comprise another anti-pathogen substance such as another defensin or an anti-pathogen protein or peptide, or a chemical pathogenicide or a proteinase inhibitor or precursor from thereof.

Another aspect taught herein includes a protocol or method for treating or preventing a plant infested with a pathogen, the protocol or method comprising applying to the plant or part thereof or to the soil or growth support medium around the plant an anti-pathogen effective amount of a composition comprising the modified defensin as described herein, alone or together with another anti-pathogen agent.

Another aspect provides a protocol or method for treating or preventing an animal including a mammalian such as a human subject infected or infested with a pathogen, the protocol or method comprising applying to the subject an anti-pathogen effective amount of a composition comprising the modified defensin as described herein.

The term "applying" includes contacting and exposing. The modified defensin may be used alone or together with other anti-pathogen agents or agents which facilitate the modified defensin accessing a pathogen.

In a further embodiment, plant cells may be transformed with recombinant DNA constructs according to a variety of known methods (*Agrobacterium* Ti plasmids, electroporation, microinjection, microprojectile gun, etc). The transformed cells may in suitable cases be regenerated into whole plants in which the new nuclear material is stably incorporated into the genome. Both transformed monocotyledonous and dicotyledonous plants may be obtained in this way, although the latter are usually regenerated more easily. Some of the progeny of these primary transformants inherit the recombinant DNA encoding the anti-pathogen defensin.

The present disclosure further provides a plant having improved resistance to a pathogen and containing recombinant DNA which expresses a modified Class II solanaceous defensin. Such a plant may be used as a parent in standard plant breeding crosses to develop hybrids and lines having pathogen including fungal resistance.

Recombinant DNA is DNA, generally heterologous, which has been introduced into the plant or its ancestors by transformation. The recombinant DNA encodes a modified Class II solanaceous defensin expressed for delivery to a site of pathogen attack (such as the leaves).

Where the present modified defensin is expressed within a transgenic plant or its progeny, the pathogen is exposed to the defensin at the site of or remote to the site of pathogen attack on the plant. In particular, by use of appropriate gene regulatory sequences, the defensin may be produced in vivo when and where it will be most effective. For example, the defensin may be produced within parts of the plant where it is not normally expressed in quantity but where disease resistance is important (such as in the leaves).

Examples of genetically modified plants which may be produced include field crops, cereals, fruit and vegetables such as: corn, soybean, sorghum, wheat, barley, maize, cotton, canola, rice, abaca, alfalfa, almond, apple, asparagus, banana, bean-*phaseolus*, blackberry, broad bean, canola, cashew, cassava, chick pea, citrus, coconut, coffee, fig, flax, grapes, groundnut, hemp, lavender, mushroom, olive, onion, pea, peanut, pear, pearl millet, potato, rapeseed, ryegrass, strawberry, sugar beet, sugarcane, sunflower, sweetpotato, taro, tea, tobacco, tomato, triticale, truffle and yam.

A pathogen may be any pathogen growing on, in or near the plant. In this context, resistance includes an enhanced tolerance to a pathogen when compared to a wild-type plant. Resistance may vary from a slight increase in tolerance to the effects of the pathogen (where the pathogen in partially inhibited) to total resistance so that the plant is unaffected by the presence of pathogen (where the pathogen is severely inhibited or killed). An increased level of resistance against a particular pathogen or resistance against a wider spectrum of pathogens may both constitute an improvement in resistance. Transgenic plants (or plants derived therefrom) showing improved resistance are selected following plant transformation or subsequent crossing.

The present disclosure provides a method for generating a genetically modified plant or its progeny which exhibit anti-pathogen activity, the method comprising creating a plant which comprises cells which express the nucleic acid encoding a modified defensin, as taught herein the level of expression sufficient for the modified defensin to exhibit a protective effect against plant pathogens.

The present modified defensins may be used alone or in combination with one or more other defensins from any group of the defensins. Hence, provided herein is a method for generating plant exhibiting anti-pathogen properties, the method comprising creating a genetically modified plant or its progeny which comprises cells which express the modified Class II solanaceous defensin taught herein in combination with another defensin. Such a plant has reduced risk of promoting resistance by pathogens. Reference to "synergy" includes the combatting of resistance to a single defensin by using two or more defensins.

The present modified defensin may be manufactured based on its amino acid sequence using standard stepwise addition of one or more amino acid residues using, for example, a peptide or protein synthesizer. Alternatively, the modified defensin may be made by recombinant means. The modified defensin may be used alone or in combination with other anti-pathogen agents whether provided by a cell or topically or systemically applied.

As indicated above, the present modified defensin exhibits improved or enhanced anti-pathogen activity. In a particular embodiment, the pathogen is a fungal pathogen.

Hence, in a particular embodiment, there is provided an artificially created Class II solanaceous defensin, the defensin comprising a Class II solanaceous defensin backbone with a Loop 1B region on the backbone modified by a single or multiple amino acid substitution, addition and/or deletion to generate a defensin which has anti-fungal activity wherein the backbone may optionally comprise a single or multiple amino acid substitution, addition and/or deletion elsewhere on the backbone such as in the C-terminal CTPP. The present disclosure further contemplates the use of an artificially created defensin comprising a backbone amino acid sequence from a Class II solanaceous defensin having a Loop 1B region or its equivalent loop between the first β-strand and the α-helix on the N-terminal end portion of the Class II solanaceous defensin wherein the Loop 1B region is modified by a single or multiple amino acid substitution, addition and/or deletion in the manufacture of an anti-pathogen medicament.

Furthermore, another aspect is the use of a Class II solanaceous defensin comprising a C-terminal end region having at least about 70% similarity to SEQ ID NO:52 in the manufacture of an artificially created defensin comprising a modified Loop 1B region and which artificially created defensin exhibits anti-pathogen activity.

Further provided herein is a method for reducing or controlling pathogen infestation on or in a plant or in soil surrounding a plant or its roots, the method comprising topically applying the modified defensin of the present disclosure to the plant or plant roots or to the soil. Alternatively, the method comprises generating a genetically modified plant expressing the modified defensin as well as progeny of the modified plants which contain the modified defensin.

Still another aspect provides a method for reducing or controlling pathogen infestation on or in an animal the method comprising topically applying the present modified Class II solanaceous defensin to a potentially infected surface region on the animal. In an embodiment, the animal is a mammal including a human. Hence, animal and in particular mammalian such as human anti-pathogen medicaments are contemplated herein. In an embodiment, the medicament is in the form of a powder, spray, atomizer, nanoparticle, gel, paste, impregnated bandage, paint, aerosol, drench or other liquid. The anti-pathogen formulation may also be a slow release composition. The formulation may be used to treat an infected subject or as a preventative.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The present disclosure illustratively described herein suitably may be practiced in the absence of any element or elements, limitation or limitations which is not specifically disclosed herein.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

When a range is recited herein, it is intended that all subranges within the stated range, and all integer values within the stated range, are intended, as if each subrange and integer value was recited.

Various aspects are encompassed by the subject specification. These aspects include the following:

1. An artificially created defensin comprising a backbone amino acid sequence from a Class II solanaceous defensin having a loop region between β-strand 1 and the α-helix on the N-terminal end portion of the Class II solanaceous defensin wherein the loop region is modified by an amino acid substitution, addition and/or deletion to generate a defensin which has anti-pathogen activity.

2. The artificially created defensin of Aspect 1 wherein the loop region is Loop 1B.

3. The artificially created defensin of Aspect 2 wherein the Loop 1B on the Class II solanaceous defensin is modified to generate the sequence $X_1$ $X_2$ $X_3$ $X_4$ $X_5$ $X_6$, SEQ ID NO:1, wherein X is an amino acid residue and wherein:
   $X_1$ is A, R, N, D, C, Q, E, G, H, I, L, K, M, F, P, S, T, W, Y or V or a naturally occurring modified form thereof;
   $X_2$ is A, R, N, D, C, Q, E, G, H, I, L, K, M, F, P, S, T, W, Y or V or a naturally occurring modified form thereof;
   $X_3$ is A, R, N, D, C, Q, E, G, H, I, L, K, M, F, P, S, T, W, Y or V or a naturally occurring modified form thereof;
   $X_4$ is A, R, N, D, C, Q, E, G, H, I, L, K, M, F, P, S, T, W, Y or V or a naturally occurring modified form thereof;
   $X_5$ is A, R, N, D, C, Q, E, G, H, I, L, K, M, F, P, S, T, W, Y or V or a naturally occurring modified form thereof; and/or
   $X_6$ is A, R, N, D, C, Q, E, G, H, I, L, K, M, F, P, S, T, W, Y or V or a naturally occurring modified form thereof;
   wherein the amino acid sequence $X_1$ $X_2$ $X_3$ $X_4$ $X_5$ $X_6$ does not correspond to an amino acid sequence of the Loop 1B region from the Class II solanaceous defensin prior to modification.

4. The artificially created defensin of Aspect 3 wherein the Loop 1B on the Class II solanaceous defensin is modified to generate the sequence $X_1$ $X_2$ $X_3$ $X_4$ $X_5$ $X_6$, SEQ ID NO:86, wherein X is an amino acid residue and wherein:
   $X_1$ is N, G, D, H, K, A, E, Q, T, P, L, M, S, or R;
   $X_2$ is K, R, G, H, L, N, F, I, S, T or Y;
   $X_3$ is W, Y, H, L, G, F or P;
   $X_4$ is P, K, S, R, H, T, E, V, N, Q, D or G;
   $X_5$ is S, K, Y, F, G or H; and/or
   $X_6$ is P, V, L, T, A, F, N, K, R, M, G, H, I or Y;
   wherein the amino acid sequence $X_1$ $X_2$ $X_3$ $X_4$ $X_5$ $X_6$ does not correspond to an amino acid sequence of the Loop 1B region from the Class II solanaceous defensin prior to modification.

5. The artificially created defensin of Aspect 4 wherein the Loop 1B comprises the sequence $X_1$ $X_2$ $X_3$ $X_4$ $X_5$ $X_6$, SEQ ID NO:55, wherein:
   $X_1$ is N, H, Q, D, K or E;
   $X_2$ is R, H, T, K or G;
   $X_3$ is F, H, Y or W;
   $X_4$ is P, K, S or R;
   $X_5$ is G or F; and/or
   $X_6$ is P, V, I or N.

6. The artificially created defensin of Aspect 3 wherein:
   $X_1$ is an amino acid selected from the list consisting of: L, F, S, I, A, H, Y, Q, D, K, G;
   $X_2$ is an amino acid selected from the list consisting of: S, V, F, I, K, L, A, P, N, T, R, H, G;
   $X_3$ is an amino acid selected from the list consisting of: A, F, W, N, I, S, Y, P, L, H;
   $X_4$ is an amino acid selected from the list consisting of: K, G, E, R, A, P, F, Q, V, S;
   $X_5$ is an amino acid selected from the list consisting of: M, G, K, D, S, Y, P, E, N, F; and
   $X_6$ is an amino acid selected from the list consisting of: V, T, M, S, W, A, P, G, E, K, L, H, I, N. See SEQ ID NO:56.

7. The artificially created defensin of Aspects 3 or 4 or 5 or 6 wherein the Loop 1B on the Class II solanaceous defensin is modified to the amino acid sequence HRFKGP (SEQ ID NO:29) (NaD2), QHHSFP (SEQ ID NO:30) (Zea2), DTYRGV (SEQ ID NO:31) (PsD1), DKYRGP (SEQ ID NO:33) (MsDef1), KTFKGI (SEQ ID NO:34) (SoD2), KTWSGN (SEQ ID NO:35) and (DmAMP1) or a Loop 1B defined by SEQ ID NO:67 to SEQ ID NO:79.

8. The artificially created defensin of any one of Aspects 1 to 7 wherein the Class II solanaceous defensin comprises a C-terminal end region of a mature domain having at least 70% similarity to SEQ ID NO:52 after optimal alignment.

9. The artificially created defensin of Aspect 8 wherein the Class II solanaceous defensin is selected from NaD1, NsD1, NsD2, PhD1, PhD2, TPP3, FST, NeThio1, NeThio2, NpThio1, Na-gth, Cc-gth, C20 or SL549.

10. The artificially created defensin of Aspect 9 wherein the Class II solanaceous defensin is NaD1.

11. The artificially created defensin of Aspect 9 wherein the Class II solanaceous defensin is a defensin from *Nicotiana suaveolens* selected from NsD1 and NsD2.

12. The artificially created defensin of Aspect 2 wherein a Loop 1B from a non-Class II solanaceous defensin listed in FIG. 2 replaces the Loop 1B on the Class II solanaceous defensin.

13. The artificially created defensin of Aspect 7 wherein the Loop 1B is a modified form of NTFPGI from NaD1 (amino acids 8-13 of SEQ ID NO:2) wherein the modification comprises one or more of:
   the N is substituted with an amino acid residue selected from A, R, D, C, Q, E, G, H, I, L, K, M, F, P, S, T, W, Y or V or a naturally occurring modified form thereof;
   the T is substituted with an amino acid residue selected from A, R, N, D, C, Q, E, G, H, I, L, K, M, F, P, S, W, Y or V or a naturally occurring modified form thereof;
   the F is substituted with an amino acid residue selected from A, R, N, D, C, Q, E, G, H, I, L, K, M, P, S, T, W, Y or V or a naturally occurring modified form thereof;
   the P is substituted with an amino acid residue selected from A, R, N, D, C, Q, E, G, H, I, L, K, M, F, S, T, W, Y or V or a naturally occurring modified form thereof;
   the G is substituted with an amino acid residue selected from A, R, N, D, C, E, H, I, L, K, M, F, P, S, T, W, Y or V or a naturally occurring modified form thereof; and/or
   the I is substituted by an amino acid residue selected from A, R, N, D, C, Q, E, G, H, L, K, M, F, P, S, T, W, Y or V or a naturally occurring modified form thereof;
   wherein the amino acid sequence $X_1$ $X_2$ $X_3$ $X_4$ $X_5$ $X_6$ does not correspond to an amino acid sequence of the Loop 1B region from the Class II solanaceous defensin prior to modification.

14. The artificially created defensin of Aspect 13 wherein Loop 1B is a modified form of NTFPGI from NaD1 (amino acids 8-13 of SEQ ID NO:2) wherein the modification comprises one or more of:
   the N is substituted with an amino acid residue selected from G, D, H, K, A, E, Q, T, P, L, M, S and R;
   the T is substituted with an amino acid residue selected from K, R, G, H, L, N, F, I, S and Y;
   the F is substituted with an amino acid residue selected from W, Y, H, L, G and P;
   the P is substituted with an amino acid residue selected from K, S, R, H, T, E, V, N, Q, D or G;
   the G is substituted with an amino acid residue selected from S, K, Y, F and H; and/or the I is substituted by an amino acid residue selected from P, V, L, T, A, F, N, K, R, M, G, H and Y; See also SEQ ID NO:87.

wherein the amino acid sequence $X_1\ X_2\ X_3\ X_4\ X_5\ X_6$ does not correspond to an amino acid sequence of the Loop 1B region from the Class II solanaceous defensin prior to modification.

15. The artificially created defensin of any one of Aspects 1 to 14 wherein the backbone Class II solanaceous defensin further comprises an amino acid substitution, addition and/or deletion on the backbone outside said loop region.
16. The artificially created defensin of Aspect 15 wherein the further amino acid substitution, addition and/or deletion is a substitution of one or more amino acids in the C-terminal tail.
17. The artificially created defensin of any one of Aspects 1 to 16 wherein having the enhanced anti-pathogen activity selected from a broader spectrum of anti-pathogen activity, increased anti-pathogen activity, greater stability and/or greater permeabilization ability relative to the backbone Class II solanaceous defensin.
18. The artificially created defensin of Aspect 17 wherein the anti-pathogen activity is the level of activity against a fungus.
19. The artificially created defensin of Aspect 17 wherein the anti-pathogen activity is the level of activity against an insect.
20. The artificially created defensin of Aspect 18 wherein the fungus is a plant fungal pathogen.
21. The artificially created defensin of Aspect 20 wherein the fungus is a mammalian fungal pathogen.
22. The artificially created defensin of Aspect 21 wherein the fungus is a human fungal pathogen.
23. The artificially created defensin of Aspect 20 wherein the fungus is selected from *Colletotrichum graminicola*, *Diplodia maydis*, *Fusarium graminearum* and *Fusarium verticilloides*.
24. The artificially created defensin of Aspect 20 wherein the fungus is selected from Corn: *Gibberella zeae* (*Fusarium graminearum*), *Colletotrichum graminicola*, *Stenocarpella maydi* (*Diplodia maydis*), *Fusarium moniliforme* var. *subglutinans*, *Fusarium verticilloides*, *Bipolaris maydis* O, T (*Cochliobolis heterostrophus*), *Exserohilum turcicum* I, II and III, *Cercospora zeae-maydis*, *Pythium irregulare*, *Pythium debaryanum*, *Pythium graminicola*, *Pythium splendens*, *Pythium ultimum*, *Pythium aphanidermatum*, *Aspergillus* spp, *Aspergillus flavus*, *Helminthosporium carbonum* I, II and III (*Cochliobolus carbonum*), *Helminthosporium pedicellatum*, *Physoderma maydis*, *Phyllosticta maydis*, *Kabatiella maydis*, *Cercospora sorghi*, *Ustilago maydis*, *Ustilago zeae*, *Puccinia sorghi*, *Puccinia polysora*, *Macrophomina phaseolina*, *Penicillium oxalicum*, *Nigrospora oryzae*, *Cladosporium herbarum*, *Curvularia lunata*, *Curvularia inaequalis*, *Curvularia pallescens*, *Trichoderma viride*, *Claviceps sorghi*, *Diplodia macrospora*, *Sclerophthora macrospora*, *Peronosclerospora sorghi*, *Peronosclerospora philippinensis*, *Peronosclerospora maydis*, *Peronosclerospora sacchari*, *Sphacelotheca reiliana*, *Physopella zeae*, *Cephalosporum maydis*, *Cephalosporum acremonium*; Soybeans: *Fusarium virguluiforme*, *Fusarium solani*, *Sclerotinia sclerotiorum*, *Fusarium oxysporum*, *Fusarium tucumaniae*, *Phakopsora pachyrhizi*, *Phytophthora megasperma* f. sp. *glycinea*, *Phytophthora sojae*, *Macrophomina phaseolina*, *Rhizoctonia solani*, *Sclerotinia sclerotiorum Diaporthe phaseolorum* var. *sojae* (*Phomopsis sojae*), *Diaporthe phaseolorum* var. *caulivora*, *Sclerotium rolfsii*, *Cercospora kikuchii*, *Cercospora sojina*, *Peronospora manshurica*, *Colletotrichum dematium* (*Colletotrichum truncatum*), *Corynespora cassiicola*, *Septoria glycines*, *Phyllosticta sojicola*, *Alternaria alternata*, *Microsphaera diffusa*, *Fusarium semitectum*, *Phialophora gregata*, *Glomerella glycines*, *Pythium aphanidermatum*, *Pythium ultimum*, *Pythium debaryanum*; Canola: *Albugo candida*, *Alternaria brassicae*, *Leptosphaeria maculans*, *Rhizoctonia solani*, *Sclerotinia sclerotiorum*, *Mycosphaerella brassicicola*, *Pythium ultimum*, *Peronospora parasitica*, *Fusarium oxysporum*, *Fusarium avenaceum*, *Fusarium roseum*, *Alternaria alternata*; Cotton: *Fusarium oxysporum* f. sp. *vasinfectum*, *Verticillium dahliae*, *Thielaviopsis basicola*, *Alternaria macrospora*, *Cercospora gossypina*, *Phoma exigua* (*Ascochyta gossypii*), *Pythium* spp *Rhizoctonia solani*, *Puccinia scheddardii*, *Puccinia cacabata*, *Phymatotrichopsis omnivore*; Canola: *Leptosphaeria maculans*, *Sclerotinia sclerotiorum*, *Alternaria brassicae*, *Alternaria brasicicola*, *Plasmodiophora brassicae*, *Rhizoctonia solani*, *Fusarium* spp, *Pythium* spp, *Phytophthora* spp, *Alternaria* spp, *Peronospora parasitica*, *Mycosphaerella capsellae* (*Pseudocercosporella capsellae*), *Albugo candida*, *Phytophtohora megasperma* var. *megasperma*, *Botrytis cinerea*, *Erysiphe cruciferarum*; Wheat: *Cochliobolus sativus*, *Drechslera wirreganensis*, *Mycosphaerella graminicola*, *Phaeosphaeria avenaria* f. sp. *triticea*, *Phaeosphaeria nodorum*, *Blumeria graminis* f. sp. *tritici*, *Urocystis agropyri*, *Alternaria alternata*, *Cladosporium herbarum*, *Fusarium graminearum*, *Fusarium avenaceum*, *Fusarium culmorum*, *Fusarium pseudograminearum*, *Ustilago tritici*, *Ascochyta tritici*, *Cephalosporium gramineum*, *Colletotrichum graminicola*, *Erysiphe graminis* f. sp. *tritici*, *Puccinia graminis* f. sp. *tritici*, *Puccinia recondita* f. sp. *tritici*, *Puccinia striiformis*, *Puccinia triticina*, *Sclerophthora macrospora*, *Urocystis agropyri*, *Pyrenophora tritici-repentis*, *Pyrenophora semeniperda*, *Phaeosphaeria nodorum*, *Septoria nodorum*, *Septoria tritici*, *Septoria avenae*, *Pseudocercosporella herpotrichoides*, *Rhizoctonia solani*, *Rhizoctonia cerealis*, *Gaeumannomyces graminis* var. *tritici*, *Pythium* spp, *Pythium aphanidermatum*, *Pythium arrhenomannes*, *Pythium gramicola*, *Pythium ultimum*, *Bipolaris sorokiniana*, *Claviceps purpurea*, *Tapesia yallundae*, *Tilletia tritici*, *Tilletia laevis*, *Tilletia caries*, *Tilletia indica*, *Ustilago tritici*, *Wojnowicia graminis*, *Cochliobolus sativus*; Sorghum: *Exserohilum turcicum*, *Colletotrichum sublineolum*, *Cercospora sorghi*, *Gloeocercospora sorghi*, *Ascochyta sorghina*, *Puccinia purpurea*, *Macrophomina phaseolina*, *Perconia circinata*, *Fusarium moniliforme*, *Alternaria alternata*, *Bipolaris sorghicola*, *Helminthosporium sorghicola*, *Curvularia lunata*, *Phoma insidiosa*, *Ramulispora sorghi*, *Ramulispora sorghicola*, *Phyllachara saccari*, *Sporisorium reilianum* (*Sphacelotheca reiliana*), *Sphacelotheca cruenta*, *Sporisorium sorghi*, *Claviceps sorghi*, *Rhizoctonia solani*, *Acremonium strictum*, *Sclerophthona macrospora*, *Peronosclerospora sorghi*, *Peronosclerospora philippinensis*, *Sclerospora graminicola*, *Fusarium graminearum*, *Fusarium oxysporum*, *Pythium arrhenomanes*, *Pythium graminicola*; Sunflower: *Plasmopara halstedii*, *Sclerotinia sclerotiorum*, *Septoria helianthi*, *Phomopsis helianthi*, *Alternaria helianthi*, *Alternaria zinniae*, *Botrytis cinerea*, *Phoma macdonaldii*, *Macrophomina phaseolina*, *Erysiphe cichoracearum*, *Rhizopus oryzae*, *Rhizopus arrhizus*, *Rhizopus stolonifer*, *Puccinia helianthe*, *Verticillium dahliae*, *Cephalosporum acremonium*, *Phytophthora cryptogea*,

*Albugo tragopogonis*; Alfalfa: *Pythium ultimum, Pythium irregulare, Pythium splendens, Pythium debaryanum, Pythium aphanidermatum, Phytophthora megasperma, Peronospora trifollorum, Phoma medicaginis* var. *medicaginis, Cercospora medicaginis, Pseudopeziza medicaginis, Leptotrochila medicaginis, Fusarium oxysporum, Verticillium albo-atrum, Aphanomyces euteiches, Stemphylium herbarum, Stemphylium alfalfae, Colletotrichum trifolii, Leptosphaerulina briosiana, Uromyces striatus, Sclerotinia trifoliorum, Stagonospora meliloti, Stemphylium botryosum* and *Leptotrichila medicaginis*.

25. The artificially created defensin of Aspect 24 wherein the fungus is selected from *Fusarium graminearum, Colletotrichum graminicola, Stenocarpella maydis, Fusarium verticilloides, Cochliobolis heterostrophus, Exserohilum turcicum, Cercospora zea-maydis, Fusarium virguhforme, Fusarium solanai, Sclerotinia sclerotiorum, Fusarium oxysporum, Fusarium tucumaniae, Phakopsora pachyrhizi.*

26. The artificially created defensin of Aspect 24 wherein the fungus is selected from *Fusarium virguluhforme, Fusarium solani, Sclerotinia sclerotiorum, Fusarium oxysporum, Fusarium tucumaniae.*

27. The artificially created defensin of Aspect 20 wherein the fungus is a rust.

28. The artificially created defensin of Aspect 21 wherein the fungus is selected from *Alternaeria* spp, *Aspergillus* spp, *Candida* spp, *Fusarium* spp, *Trychophyton* spp, *Cryptococcus* spp, *Microsporum* spp, *Penicillium* spp, *Trichosporon* spp, *Scedosporium* spp, *Paeciliomyces* spp, *Acremonium* spp and Dermatiaceous molds.

29. The artificially created defensin of Aspect 24 wherein the fungus is selected from *Alternaria alternata, Aspergillus fumigatus, Aspergillus niger, Aspergillus flavus, Aspergillus nidulans, Aspergillus paraciticus, Candida albicans, Candida dubliniensis, Candida famata, Candida glabrata, Candida guilliermondii, Candida haemulonii, Candida kefyr, Candida krusei, Candida lusitaniae, Candida norvegensis, Candida parapsilosis, Candida tropicalis, Candida viswanathii, Fusarium oxysporum, Fusarium solani, Fusarium monoliforme, Trycophyton rubrum, Trycophyton mentagrophytes, Trycophyton interdigitales, Trycophyton tonsurans, Cryptococcus neoformans, Cryptococcus gattii, Cryptococcus grubii, Microsporum canis, Microsporum gypseum, Penicillium mameffei, Tricosporon beigelii, Trichosporon asahii, Trichosporon inkin, Trichosporon asteroides, Trichosporon cutaneum, Trichosporon domesticum, Trichosporon mucoides, Trichosporon ovoides, Trichosporon pullulans, Trichosporon loubieri, Trichosporon japonicum, Scedosporium apiospermum, Scedosporium prolificans, Paecilomyces variotii, Paecilomyces lilacinus, Acremonium strictum, Cladophialophora bantiana, Wangiella dermatitidis, Ramichloridium obovoideum, Chaetomium atrobrunneum, Dactlaria gallopavum, Bipolaris* spp, *Exserohilum rostratum* as well as *Absidia corymbifera, Apophysomyces elegans, Mucor indicus, Rhizomucor pusillus, Rhizopus oryzae, Cunninghamella bertholletiae, Cokeromyces recurvatus, Saksenaea vasiformis, Syncephalastrum racemosum, Basidiobolus ranarum, Conidiobolus coronatus/Conidiobolus incongruus, Blastomyces dermatitidis, Coccidioides immitis, Coccidioides posadasii, Histoplasma capsulatum, Paracoccidioides brasiliensis, Pseudallescheria boydii* and *Sporothrix schenckii.*

30. The artificially created defensin of Aspect 19 wherein the insects are selected from *Diatraea grandiosella, Ostrinia nubialis, Rhopalosiphum* spp, *Helicoverpa* spp, *Plutella xylostella* and *Lygus* spp.

31. A composition comprising the artificially created defensin of any one of Aspects 1 to 30 and optionally further comprising a chemical or proteinaceous pathogenicide and/or a serine or cysteine proteinase inhibitor or a precursor form thereof.

32. An isolated nucleic acid molecule encoding an artificially created defensin of any one of Aspects 1 to 30.

33. A genetic construct comprising the isolated nucleic acid molecule of Aspect 32.

34. A genetically modified plant which produces an artificially created defensin of any one of Aspects 1 to 30 or progeny of said plant.

35. The genetically modified plant of Aspect 34 comprising a nucleic acid molecule of Aspect 32 or a genetic construct of Aspect 33 or its progeny or propagating material.

36. The genetically modified plant of Aspect 34 or 35 selected from corn, soybean, cotton, sorghum, wheat, barley, maize, canola, abaca, alfalfa, almond, apple, asparagus, banana, bean-phaseolus, blackberry, broad bean, cashew, cassava, chick pea, citrus, coconut, coffee, fig, flax, grapes, groundnut, hemp, lavender, mushroom, olive, onion, pea, peanut, pear, pearl millet, potato, rapeseed, ryegrass, strawberry, sugar beet, sugarcane, sunflower, sweetpotato, taro, tea, tobacco, tomato, triticale, truffle and yam.

37. A method for generating a genetically modified plant or its progeny which exhibit enhanced anti-pathogen activity, the method comprising creating a plant which comprises cells which express the nucleic acid encoding a modified Class II solanaceous defensin of any one of Aspects 1 to 30, the level of expression in the plant or its progeny sufficient for the modified defensin to exhibit a protective effect against plant pathogens.

38. A method of controlling pathogen infestation on a plant, the method comprising topically applying a composition of Aspect 31 to the plant, its roots or soil surrounding the plant.

39. A method of controlling pathogen infestation on an animal subject, the method comprising topically applying a composition of Aspect 31 to a surface on the animal potentially infested by the pathogen.

40. The method of Aspect 37 or 38 further applying a chemical pathogenicide, a proteinaceous pathogenicide or a serine or cysteine proteinase inhibitor or a precursor form thereof.

41. The method of Aspect 39 wherein the animal is a mammal.

42. The method of Aspect 31 wherein the mammal is a human.

43. Use of an artificially created defensin comprising a backbone amino acid sequence from a Class II solanaceous defensin having a loop region between β-strand 1 and the α-helix on the N-terminal end portion of the Class II solanaceous defensin wherein the loop region is modified by a single or multiple amino acid substitution, deletion and/or addition in the manufacture of an anti-pathogen medicament.

44. Use of Aspect 43 wherein the loop region is Loop 1B.

45. Use of Aspect 43 or 44 wherein the pathogen is a fungus.

46. Use of Aspect 43 or 44 or 45 further comprising use of a chemical pathogenicide, a proteinaceous pathogenicide or a serine or cysteine proteinase inhibitor or a precursor form thereof.

47. An isolated defensin from *Nicotiana suaveolens* having an amino acid sequence as set forth in SEQ ID NO:49 [NsD1] or an amino acid sequence having at least 70% thereto after optimal alignment.
48. An isolated defensin from *Nicotiana suaveolens* having an amino acid sequence as set forth in SEQ ID NO:51 [NsD2] or an amino acid sequence having at least 70% thereto after optimal alignment.
49. An isolated nucleic acid molecule or comprising a sequence of nucleotides encoding the defensin of Aspect 47 or 48.
50. The isolated nucleic acid molecule of Aspect 49 comprising a nucleotide sequence selected from SEQ ID NO:48, SEQ ID NO:50, a nucleotide sequence capable of hybridizing to SEQ ID NO:48 or 50, under medium stringency conditions and a nucleotide sequence having at least 70% identity to SEQ ID NO:46 or 48 after optimal alignment.
51. Use of a Class II solanaceous defensin comprising a C-terminal end region of its mature domain having at least about 70% similarity to SEQ ID NO:52 in the manufacture of an artificially created defensin comprising a modified Loop 1B region and which artificially created defensin exhibits anti-pathogen activity.
52. A genetic construct comprising a nucleic acid of Aspect 32 and a nucleic acid encoding a proteinase inhibitor.

EXAMPLES

Aspects are further described by the following non-limiting Examples. Methods used in these Examples are described below.

Purification of Defensins from Solanaceous Flowers

To isolate class II defensins from their natural source, whole *N. alata* (NaD1, NaD2) or *N. suaveolens* (NsD1, NsD2) flowers up to the petal coloration stage of flower development were ground to a fine powder and extracted in dilute sulfuric acid as previously described previously (Lay et al. 2003 supra). Briefly, flowers (760 g wet weight) were frozen in liquid nitrogen, ground to a fine powder in a mortar and pestle, and homogenized in 50 mM sulfuric acid (3 mL per g fresh weight) for 5 min using an Ultra-Turrax homogenizer. After stirring for 1 h at 4° C., cellular debris was removed by filtration through Miracloth (Calbiochem, San Diego, Calif.) and centrifugation (25,000×g, 15 min, 4° C.). The pH was then adjusted to 7.0 by addition of 10 M NaOH and the extract was stirred for 1 h at 4° C. before centrifugation (25,000×g, 15 min, 4° C.) to remove precipitated proteins. The supernatant (1.8 L) was applied to an SP Sepharose (Trademark) Fast Flow (GE Healthcare Bio-Sciences) column (2.5×2.5 cm) pre-equilibrated with 10 mM sodium phosphate buffer. Unbound proteins were removed by washing with 20 column volumes of 10 mM sodium phosphate buffer (pH 6.0) and bound proteins were eluted in 3×10 mL fractions with 10 mM sodium phosphate buffer (pH 6.0) containing 500 mM NaCl. Fractions from the SP Sepharose column were subjected to reverse-phase high performance liquid chromatography (RP-HPLC).

Purification of NaD1 from *Pichia pastoris*

The *Pichia pastoris* expression system is well-known and commercially available from Invitrogen (Carlsbad, Calif.; see the supplier's *Pichia* Expression Manual disclosing the sequence of the pPIC9 expression vector).

A single pPIC9-NaD1 *P pastoris* GS115 colony was used to inoculate 10 mL of BMG medium (described in the Invitrogen *Pichia* Expression Manual) in a 100 mL flask and was incubated overnight in a 30° C. shaking incubator (140 rpm). The culture was used to inoculate 500 mL of BMG in a 2 L baffled flask which was placed in a 30° C. shaking incubator (140 rpm). Once the OD600 reached 2.0 (~18 h), cells were harvested by centrifugation (2,500×g, 10 min) and resuspended into 1 L of BMM medium (OD600=1.0) in a 5 L baffled flask and incubated in a 28° C. shaking incubator for 3 days. The expression medium was separated from cells by centrifugation (4750 rpm, 20 min) and diluted with an equal volume of 20 mM potassium phosphate buffer (pH 6.0). The medium was adjusted to pH 6.0 with NaOH before it was applied to an SP Sepharose column (1 cm×1 cm, Amersham Biosciences) pre-equilibrated with 10 mM potassium phosphate buffer, pH 6.0. The column was then washed with 100 mL of 10 mM potassium phosphate buffer, pH 6.0 and bound protein was eluted in 10 mL of 10 mM potassium phosphate buffer containing 500 mM NaCl. Eluted proteins were subjected to RP-HPLC using a 40 minute linear gradient as described herein below. Protein peaks were collected and analyzed by SDS-PAGE and immunoblotting with the anti-NaD1 antibody. Fractions containing NaD1 were lyophilized and resuspended in sterile milli Q ultrapure water. The protein concentration of *Pichia*-expressed NaD1 was determined using the bicinchoninic acid (BCA) protein assay (Pierce Chemical Co.) with bovine serum albumin (BSA) as the protein standard.

Reverse-phase High Performance Liquid Chromatography

Reverse-phase high performance liquid chromatography (RP-HPLC) was performed on a System Gold HPLC (Beckman) coupled to a detector (model 166, Beckman) using a preparative C8 column (22×250 mm, Vydac) with a guard column attached. Protein samples were loaded in buffer A (0.1% [v/v] trifluoroacetic acid) and eluted with a linear gradient of 0-100% [v/v] buffer B (60% [v/v] acetonitrile in 0.089% [v/v] trifluoroacetic acid) at a flow rate of 10 mL/min over 40 min. Proteins were detected by monitoring absorbance at 215 nm. Protein peaks were collected and analyzed by SDS-PAGE.

Samples from each stage of NaD1 purifications (30 µL) were added to NuPAGE (Registered Trademark) LDS sample loading buffer (10 µL, Invitrogen) and heated to 70° C. for 10 min. The samples were then loaded onto NuPAGE (Registered Trademark) precast 4-12% [w/v] Bis-Tris polyacrylamide gels (Invitrogen) and the proteins were separated using an XCell-Surelock electrophoresis apparatus (Invitrogen) run at 200 V. Proteins were visualized by Coomassie Blue staining or transferred onto nitrocellulose for immunoblotting with the anti-NaD1 antibodies.

Circular Dichroism Spectrum of rNaD1

To examine whether NaD1 purified from *P. pastoris* (rNaD1) was correctly folded, its far UV circular dichroism (CD) spectrum was recorded and compared with that of native NaD1. The similarity of the two spectra indicates the structure of rNaD1 was not significantly altered compared to native NaD1.

PCR Mutagenesis of NaD1

Site directed mutagenesis of NaD1 was carried out using the Phusion (Registered Trademark) site-directed mutagenesis kit (Finnzymes). Oligonucleotide primers phosphorylated at the 5' end were designed to incorporate the desired mutation. The entire template plasmid (pPIC9-NaD1) was amplified in a PCR reaction of 30 cycles with the following temperature profile; 98° C., 30 s; 55° C., 20 s; 72° C., 4 min with a final extension cycle of 72° C. for 10 min. The linear PCR product was then circularized using T4 DNA Quick Ligase for 5 min at RT and transformed into chemically competent TOP10 cells according to the manufacturer's instructions. Constructs were sequenced using the AOX3' primer to ensure the mutation had been correctly incorporated.

Preparation of Electrocompetent *P. pastoris*

Electrocompetent *P. pastoris* GS115 cells (Invitrogen) were prepared as described by Chang et al. (2005) *Mol Biol Cell* 16(10):4941-4953. Briefly, cells grown overnight in YPD (1% w/v Bacto yeast extract, 2% w/v Bacto peptone extract, and 2% w/v dextrose) were harvested and treated with YPD containing 10 mM DTT, 25 mM HEPES, pH 8, for 15 min at 30° C. with shaking. Cells were washed twice in water and once in ice-cold 1 M sorbitol, before they were resuspended in 1 M sorbitol and divided into 80 µL aliquots for storage at −80° C.

Transformation of *P. pastoris* GS115 with pPIC9 Constructs

Single *E. coli* TOP10 colonies transformed with each pPIC9 construct were used to inoculate 10 mL of LB containing 100 µg/mL ampicillin and incubated overnight at 37° C. in a shaking incubator. Plasmid DNA was isolated using the Qiaprep (Registered Trademark) miniprep kit (Qiagen) and linearized overnight using the restriction enzyme SalI. Competent *P. pastoris* GS115 cells (80 µL) were thawed on ice and 1 µg of linearized DNA was added in an ice-cold Gene Pulser (Registered Trademark) electroporation cuvette with a 0.2 cm gap. DNA was introduced by electroporation at 1.5 kV, 25 µF, 400Ω (Gene Pulser, Bio-Rad Laboratories). Ice-cold 1 M sorbitol (1 mL) was added to the cells before they were plated onto MD plates (1.34% w/v yeast nitrogen base, without amino acids and with ammonium sulfate [US Biological, YNB], $4 \times 10^{-5}$% w/v biotin, 2% w/v dextrose) and incubated at 30° C. for 5 days. Positive colonies were then selected and re-plated onto fresh MD plates.

Characterization of rNaD1

FIGS. 6A through D show an immunoblot, reverse phase HPLC trace, structure of rNaD1 isolated from flowers and activity of rNaD1 against hyphal growth.

Amino Acid Sequence Comparisons

Figure 3B:
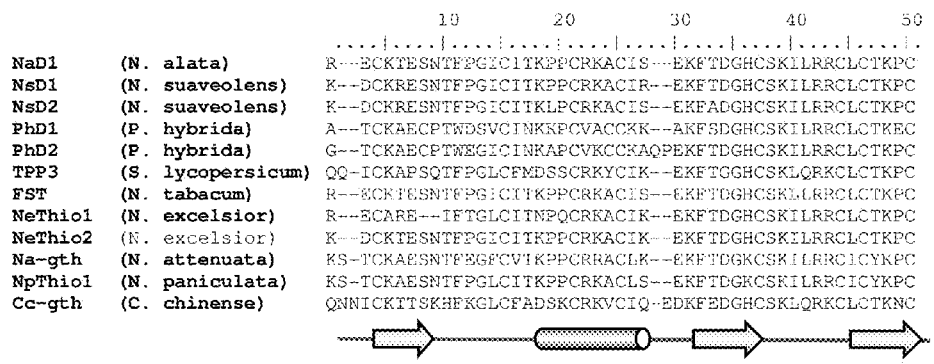

FIGS. 3A and 3B provide a representation of amino acid sequences of various Class II solanaceous defensins including NaD1. FIG. 4 shows Class I and II defensins. The Loop 1B region in these alignments comprises amino acids 10 through 15 in FIG. 3 and amino acids 9 through 14 in FIG. 4. The present disclosure extends to a defensin having the C-terminal 20 contiguous amino acid residues with at least 70% similarity to amino acids 32 to 51 (FIG. 3) of NaD1 (SEQ ID NO:52). Examples are provided in Table 4.

Vector Maps

Figure 11:
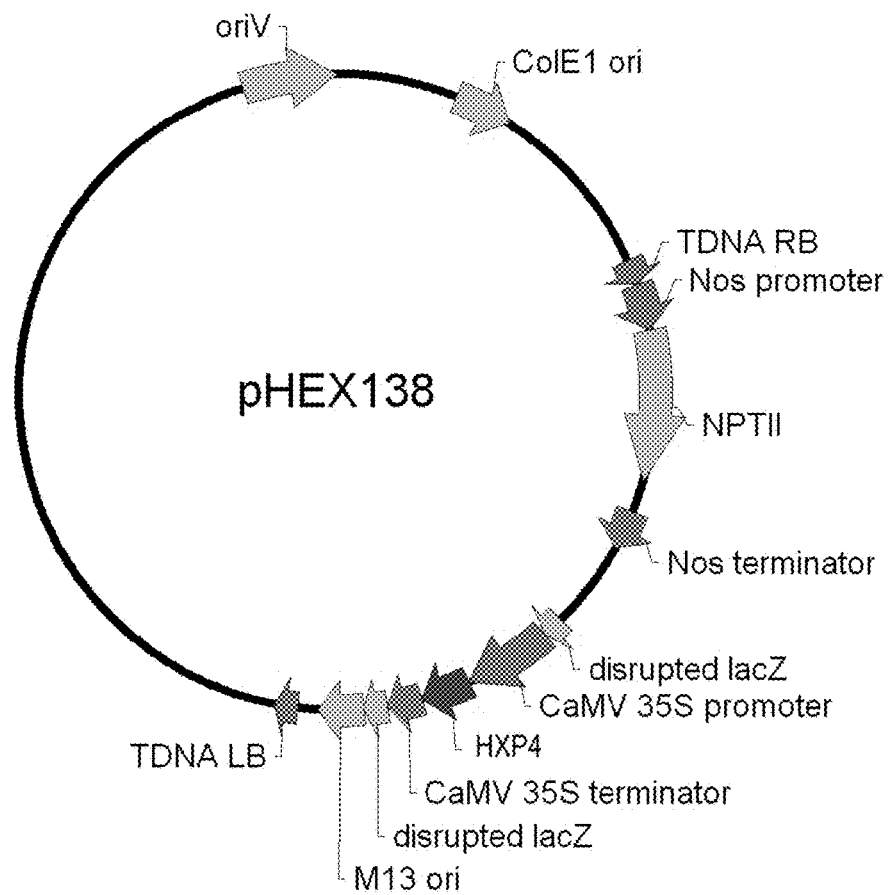

FIG. 11 shows a vector map for pHEX138.

Bioassay Method for in Planta Studies:

Preparation of *C. graminicola* Inoculum:

*Colletotrichum graminicola* (US isolate Carroll-1A-99) was isolated from *Zea maize* (Pioneer Hi-Bred International, Inc. Johnston, Iowa, USA). Spores were isolated from sporulating cultures grown on V8 agar for approximately 2-3 Weeks. *C. graminicola* spores were collected by scraping the surface of the plates in sterile water and separating spores from hyphal matter by filtration through facial tissue. The concentration of spores in the filtrate was measured using a haemocytometer.

Preparation of *F. graminearum* Inoculum:

*Fusarium graminearum* isolate (73B1A) was isolated from *Zea maize* (Pioneer Hi-Bred International, Inc. Johnston, Iowa, USA). Spores were isolated from sporulating cultures grown on SNP agar for approximately 2-3 Weeks. *F. graminearum* spores were collected by scraping the surface of the plates in sterile water. The concentration of spores in was measured using a haemocytometer.

Inoculation of Maize Plants:

Plants for bioassay were grown in the glasshouse for approximately 9-10 weeks after deflasking.

*C. gramincola* Inoculation

Two wounds, 2.0 mm in length were made on opposing sides of the maize leaf sheath and then over laid with $1 \times 10^6$ *C. graminicola* spores/mL. Wounds were then sealed with Glad Pressn'Seal for three days. The area of infection was measured by digital photography 10 days post inoculation.

*F. graminearum* Inoculation

Two wounds, 2.0 mm in length were made on opposing sides of the maize leaf sheath. Wounds were over laid 6 mm diameter paper discs dipped in $1 \times 10^6$ *F. graminearum* spores/mL. Wounds were then sealed with Glad Pressn'Seal for three days. The area of infection was measured by digital photography 10 days post inoculation.

ELISA Method

Protein extract: leaf sheaths were excised from plants grown in the glasshouse. The tissue (50 mg) was frozen in liquid nitrogen and ground in a mixer mill (Retsch MM300) for 2×15 sec at frequency 30 s$^{-1}$. Protein extracts were made by adding 450 µL 2% insoluble PVPP (Polyclar)/PBS/0.05% Tween 20 and vortexing for 20 s. The samples were centrifuged for 10 min and the supernatant was collected.

ELISA plates (Nunc Maxisorp #442404) were incubated with 100 µL/well of primary antibody in PBS (100 ng/well of anti-NaD1 (polyclonal antibody was made by a standard method to purified NaD1 from flowers of *Nicotiana alata*)). Plates were incubated overnight at 4° C. in a humid box. They were then washed for 2 min×4 with PBS/0.05% v/v Tween 20. Plates were blocked with 200 µL/well 3% w/v BSA (Sigma A-7030: 98% ELISA grade) in PBS and incubated for 2 h at 25° C. Plates were then washed for 2 min×4 with PBS/0.05% v/v Tween 20.

Corn sheath protein extracts (100 µL/well diluted in PBS/0.05% v/v Tween 20) were then applied to the plates which were then incubated for 2 h at 25° C. Plates were then washed for 2 min×4 with PBS/0.05% v/v Tween 20 and then 100 µL/well of secondary antibody in PBS (75 ng/well biotin-labelled NaD1 antibody) was applied. The biotin labelled antibody was prepared using the EZ-link Sulfo-NHS-LC-biotinylation kit (Pierce); 2 mL of protein A purified antibody and 2 mg of the biotin reagent were used. Plates were incubated for 1 h at 25° C. and then washed for 2 min×4 with PBS/0.05% v/v Tween 20 and 100 µL/well of NeutriAvidin HRP-conjugate (Pierce #31001; 1:1000 dilution; 0.1 µL/well) in PBS was applied. The plates were incubated for 1 h at 25° C. and then washed for 2 min×2 with PBS/0.05% v/v Tween 20, followed by 2 min×2 with H$_2$O. Just before use, substrate was prepared by dissolving 1 ImmunoPure OPD tablet (Pierce #34006) in 9 mL H$_2$O, then adding 1 mL stable peroxide buffer (10×, Pierce #34062). The substrate was applied at 100 µL/well and plates were incubated at 25° C. until color developed. The reaction was stopped by applying 50 µL 2.5 M sulfuric acid. Absorbance at 490 nm was measured in a plate reader (Molecular Devices).

Immunoblot Analysis

Leaf sheaths were excised from plants grown in the glasshouse. Leaf sheath tissue (50 mg) was frozen in liquid nitrogen and ground to a fine powder in a mixer mill (Retsch MM300) for 2×15 s at frequency 30 s$^{-1}$. Samples were extracted by adding 2% w/v insoluble PVPP (Polyclar)/PBS/0.05% v/v Tween 20 (75 µL) and vortexing. Samples were then centrifuged at 14,000 rpm for 10 min and the supernatants retained. To the supernatant (21 μL), Novex NuPAGE 4×LDS sample buffer (7.5 μL) and β-mercaptoethanol (1.5 μL) were added and heated at 70° C. for 10 min.

Extracted leaf sheath proteins were separated by SDS-PAGE on preformed 4-12% w/v polyacrylamide gradient gels (Novex, NuPAGE bis-tris, MES buffer) for 35 min at 200V in a Novex X Cell II mini-cell electrophoresis apparatus. Prestained molecular weight markers (Novex SeeBlue Plus 2) were included as a standard. Proteins were transferred to nitrocellulose membrane (Osmonics 0.22 micron NitroBind) for 60 min at 30 V using the Novex X Cell mini-cell electrophoresis apparatus in NuPAGE transfer buffer with 10% v/v methanol. After transfer, membranes were incubated for 1 min in isopropanol, followed by a 5 min wash in TBS.

The membrane was blocked for 1 h in 3% w/v BSA at room temperature followed by incubation with primary antibody overnight at room temperature (mature NaD1 or HvCPI6 antibody diluted 1 in 1000 in TBS/1% w/v BSA of 1 mg/ml stock). The membrane was washed 5×10 min in TBST before incubation with goat anti-rabbit IgG conjugated to horseradish peroxidase for 60 min at RT (Pierce, 1 in 50,000 dilution in TBS). Five further 10 min TBST washes were performed before the membrane was incubated with SuperSignal West Pico Chemiluminescent substrate (Pierce) according to the manufacturer's instructions. Membranes were exposed to ECL Hyperfilm (Amersham).

Example 1

Antifungal Activity of Class I Defensins

Three Class I defensins were either purified from their native source (NaD2) or expressed using *P. pastoris* expression system (γ-zeathionin2, γ-hordothionin) as described in the methods. The anti-fungal activity of the peptides was assessed against *Fusarium graminearum* essentially as described in Broekaert et al. (1990) *FEMS Microbiol Lett* 69:55-60, 1990, and compared to that of two solanaceous class II defensins (NaD1, NsD1). Spores were isolated from sporulating cultures growing in half-strength potato dextrose broth (PDB) by filtration through sterile muslin. Spore concentrations were determined using a hemocytometer and adjusted to $5 \times 10^4$ spores/mL in ½×PDB. Spore suspensions (80 μL) were added to the wells of sterile 96-well flat-bottomed microtitre plates along with 20 μL of filter-sterilized (0.22 μm syringe filter; Millipore) protein, or water to give final protein concentrations of 0-10 μM. The plates were shaken briefly and placed in the dark at 25° C. without shaking for 28 h. Hyphal growth was estimated by measuring the optical density at 595 nm using a microtitre plate reader (SpectraMax Pro M5e; Molecular Devices). Each test was performed in triplicate. Results (FIG. 7) showed that the Class I defensins tested exhibited low antifungal activity.

TABLE 4

| Seq-> | NaD1. | NsD1. | NsD2. | PhD1. | PhD2. | TPP3. | FST. | NeThio1. |
|---|---|---|---|---|---|---|---|---|
| NaD1. | ID | 100% | 95% | 90% | 100% | 80% | 95% | 100% |
| NsD1. | 100% | ID | 95% | 90% | 100% | 80% | 95% | 100% |
| NsD2. | 95% | 95% | ID | 90% | 95% | 75% | 90% | 95% |
| PhD1. | 90% | 90% | 90% | ID | 90% | 70% | 85% | 90% |
| PhD2. | 100% | 100% | 95% | 90% | ID | 80% | 95% | 100% |
| TPP3. | 80% | 80% | 75% | 70% | 80% | ID | 85% | 80% |
| FST. | 95% | 95% | 90% | 85% | 95% | 85% | ID | 95% |
| NeThio1. | 100% | 100% | 95% | 90% | 100% | 80% | 95% | ID |
| NeThio2. | 100% | 100% | 95% | 90% | 100% | 80% | 95% | 100% |
| Na-gth. | 85% | 85% | 80% | 75% | 85% | 65% | 80% | 85% |
| NpThio1. | 85% | 85% | 80% | 75% | 85% | 65% | 80% | 85% |
| Cc gth. | 75% | 75% | 75% | 75% | 75% | 85% | 80% | 75% |

| Seq-> | NeThio2. | Na-gth. | NpThio1. | Cc gth. | Source | Accession number |
|---|---|---|---|---|---|---|
| NaD1. | 100% | 85% | 85% | 75% | *Nicotiana alata* | Q8GTM0 |
| NsD1. | 100% | 85% | 85% | 75% | *Nicotiana suaveolens* | none |
| NsD2. | 95% | 80% | 80% | 75% | *Nicotiana suaveolens* | none |
| PhD1. | 90% | 75% | 75% | 75% | *Petunia hybrida* | Q8H6Q1 |
| PhD2. | 100% | 85% | 85% | 75% | *Petunia hybrida* | Q8H6Q0 |
| TPP3. | 80% | 65% | 65% | 85% | *Solanum lycopersicum* | AAA80496 |
| FST. | 95% | 80% | 80% | 80% | *Nicotiana tabacum* | P32026 |
| NeThio1. | 100% | 85% | 85% | 75% | *Nicotiana excelsior* | BAA21114 |
| NeThio2. | ID | 85% | 85% | 75% | *Nicotiana excelsior* | BAA21113 |
| Na-gth. | 85% | ID | 100% | 60% | *Nicotiana attenuata* | AAS13436 |
| NpThio1. | 85% | 100% | ID | 60% | *Nicotiana paniculata* | O24115 |
| Cc gth. | 75% | 60% | 60% | ID | *Capsicum chinense* | AAD21200 |

Example 2

Modification to NaD1 Loop 1B Region on a Class II Solanaceous Defensin

The first aspect of this example is the selection of a Class II solanaceous defensin. Defensins are screened to identify defensins having a C-terminal portion comprising an amino acid sequence as set forth in SEQ ID NO:52 or having at least 70% similarity thereto after optimal alignment (Table 4). FIG. 3 shows the type of alignment. SEQ ID NO:50 represents the terminal 20 continguous amino acids including the most C-terminal invariant cysteine residue. NaD1, NsD1 PhD2, NeThio1 and NeThio2 are examples of defensins having 100% similarity to SEQ ID NO:52.

NaD1 is selected as the Class II solanaecous defensin backbone. This defensin comprises a Loop 1B having the amino acid sequence: NTFPGI (SEQ ID NO:12).

One or more of the amino acid residues NTFPGI is/are substituted by another amino acid residue. All six residues may be altered or 1 or 2 or 3 or 4 or 5 of the residues may be changed. This includes a single amino acid substitution or a Loop 1B swap. Examples of changes made include the following sequences (together with the source in parantheses):

```
                                        [SEQ ID NO: 29]
HRFKGP (NaD2);
                                        [SEQ ID NO: 30]
QHHSFP (Zea2);
                                        [SEQ ID NO: 31]
DTYRGV (PsD1);
                                        [SEQ ID NO: 32]
PTWEGI (PsD2);
                                        [SEQ ID NO: 33]
DKYRGP (MsDeF1(;
                                        [SEQ ID NO: 34]
KTFKGI (SoD2);
                                        [SEQ ID NO: 35]
KTWSGN (DmAMP1);
                                        [SEQ ID NO: 36]
EGWXGK (VrD1);
                                        [SEQ ID NO: 37]
GTWSGV (RsAFP2);
and
                                        [SEQ ID NO: 38]
AGFKGP (g1-H).
```

Other examples include selecting an amino acid sequence selected from SEQ ID NO:67 to 79.

Example 3

Inhibition of the Growth of *Fusarium graminearum* in the Presence of Loop Variants of NaD1

Recombinant NaD1 and the loop variants HXP4, HXP34 and HXP35 were expressed in the *P. pastoris* expression system and purified as described in the methods. The antifungal activity of the peptides against *Fusarium graminearum* was assessed essentially as described in Broekaert et al. (1990) *FEMS Microbiol Lett* 69:55-60. Spores were isolated from sporulating cultures growing in half-strength potato dextrose broth (PDB) by filtration through sterile muslin. Spore concentrations were determined using a hemocytometer and adjusted to $5\times10^4$ spores/mL in ½× PDB. Spore suspensions (80 μL) were added to the wells of sterile 96-well flat-bottomed microtitre plates along with 20 μL of filter-sterilized (0.22 μm syringe filter; Millipore) protein, or water to give final protein concentrations of 0-10 μM. The plates were shaken briefly and placed in the dark at 25° C. without shaking for 28 h. Hyphal growth was estimated by measuring the optical density at 595 nm using a microtitre plate reader (SpectraMax Pro M5e; Molecular Devices). Each test was performed in triplicate.

Results

FIG. 8 illustrates the relative anti-fungal activity of the loop variants HXP4, HXP34 and HXP35 compared to NaD1 against *F. graminearum* (Fgr). At 0.825 ppm, HXP4, HXP34 and HXP35 inhibited the growth of *F. graminearum* by 41.7, 14.6 or 34.5% more than NaD1 respectively. At 1.65 ppm, all three loop variants inhibited the growth of *F. graminearum* by ~70% more than NaD1.

Example 4

Inhibition of the Growth of *Fusarium* Verticilloides in the Presence of Loop Variants of NaD1

Recombinant NaD1 and the loop variants HXP4, HXP34 and HXP35 were expressed in the *P. pastoris* expression system and purified as described in the methods. The antifungal activity of the peptides against *Fusarium verticilloides* was assessed as described in Example 1.

Results

FIG. 9 illustrates the relative anti-fungal activity of the loop variants HXP4, HXP34 and HXP35 compared to NaD1 against *F. verticilloides* (Fve). At 3.25 ppm, HXP4, HXP34 and HXP35 inhibited the growth of *F. verticilloides* by 40.9, 29.4 and 5.1% more than NaD1 respectively. At 6.5 ppm, all three loop variants inhibited the growth of *F. verticilloides* by at least 67% more than NaD1.

Example 5

Inhibition of the Growth of *Colletotrichum graminicola* in the Presence of Loop Variants of NaD1

Recombinant NaD1 and the loop variants HXP4, HXP34 and HXP35 were expressed in the *P. pastoris* expression system and purified as described in the methods. The antifungal activity of the peptides against *Colletotrichum graminicola* was assessed as described in Example 1.

Results

FIG. 10 illustrates the relative anti-fungal activity of the loop variants HXP4, HXP34 and HXP35 compared to NaD1 against *C. graminicola* (Cgr). At 13 ppm, HXP4, HXP34 and HXP35 inhibited the growth of *C. graminicola* by 61.3, 21.8 or 83.2% more than NaD1, respectively.

Example 6

Production of Transgenic Plants

Transgenic canola (*Brassica napus*, cv RI64) expressing HXP4 was produced by *Agrobacterium tumefaciens* mediated transformation. The DNA binary vector used for the transformation (pHEX138) is described in FIG. 11. The binary vector was transferred into *Agrobacterium tumefa-*

*ciens* by electroporation and the presence of the plasmid confirmed by gel electrophoresis. Cultures of *Agrobacterium* were used to infect hypocotyl sections of canola. Transgenic shoots were selected on the antibiotic kanamycin at 25 mg/L. Transgenic plants expressing HXP4 were selected using ELISA to detect soluble proteins extracted from leaves.

From three transformation experiments (CAT93, CAT94 and CAT96) 7 plants (6 events) had detectable levels of HXP4 (Table 5). The level of HXP4 protein ranged from 0.3 to 2.1 ppm (ng HXP4/mg fresh weight of leaf tissue).

TABLE 5

| Transgenic canola line | Level of HXP4 (ppm) |
|---|---|
| 93.1.2 | 2.1 |
| 93.1.3 | 2.0 |
| 93.15.3 | 1.9 |
| 96.7.2 | 1.8 |
| 96.17.1 | 0.3 |
| 96.72.1 | 1.9 |
| 94.11.1 | 1.6 |

Glasshouse Bioassays with *Leptosphaeria maculans*

The pathogen *Leptosphaeria maculans* is grown on 10% (v/v) V8 agar plates for 1-2 weeks at room temperature. Pycnidiospores are isolated by covering the plate with sterilized water (5 mL) and scraping the surface of the agar to dislodge the spores. Spores are separated from the hyphal matter by filtration through sterile tissues. The concentration of the spores in the filtrate is measured using a hemocytometer and the final concentration is adjusted to between $1\times10^6$ to $1\times10^7$ pycnidiospores/mL with water.

Seedlings are grown in the glasshouse in small planting trays at 22° C. Approximately ten days after sowing, the two cotyledons of each seedling are punctured twice with a 26 gauge needle (once in each of the 2 lobes) and the wounded area is inoculated with a droplet of spores (5 µL). Controls are inoculated with water. The plants are maintained under high humidity conditions for 3 days to facilitate spore germination.

Disease symptoms are assessed up to 20 days after inoculation. Lesion size is quantified using computer software analysis (ImageJ) of digital images in mm². The average lesion size is statistically analyzed using non-parametric methods.

Example 7

Production of Transgenic Corn Plants Expressing HXP4

Transgenic corn plants are produced by *Agrobacterium*-mediated transformation or particle bombardment using standard protocols such as those described in U.S. Pat. Nos. 5,981,840; 7,528,293; 7,589,176; 7,785,828; Frame et al. (2002) *Plant Physiology* 129:13-22. A binary vector containing GAT as the selectable marker, a ubiquitin promoter for constitutive expression and a codon optimised sequence encoding either HXP4 or NaD1 under the control of a constitutive ubiquitin promoter as well as a sequence encoding encoding GAT as a selectable marker was transferred into an *Agrobacterium tumefaciens* strain by electroporation. Immature corn embryos were infected via immersion in a suspension of *Agrobacterium* followed by a period of co-culture on a solid medium. The embryos were then optionally "rested" during which time they were incubated in the presence of at least one antibiotic which inhibits the growth of *Agrobacterium*. Next transformed callus was obtained by culturing the infected embryos on solid medium containing glyphosphate which inhibits the growth of non-transformed cells. Transformed callus was then able to be regenerated into plants using standard methods.

Levels of HXP4 and NaD1 expression in PCR positive plants were determined, for example, by ELISA screening. Plants expressing HXP4 or NaD1 at >10 ppm were assessed for increased resistance to *Colletotrichum graminicola* using the bioassay described in the Methods.

Results

Plants expressing HXP4 at >10 ppm showed a 26% reduction in lesion area when compared to plants transformed with an empty vector. Plants expressing NaD1 at >10 ppm showed no reduction in lesion area compared to the empty vector control (Table 8).

Example 8

Production of Transgenic Soybean Plants Expressing HXP4

Transgenic soybean plants expressing HXP4 are produced by *Agrobacterium*-mediated transformation or by particle bombardment or other standard protocols such as those described in U.S. Pat. Nos. 7,589,176; 7,528,293; 7,785,828.

Regenerated soybean plants which are PCR positive for HXP4 are assessed for levels of HXP4 expression e.g. by ELISA screening. Fertile transgenic plants may be assessed for gene copy number and selected lines are tested for resistance to soybean fungal pathogens in glasshouse bioassays.

Lines exhibiting increased resistance to soybean fungal and rust and insect pathogens are then assessed in field trials in infected soil and in trials where the soybean plants are artificially infected with the target fungal, insect or rust pathogens.

Example 9

Production of Transgenic Wheat Expressing HXP4

Transgenic wheat plants expressing HXP4 are produced by *Agrobacterium*-mediated transformation or by particle bombardment or other standard protocols such as those described in U.S. Pat. No. 7,785,828. Regenerated wheat plants which are PCR positive for HXP4 are assessed for levels of HXP4 expression e.g. by ELISA screening. Fertile transgenic plants may be assessed for gene copy number and selected lines are tested for resistance to wheat fungal pathogens in glasshouse bioassays.

Lines exhibiting increased resistance to wheat fungal pathogens are then assessed in field trials in infected soil and in trials where the wheat plants are artificially infected with the target fungal pathogens.

Example 10

Activity of Modified NaD1 Against the Human Fungal Pathogen *Aspergillus niger*

Recombinant NaD1 and the loop variant HXP4 were expressed in the *P. pastoris* expression system and purified as described in the methods. The anti-fungal activity of the peptides against *Aspergillus niger* was assessed as described above.

Results

Figure 12:
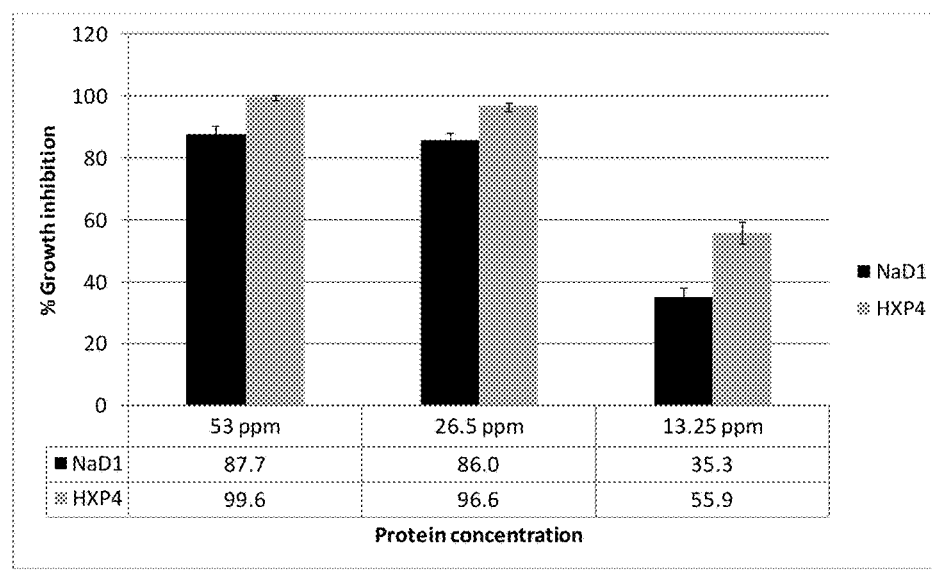

FIG. 12 illustrates the relative anti-fungal activity of the loop variant HXP4 compared to NaD1 against *A. niger*. At 13 ppm, HXP4 inhibited the growth of *A. niger* by 20.6% more than NaD1. This can be expressed as HXP4 having greater than 112% of NaD1. At 26 ppm and 53 ppm, HXP4 inhibited growth by at least 10% more than NaD1.

Example 11

Activity of Modified NaD1 Against *Cryptococcus* Spp.

Recombinant NaD1 and the loop variant HXP4 were expressed in the *P. pastoris* expression system and purified as described in the methods. The anti-fungal activity of the peptides against two strains of *Cryptococcus neoformans* and one strain of *C. gattii* was assessed as described above.

Results

Figure 13A:
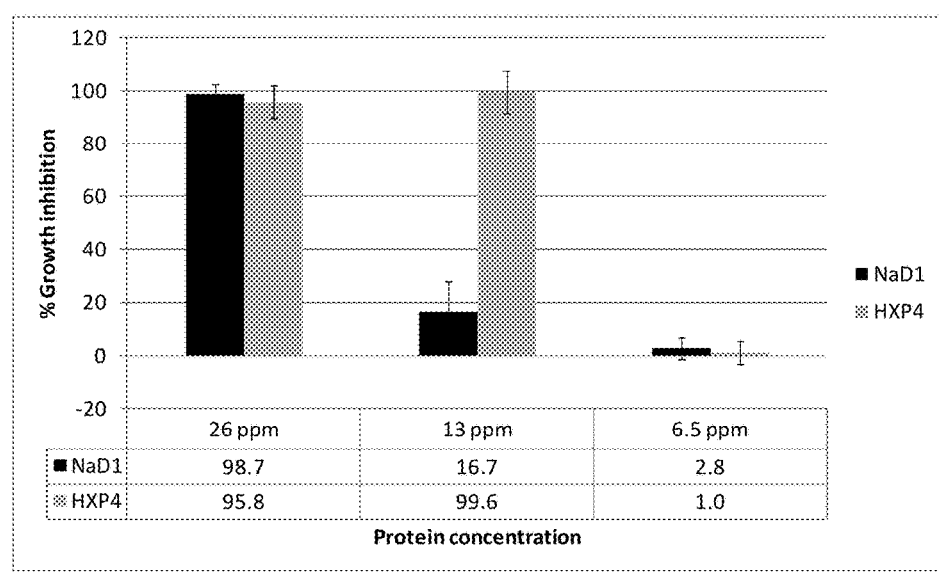
Figure 13B:
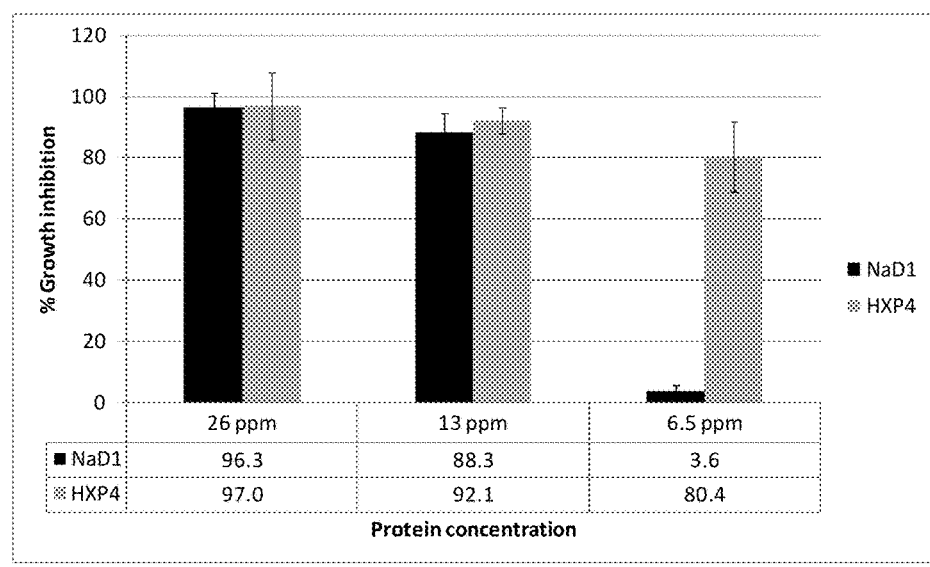
Figure 13C:
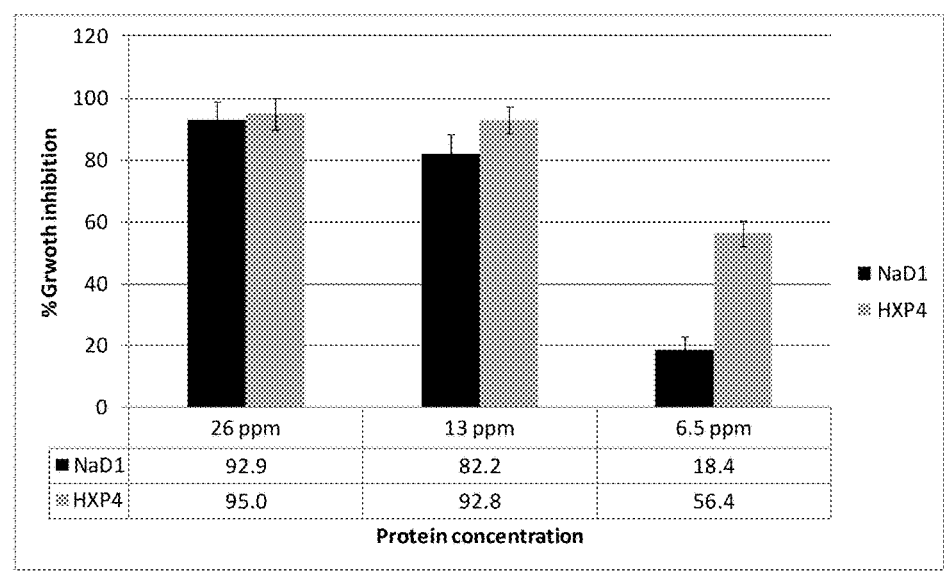

FIG. 13A illustrates the relative anti-fungal activity of the loop variant HXP4 compared to NaD1 against *Cryptococcus neoformans* (C1065). At 13 ppm, HXP4 completely inhibited growth of the yeast while NaD1 only inhibited ~16.7%. Hence, HXP4 had more than 596% of the activity of NaD1. Neither protein showed significant activity at 6.5 ppm. FIG. 13B illustrates the relative anti-fungal activity of NaD1 and HXP4 against a second strain of *C. neoformans* (C2067). At 6.5 ppm, HXP4 inhibited growth by more than 80% while NaD1 only inhibited growth by less than 4%. Against *C. gatti* (FIG. 13C), HXP4 inhibited 10% more growth than NaD1 at 13 ppm and 38% more growth than NaD1 at 6.5 ppm.

Example 12

Modification to the Loop 1B Region of the Class II Solanaceous Defensin, TPP3 as a Backbone TPP3 (SEQ ID NO: 5) is selected as the Class II solanaceous defensin backbone. This defensin comprises a Loop 1B having the amino acid sequence: QTFPGL (SEQ ID NO:15). The Loop 1B sequence is changed to that of NaD2 (HRFKGP) [SEQ ID NO:29]. The chimeric protein (HXP107) is expressed in the *P. pastoris* expression system and purified as described in the methods. The anti-fungal activity of the peptide against *Fusarium graminearum* is assessed as described in Example 1 as well as its anti-insect activity. The amino acid sequence of HXP107 is set forth in SEQ ID NO:85.

Results:

The HXP107 protein retains antifungal activity against *Fusarium graminearum* (Fgr) with an $IC_{50}$ of 0.5 µM. This compares favourably with the activity of the parent protein, TPP3, which has an $IC_{50}$ of 0.2 µM.

Example 13

Modification to the Loop 1B Region of the Class II Solanaceous Defensins, NsD1, C20 and SL549

NsD1 (SEQ ID NO:49), C20 (isolated from *Capsicum*) (SEQ ID NO:58) and SL549 (isolated from *Nicotiana*) (SEQ ID NO:59) are selected as the Class II solanaceous defensin backbone. These defensins comprise a Loop 1B having the amino acid sequence: NTFPGI (SEQ ID NO:12), KYFKGL (SEQ ID NO:60) and NTFPGI (SEQ ID NO:12), respectively. One or more of the amino acid residues in loop 1B is/are substituted by another amino acid residue. All six residues may be altered or 1 or 2 or 3 or 4 or 5 of the residues may be changed. This includes a single amino acid substitution or a Loop 1B swap. Examples of changes include the following sequences (together with the source in parentheses):

HRFKGP (NaD2); [SEQ ID NO: 29]

QHHSFP (Zea2); [SEQ ID NO: 30]

DTYRGV (PsD1); [SEQ ID NO: 31]

PTWEGI (PsD2); [SEQ ID NO: 32]

DKYRGP (MsDeF1(; [SEQ ID NO: 33]

KTFKGI (SoD2); [SEQ ID NO: 34]

KTWSGN (DmAMP1); [SEQ ID NO: 35]

EGWXGK (VrD1); [SEQ ID NO: 36]

GTWSGV (RsAFP2); and [SEQ ID NO: 37]

AGFKGP (g1-H). [SEQ ID NO: 38]

In another embodiment, the Loop 1B is substituted by a sequence selected from SEQ ID NO:67 to 79.

Recombinant loop variants are expressed in the *P. pastoris* expression system and purified as described in the methods. The anti-fungal activity of the peptides against fungal pathogens such as *Fusarium graminearum, Fusarium oxysporum, Colletotrichum graminicola* and *Fusarium* verticilloides is assessed as described in Example 1.

Example 14

Synergy of HXP4 with Protease Inhibitors Against *Fusarium graminearum* and *Colletotrichum graminicola*

DNA encoding the mature domain of the barley type-I inhibitor CI-1B (SEQ ID NO:63), the *Nicotiana alata* type I inhibitor NaPin1A, the tomato cystatin SlCys9 (SEQ ID NO:64), the rice cystatin Os1a (SEQ ID NO:65), and the barley cystatin HvCPI6 (SEQ ID NO:66) was obtained from Genscript. Inserts were excised from the pUC57 vector using Sac II and Sac I, extracted from agarose gels using the Perfectprep kit (Eppendorf) and ligated into pHUE which was then used to transform TOP10 *E. coli* cells. Plasmid DNA was isolated and then used to transform *E. coli* Rosetta-Gami B cells.

Single colonies of *E. coli* Rosetta-Gami B were used to inoculate 2YT media (10 mL, 16 g/L tryptone, 10 g/L yeast extract, 5 g/L NaCl) containing ampicillin (0.1 mg/mL), chloramphenicol (0.34 mg/mL), tetracycline (0.1 mg/mL) and kanamycin (0.05 mg/mL) and grown overnight with shaking at 37° C. This culture was used to inoculate 2YT media (500 mL) containing ampicillin (0.1 mg/mL), chloramphenicol (0.34 mg/mL), tetracycline (0.1 mg/mL)

and kanamycin (0.05 mg/mL) which was then grown for 4 h to an optical density (600 nm) of ~1.0. IPTG was then added (0.5 mM final concentration) and the culture grown for a further 16 h at 16° C. Cells were harvested by centrifugation (4,000 g at 4° C. for 20 min), resuspended in native lysis buffer (20 mL per litre cell culture, 50 mM $NaH_2PO_4$, 300 mM NaCl, 10 mM imidazole, pH 8.0) and frozen at −80° C. Cells were then thawed and treated with lysozyme (5 mg per 25 mL resuspended cells) for 20 min at 4° C. DNase I (125 uL, 2 mg/mL in 20% v/v glycerol, 75 mM NaCl) and $MgCl_2$ (125 uL, 1 M) were then added and the samples incubated at room temperature for 40 min on a rocking platform. The samples were then sonicated for 2×30 s on ice (80% w/v power, Branson sonifier 450) and centrifuged (20,000 g at 4° C. for 30 min). The hexahistidine-tagged ubiquitin-fusion proteins (His6-Ub-NaCys1,2,3) were then purified from the protein extracts by immobilized metal affinity chromatography (IMAC) under native conditions using Ni-NTA resin (1.5 mL to ~25 mL native protein extract, Qiagen) according to the manufacturer's instructions. Recombinant proteins were eluted using elution buffer (250 mM imidazole, 200 mM NaCl, 50 mM $NaH_2PO_4$, pH 8.0). The imidazole was removed by applying the eluted protein to a prepacked Sephadex G50 gel filtration column (PD-10, Amersham) equilibrated with 50 mM Tris.Cl, 100 mM NaCl, pH 8.0.

The hexahistidine-tagged ubiquitin was cleaved from the recombinant proteins using the deubiquitylating enzyme 6H.Usp2-cc (Catanzariti et al. (2004), *Protein Science* 13:1331-1339). The cleaved tag was removed by another round of IMAC with the deubiquitylated protease inhibitors as the unbound protein. This was then further purified by reversed-phase HPLC.

Recombinant CI-1B, SlCys9 and Os1a were prepared as stock solutions (20 μM) in $H_2O$. Trypsin inhibitor type I-P from bovine pancreas (Anderson and Kingston (1983), *Proc. Natl. Acad. USA* 80:6838-6842) was purchased from Sigma (T0256) and diluted to a concentration of 20 μM in $H_2O$.

The inhibitory effects of HXP4 and NaD1 in combination with serine or cysteine proteinase inhibitors on the growth of *Fusarium graminearum*, or *Colletotrichum* gramincola was measured essentially as described by Broekaert et al, supra 1990. Spores were isolated from sporulating cultures growing on synthetic nutrient poor agar (SNPB, *Fusarium graminearum*) or V8 agar (*Colletotrichum graminicola*) and counted using a hemocytometer.

Antifungal assays were conducted in 96 well microtiter trays essentially as described in Example 1. Wells were loaded with 10 μL of filter sterilized (0.22 μm syringe filter, Millipore) NaD1 (2.5 μM), HXP4 (2.5 μM) or water, along with 10 μL of filter sterilized (0.22 μm syringe filter, Millipore) proteinase inhibitor or water and 80 μL 5×10$^4$ spores/mL in ½ strength PDB. The plates were incubated at 25° C. Fungal growth was assayed by measuring optical density at 595 nm ($A_{595}$) using a microtitre plate reader (SpectraMax Pro M2; Molecular Devices). Each test was performed in quadruplicate.
Results When tested at the same concentration, HXP4 had a greater synergistic effect with protease inhibitors than NaD1 against *Fusarium graminearum*. HXP4 was also synergistic with protease inhibitors against *Colletotrichum graminicola*. Synergy calculations are presented in Tables 6 and 7 wherein Ee is the expected effect from the additive response according to Limpel's formula (Richer et al. *Pestic Sci* 19:309-315) expressed as percent inhibition and Io is the percent inhibition observed. Synergy, that is, Io values higher than Ee values was obtained with all four protease inhibitors.

Example 15

In Planta Synergy of HXP 4 with HvCPI6 Against *Fusarium graminearum*

Transgenic corn plants expressing HXP4, HvCPI6 or HXP4+HvCPI6 are created using the method described in Example 7 and are assessed for increased resistance to *Fusarium graminearum* using the bioassay described in the Methods.

FIG. 15 provides the HvCPI6 construct for expression in corn and FIG. 16 provides the HXP4+HvCPI6 construct for expression in corn.
Results Plants expressing HXP4 alone or HvCPI6 alone show no reduction in lesion area compared to plants transformed with an empty vector. Plants expressing HXP4+HvCPI6 show a 45% reduction in lesion area compared to the empty vector control (Table 9).

Example 16

Effects of HXP4 on Asian Soybean Rust

Figure 14A:
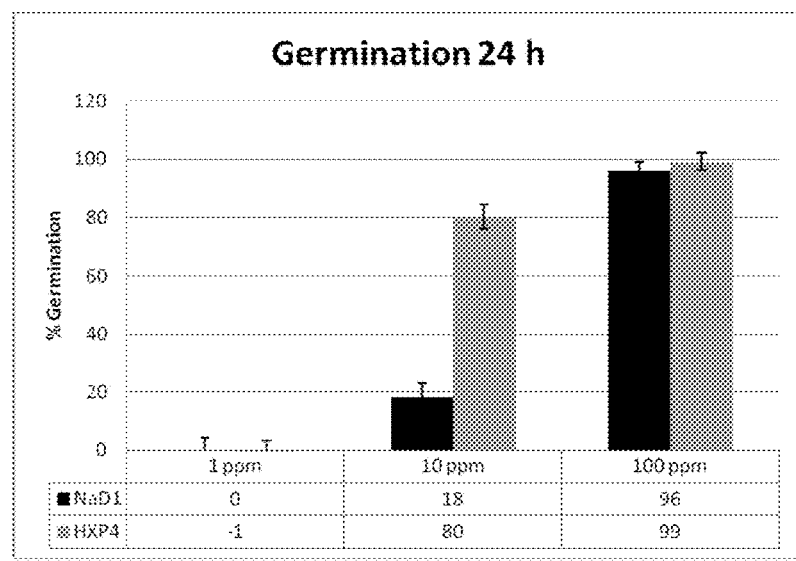
Figure 14B:
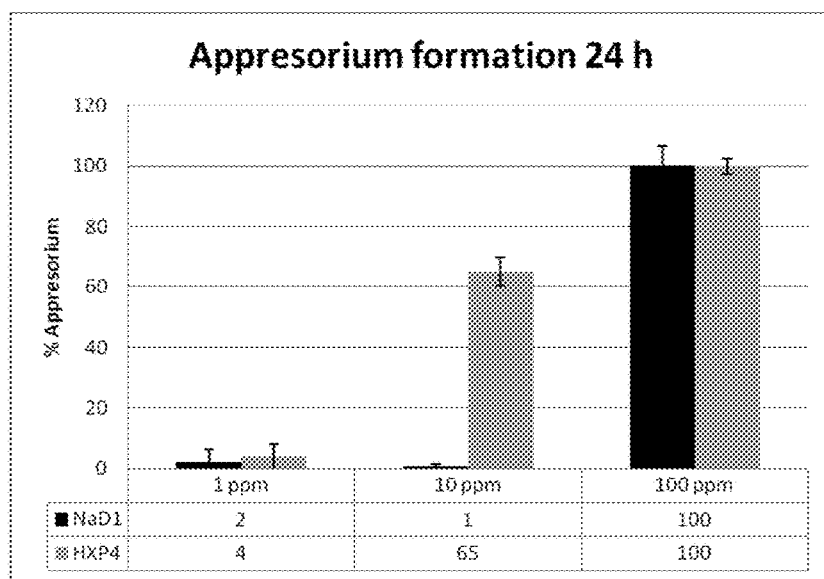
Figure 14C:
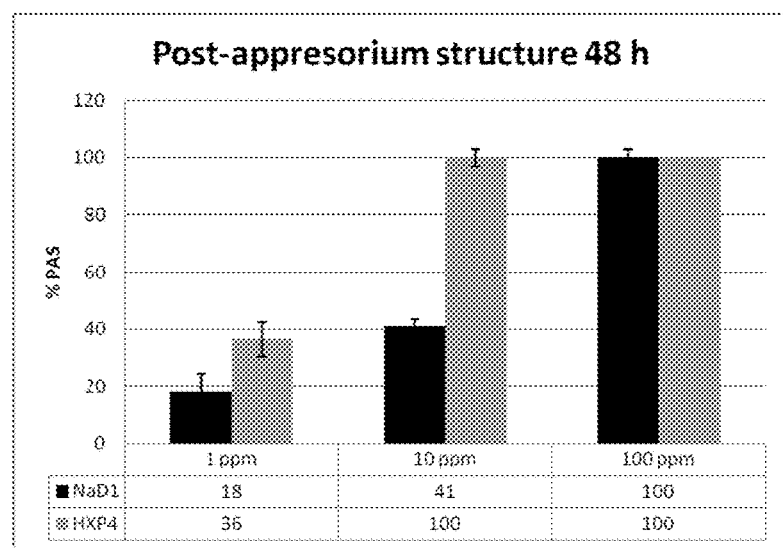

NaD1 was isolated from flowers of *Nicotiana alata* and the loop variant HXP4 was expressed in the *P. pastoris* expression system and purified as described in the methods. The effects of HXP4 on Asian soybean rust (*Phakopsora pachirhizi*) was tested and compared to NaD1. *Phakopsora pachirhizi* urediospores were grown on cellophane that was placed on an agar droplet in the presence or absence of the peptides at 100, 10, 1 and 0.1 ppm in water. Germination, appressorium formation, and formation of post-appressorial structures were evaluated using microscopy at 24 h and 48 h. Three membranes were examined per treatment and fifty isolated germlings were evaluated per membrane.
Results The effect on germination (24 hours; FIG. 14A), appresorium formation (24 hours; FIG. 14B) and formation of post-appresorium structure (48 hours; FIG. 14C) were all examined. At 10 ppm, HXP4 inhibited germination 62% more effectively than NaD1 while appresorium formation and formation of post-appresorium structures were inhibited by 65% and 59% more than NaD1, respectively.

Example 17

High-Throughput Screening to Identify Novel Loop 1B Sequences

Site directed mutagenesis of NaD1 was carried out using the Phusion (Registered Trademark) site-directed mutagenesis kit (Finnzymes). Degenerate oligonucleotide primers phosphorylated at the 5' end were designed to incorporate the random six amino acid mutation of Loop 1B.

The pHUE system was used for expression of a library of loop 1B variants. Expression and purification was modified slightly from the method described in Example 14 to enable expression in 48-well plates and purification in 96-well filter plates. The entire template plasmid (pHUE-NaD1) was amplified in a PCR reaction of 35 cycles with an annealing temperature of 66° C., 30 sec. The linear PCR product was then circularized using T4 DNA Ligase overnight at 16° C. and transformed into electro competent Rosetta-Gami B (DE3) cells according to the manufacturer's instructions.

The recovered cells were plated onto 2YT agar containing ampicillin (0.1 mg/mL), chloramphenicol (0.34 mg/mL), tetracycline (0.1 mg/mL) and kanamycin (0.015 mg/mL) and incubated at 37° C. overnight.

Single colonies were used to inoculate 150 μL of 2YT containing ampicillin (0.1 mg/mL), chloramphenicol (0.34 mg/mL), tetracycline (0.1 mg/mL) and kanamycin (0.015 mg/mL) in 96-well plates. Rosetta-Gami B (DE3) transformed with pHUE-NaD1 was included as a positive control. Plates were incubated overnight at 37° C. with constant shaking at 70% humidity. Fifty microliters of each well was transferred to 2.5 mL of 2YT antibiotics and expression and purification was performed as described in Example 13.

Proteins were tested for activity against *Colletotrichum graminicola*. Fifteen microliters of protein solution was added to 105 μL of spore solution to give a final concentration of 2×10$^4$ spores/mL in ½×Potato Dextrose Broth containing 0.5 mM CaCl$_2$, 25 mM KCl. The plates were incubated at 25° C. and fungal growth was assayed after 40 h by measuring optical density at 595 nm using a microtitre plate reader (SpectraMax Pro M5e; Molecular Devices). Proteins that inhibited fungal growth equal to or greater than the NaD1 control were identified by sequencing the plasmid DNA of the bacterial colony used for expression. A single colony identified in the screen was found to have a loop 1B sequence identical to that of NaD1. Several colonies were selected for large scale purification and testing. Proteins were expressed and as described in Example 14 and tested for activity against *Fusarium graminicola* and *Colletotrichum graminicola* as described in Example 1. Loop 1B sequences identified are listed in Table 10.

TABLE 6

Synergistic effect of HXP4 vs NaD1 in combination with proteinase inhibitors against Fgr

| Protease inhibitor | HXP4 Ee | HXP4 Io | NaD1 Ee | NaD1 Io |
|---|---|---|---|---|
| CI-1B | 12.1 | 81.1 | 17.1 | 27.3 |
| SlCys9 | 0.0 | 86.0 | 0.0 | 37.6 |
| Oc1a | 0.0 | 90.7 | 0.0 | 11.3 |
| BTPI | 2.0 | 81.0 | 2.0 | 5.0 |

TABLE 7

Synergistic effect of HXP4 in combination with proteinase inhibitors against Cgr

| Protease inhibitor | HXP4 Ee | HXP4 Io |
|---|---|---|
| BPTI | 16.7 | 97.1 |
| NaPin1A | 11.8 | 69.3 |
| HvCPI6 | 13.8 | 100.0 |
| SlCys9 | 15.4 | 94.9 |

TABLE 8

Protection of transgenic corn plants expressing HXP4 or NaD1 against Cgr

| Protein | Percent inhibition relative of empty vector control | P-value |
|---|---|---|
| HXP4 | 26 | 0.029 |
| NaD1 | 0 | 0.997 |

TABLE 9

Protection of transgenic corn plants expression HXP4 in combination with HvCPI6 against Fgr

| Protein | Percent inhibition relative of empty vector control | P-value |
|---|---|---|
| HXP4 | 0 | 0.183 |
| HvCPI6 | 0 | 0.697 |
| HXP4 + HvCPI6 | 45 | <0.001 |

TABLE 10

Loop 1B sequences from proteins that inhibit the growth of Colletotrichum graminicola

LSAKMV
(SEQ ID NO: 88)

LSFKGT
(SEQ ID NO: 67)

LVFGGM
(SEQ ID NO: 68)

YNPVGL
(SEQ ID NO: 69)

LFWEKS
(SEQ ID NO: 70)

SPFVGP
(SEQ ID NO: 71)

FINRDW
(SEQ ID NO: 89)

SIIASA
(SEQ ID NO: 72)

IKAPGW
(SEQ ID NO: 73)

LTLSNH
(SEQ ID NO: 74)

LISFYP
(SEQ ID NO: 75)

LVSFPG
(SEQ ID NO: 90)

ALFAGE
(SEQ ID NO: 76)

TABLE 10-continued

Loop 1B sequences from proteins that inhibit the growth of Colletotrichum graminicola

FLYREK
(SEQ ID NO: 77)

FIFRME
(SEQ ID NO: 78)

HAFQKG
(SEQ ID NO: 79)

Those skilled in the art will appreciate that the disclosure described herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations of any two or more of these steps or features.

BIBLIOGRAPHY

Altschul et al. (1997) *Nucl. Acids. Res.* 25: 3389
Anderson and Kingston (1983), *Proc. Natl. Acad. USA* 80:6838-6842, 1983
Ausubel et al. (1994-1998) (In: *Current Protocols in Molecular Biology*, John Wiley & Sons Inc.
Berrocal-Lobo et al. (2002) *Plant Physiol* 128(3):951-961
Bevan (1984) *Nucleic Acids Research* 12:8711-8721
Bloch and Richardson (1991) *FEBS Lett* 279(1):101-104
Bonner and Laskey (1974) *Eur J Biochem* 46:83-88
Broekaert et al. (1990) *FEMS Microbiol Lett* 69:55-60
Catanzariti et al. (2004) *Protein Science* 13:1331-1339
Chang et al. (2005) *Mol Biol Cell* 16(10):4941-4953
Colilla et al. (1990) *FEBS Lett* 270(1-2):191-194
De Samblanx et al. (1997) *J Biol Chem* 272(2):1171-1179
Frame et al. (2002) *Plant Physiol* 129:13-22
Gao et al. (2000) *Nat Biotechnol* 18(12):1307-1310
Janssen et al. (2003) *Biochemistry* 42(27):8214-8222
Jha et al., (2009) *Transgenic Res* 18(1):59-69
Jones and Dangl (2006) *Nature* 444(7117):323-329
Lay et al. (2003) *Plant Physiol* 131(3):1283-1293
Li and Asiegbu (2004) *J Plant Res* 117(2):155-162
Lin et al (2007) *Proteins* 68(2):530-540
Marmur and Doty (1962) *J Mol Biol* 5:109-118
Metlen et al. (2009) *Plant Cell Environ* 32(6):641-653
Nurnberger et al. (2004) *Immunol Rev* 198:249-266
Richer (1987) *Pestic Sci* 19:309-315
Schaaper et al. (2001) *J. Pept. Res.* 57(5):409-418
Showalter (1993) *Plant Cell* 5(1):9-23
Spelbrink et al. (2004) *Plant Physiol* 135(4):2055-2067
van der Weerden et al. (2008)*J Biol Chem* 283(21):14445-14452
Wisconsin Genetics Software Package Release 7.0, Genetics Computer Group, 575 Science Drive Madison, Wis., USA
Yount and Yeaman (2005) *Protein Pept Lett* 12(1):49-67

The invention claimed is:

1. An isolated polynucleotide encoding an artificially modified solanaceous Class II defensin polypeptide, wherein the polypeptide comprises at least 90% identity to the amino acid sequence of NaD1 set forth in SEQ ID NO: 2 with the Loop IB amino acid sequence at positions 8-13 of SEQ ID NO: 2 replaced by an exogenous Loop IB amino acid sequence selected from the group consisting of SEQ ID NOs: 29, 30 and 31.

2. The isolated polynucleotide encoding the modified solanaceous Class II defensin polypeptide of claim 1, wherein the Loop IB amino acid sequence is replaced by the endogenous Loop IB amino acid sequence of SEQ ID NO:29.

3. The isolated polynucleotide encoding the modified solanaceous Class II defensin polypeptide of claim 1, wherein the polypeptide is selected from the group consisting of SEQ ID NO:39 (HXP4), SEQ ID NO:40 (HXP34) and SEQ ID NO:41 (HXP35).

4. The isolated polynucleotide encoding the modified solanaceous Class II defensin polypeptide of claim 1, wherein the polypeptide comprises the amino acid sequence of NaD1 set forth in SEQ ID NO: 2 with the Loop IB amino acid sequence at positions 8-13 of SEQ ID NO: 2 replaced by an exogenous Loop IB amino acid sequence selected from the group consisting of SEQ ID NOs: 29, 30 and 31.

5. The isolated polynucleotide encoding the modified solanaceous Class II defensin polypeptide of claim 4, wherein the Loop IB amino acid sequence is replaced by the exogenous Loop IB amino acid sequence SEQ ID NO: 29.

6. A genetic construct comprising the polynucleotide of claim 1.

7. A genetically modified plant comprising the polynucleotide of claim 1 or genetic construct of claim 6 or progeny of said plant wherein the plant or its progeny expresses the polynucleotide to produce the artificially modified solanaceous Class II defensin polypeptide.

8. The genetically modified plant of claim 7, selected from the group consisting of corn, soybean, cotton, sorghum, wheat, barley, maize, canola, abaca, alfalfa, almond, apple, asparagus, banana, bean-*phaseolus*, blackberry, broad bean, cashew, cassava, chickpea, citrus, coconut, coffee, fig, flax, grapes, groundnut, hemp, lavender, mushroom, olive, onion, pea, peanut, pear, pearl millet, potato, rapeseed, ryegrass, strawberry, sugarbeet, sugarcane, sunflower, sweet potato, taro, tea, tobacco, tomato, triticale, truffle and yam.

9. A method for generating a genetically modified plant which exhibits anti-fungal activity as a result of the genetic modification, the method comprising creating a plant which comprises cells which express the nucleic acid encoding the polypeptide of claim 1, the level of expression in the plant sufficient for the modified defensin to exhibit a protective effect against a plant fungal pathogen.

10. The isolated polynucleotide of claim 1, wherein said identity is at least 95%.

* * * * *

SEQUENCE LISTING

```
<160> NUMBER OF SEQ ID NOS: 91

<210> SEQ ID NO 1
<211> LENGTH: 6
<212> TYPE: PRT
<213> ORGANISM: Artificial Sequence
<220> FEATURE:
<223> OTHER INFORMATION: Synthetic construct:  Generic amino acid
      sequence of Loop 1B region
<220> FEATURE:
<221> NAME/KEY: MISC_FEATURE
<222> LOCATION: (1)..(1)
<223> OTHER INFORMATION: Xaa = A, R, N, D, C, Q, E, G, H, I, L, K, M,
      F, P, S, T, W, Y or V or a naturally occurring modified form
      thereof
<220> FEATURE:
<221> NAME/KEY: MISC_FEATURE
<222> LOCATION: (2)..(2)
<223> OTHER INFORMATION: Xaa = A, R, N, D, C, Q, E, G, H, I, L, K, M,
      F, P, S, T, W, Y or V or a naturally occurring modified form
      thereof
<220> FEATURE:
<221> NAME/KEY: MISC_FEATURE
<222> LOCATION: (3)..(3)
<223> OTHER INFORMATION: Xaa = A, R, N, D, C, Q, E, G, H, I, L, K, M,
      F, P, S, T, W, Y or V or a naturally occurring modified form
      thereof
<220> FEATURE:
<221> NAME/KEY: MISC_FEATURE
<222> LOCATION: (4)..(4)
<223> OTHER INFORMATION: Xaa = A, R, N, D, C, Q, E, G, H, I, L, K, M,
      F, P, S, T, W, Y or V or a naturally occurring modified form
      thereof
<220> FEATURE:
<221> NAME/KEY: MISC_FEATURE
<222> LOCATION: (5)..(5)
<223> OTHER INFORMATION: Xaa = A, R, N, D, C, Q, E, G, H, I, L, K, M,
      F, P, S, T, W, Y or V or a naturally occurring modified form
      thereof
```

-continued

```
<220> FEATURE:
<221> NAME/KEY: MISC_FEATURE
<222> LOCATION: (6)..(6)
<223> OTHER INFORMATION: Xaa = A, R, N, D, C, Q, E, G, H, I, L, K, M,
      F, P, S, T, W, Y or V or a naturally occurring modified form
      thereof

<400> SEQUENCE: 1

Xaa Xaa Xaa Xaa Xaa Xaa
1               5

<210> SEQ ID NO 2
<211> LENGTH: 47
<212> TYPE: PRT
<213> ORGANISM: Artificial Sequence
<220> FEATURE:
<223> OTHER INFORMATION: Synthetic construct: Amino acid sequence of
      portion of NaD1 (Nicotiana alata) containing Loop 1B

<400> SEQUENCE: 2

Arg Glu Cys Lys Thr Glu Ser Asn Thr Phe Pro Gly Ile Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 3
<211> LENGTH: 47
<212> TYPE: PRT
<213> ORGANISM: Artificial Sequence
<220> FEATURE:
<223> OTHER INFORMATION: Synthetic construct: Amino acid sequence of
      portion of PhD1 (Petunia hybrida) containing Loop 1B

<400> SEQUENCE: 3

Ala Thr Cys Lys Ala Glu Cys Pro Thr Trp Asp Ser Val Cys Ile Asn
1               5                   10                  15

Lys Lys Pro Cys Val Ala Cys Cys Lys Lys Ala Lys Phe Ser Asp Gly
            20                  25                  30

His Cys Ser Lys Ile Leu Arg Arg Cys Leu Cys Thr Lys Glu Cys
        35                  40                  45

<210> SEQ ID NO 4
<211> LENGTH: 49
<212> TYPE: PRT
<213> ORGANISM: Artificial Sequence
<220> FEATURE:
<223> OTHER INFORMATION: Synthetic construct: Amino acid sequence of
      portion of PhD2 (Petunia hybrida) containing Loop 1B

<400> SEQUENCE: 4

Gly Thr Cys Lys Ala Glu Cys Pro Thr Trp Glu Gly Ile Cys Ile Asn
1               5                   10                  15

Lys Ala Pro Cys Val Lys Cys Cys Lys Ala Gln Pro Glu Lys Phe Thr
            20                  25                  30

Asp Gly His Cys Ser Lys Ile Leu Arg Arg Cys Leu Cys Thr Lys Pro
        35                  40                  45

Cys

<210> SEQ ID NO 5
<211> LENGTH: 48
<212> TYPE: PRT
<213> ORGANISM: Artificial Sequence
```

```
<220> FEATURE:
<223> OTHER INFORMATION: Synthetic construct: Amino acid sequence of
      portion of TPP3 (Solanum lycopersicum) containing Loop 1B

<400> SEQUENCE: 5

Gln Gln Ile Cys Lys Ala Pro Ser Gln Thr Phe Pro Gly Leu Cys Phe
1               5                   10                  15

Met Asp Ser Ser Cys Arg Lys Tyr Cys Ile Lys Glu Lys Phe Thr Gly
                20                  25                  30

Gly His Cys Ser Lys Leu Gln Arg Lys Cys Leu Cys Thr Lys Pro Cys
            35                  40                  45

<210> SEQ ID NO 6
<211> LENGTH: 47
<212> TYPE: PRT
<213> ORGANISM: Artificial Sequence
<220> FEATURE:
<223> OTHER INFORMATION: Synthetic construct: Amino acid sequence of
      portion of FST (Nicotiana tabacum) containing Loop 1B

<400> SEQUENCE: 6

Arg Glu Cys Lys Thr Glu Ser Asn Thr Phe Pro Gly Ile Cys Ile Thr
1               5                   10                  15

Lys Pro Pro Cys Arg Lys Ala Cys Ile Ser Glu Lys Phe Thr Asp Gly
                20                  25                  30

His Cys Ser Lys Leu Leu Arg Arg Cys Leu Cys Thr Lys Pro Cys
            35                  40                  45

<210> SEQ ID NO 7
<211> LENGTH: 45
<212> TYPE: PRT
<213> ORGANISM: Artificial Sequence
<220> FEATURE:
<223> OTHER INFORMATION: Synthetic construct: Amino acid sequence of
      portion of g-thionin (Nicotiana excelsior) containing Loop B1
      [NeThio1]

<400> SEQUENCE: 7

Arg Glu Cys Ala Arg Glu Ile Phe Thr Gly Leu Cys Ile Thr Asn Pro
1               5                   10                  15

Gln Cys Arg Lys Ala Cys Ile Lys Glu Lys Phe Thr Asp Gly His Cys
                20                  25                  30

Ser Lys Ile Leu Arg Arg Cys Leu Cys Thr Lys Pro Cys
            35                  40                  45

<210> SEQ ID NO 8
<211> LENGTH: 47
<212> TYPE: PRT
<213> ORGANISM: Artificial Sequence
<220> FEATURE:
<223> OTHER INFORMATION: Synthetic construct: Amino acid sequence of
      portion of g-thionin (Nicotiana excelsior) containing Loop 1B
      [NeThio2]

<400> SEQUENCE: 8

Lys Asp Cys Lys Thr Glu Ser Asn Thr Phe Pro Gly Ile Cys Ile Thr
1               5                   10                  15

Lys Pro Pro Cys Arg Lys Ala Cys Ile Lys Glu Lys Phe Thr Asp Gly
                20                  25                  30

His Cys Ser Lys Ile Leu Arg Arg Cys Leu Cys Thr Lys Pro Cys
            35                  40                  45

<210> SEQ ID NO 9
```

```
<211> LENGTH: 48
<212> TYPE: PRT
<213> ORGANISM: Artificial Sequence
<220> FEATURE:
<223> OTHER INFORMATION: Synthetic construct:  Amino acid sequence of
      portion of g-thionin (Nicotiana attenuata) containing Loop 1B
      [Na-gth]

<400> SEQUENCE: 9

Lys Ser Thr Cys Lys Ala Glu Ser Asn Thr Phe Glu Gly Phe Cys Val
1               5                   10                  15

Thr Lys Pro Pro Cys Arg Arg Ala Cys Leu Lys Glu Lys Phe Thr Asp
            20                  25                  30

Gly Lys Cys Ser Lys Ile Leu Arg Arg Cys Ile Cys Tyr Lys Pro Cys
        35                  40                  45

<210> SEQ ID NO 10
<211> LENGTH: 48
<212> TYPE: PRT
<213> ORGANISM: Artificial Sequence
<220> FEATURE:
<223> OTHER INFORMATION: Synthetic construct:  Amino acid sequence of
      portion of g-thionin (Nicotiana paniculata) containing Loop 1B
      [NpThio1]

<400> SEQUENCE: 10

Lys Ser Thr Cys Lys Ala Glu Ser Asn Thr Phe Pro Gly Leu Cys Ile
1               5                   10                  15

Thr Lys Pro Pro Cys Arg Lys Ala Cys Leu Ser Glu Lys Phe Thr Asp
            20                  25                  30

Gly Lys Cys Ser Lys Ile Leu Arg Arg Cys Ile Cys Tyr Lys Pro Cys
        35                  40                  45

<210> SEQ ID NO 11
<211> LENGTH: 50
<212> TYPE: PRT
<213> ORGANISM: Artificial Sequence
<220> FEATURE:
<223> OTHER INFORMATION: Synthetic construct:  Amino acid sequence of
      portion of g-thionin (Capicum chinense) containing Loop 1B
      [Cc-gth]

<400> SEQUENCE: 11

Gln Asn Asn Ile Cys Lys Thr Thr Ser Lys His Phe Lys Gly Leu Cys
1               5                   10                  15

Phe Ala Asp Ser Lys Cys Arg Lys Val Cys Ile Gln Glu Asp Lys Phe
            20                  25                  30

Glu Asp Gly His Cys Ser Lys Leu Gln Arg Lys Cys Leu Cys Thr Lys
        35                  40                  45

Asn Cys
    50

<210> SEQ ID NO 12
<211> LENGTH: 6
<212> TYPE: PRT
<213> ORGANISM: Artificial Sequence
<220> FEATURE:
<223> OTHER INFORMATION: Synthetic construct:  Amino acid sequence of
      Loop 1B from NaD1

<400> SEQUENCE: 12

Asn Thr Phe Pro Gly Ile
1               5
```

```
<210> SEQ ID NO 13
<211> LENGTH: 6
<212> TYPE: PRT
<213> ORGANISM: Artificial Sequence
<220> FEATURE:
<223> OTHER INFORMATION: Synthetic construct:  Amino acid sequence of
      Loop 1B from PhD1

<400> SEQUENCE: 13

Pro Thr Trp Asp Ser Val
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic construct:  Amino acid sequence of
      Loop 1B from PhD2

<400> SEQUENCE: 14

Pro Thr Trp Glu Gly Ile
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic construct:  Amino acid sequence
      of Loop 1B TPP3

<400> SEQUENCE: 15

Gln Thr Phe Pro Gly Leu
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic construct:  Amino acid sequence
      of Loop 1B FST

<400> SEQUENCE: 16

Asn Thr Phe Pro Gly Ile
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic construct:  Amino acid sequence
      of Loop 1B g-thionin (N. excelsior) [NeThio1]

<400> SEQUENCE: 17

Ile Phe Thr Gly Leu
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic construct:  Amino acid sequence
      of Loop 1B g-thionin (N. excelsior) [NeThio2]

<400> SEQUENCE: 18
```

```
Asn Thr Phe Pro Gly Ile
1               5
```

<210> SEQ ID NO 19
<211> LENGTH: 6
<212> TYPE: PRT
<213> ORGANISM: Artificial Sequence
<220> FEATURE:
<223> OTHER INFORMATION: Synthetic construct: Amino acid sequence
      of Loop 1B g-thionin (N. attenuata) [Na-gth]

<400> SEQUENCE: 19

```
Asn Thr Phe Glu Gly Phe
1               5
```

<210> SEQ ID NO 20
<211> LENGTH: 6
<212> TYPE: PRT
<213> ORGANISM: Artificial Sequence
<220> FEATURE:
<223> OTHER INFORMATION: Synthetic construct: Amino acid sequence
      of Loop 1B g-thionin (N. paniculata) [NpThio1]

<400> SEQUENCE: 20

```
Asn Thr Phe Pro Gly Leu
1               5
```

<210> SEQ ID NO 21
<211> LENGTH: 6
<212> TYPE: PRT
<213> ORGANISM: Artificial Sequence
<220> FEATURE:
<223> OTHER INFORMATION: Synthetic construct: Amino acid sequence
      of Loop 1B g-thionin (C. chinense) [Cc-gth]

<400> SEQUENCE: 21

```
Lys His Phe Lys Gly Leu
1               5
```

<210> SEQ ID NO 22
<211> LENGTH: 47
<212> TYPE: PRT
<213> ORGANISM: Artificial Sequence
<220> FEATURE:
<223> OTHER INFORMATION: Synthetic construct: Amino acid
      sequence of defensin NaD2 containing Loop 1B

<400> SEQUENCE: 22

```
Arg Thr Cys Glu Ser Gln Ser His Arg Phe Lys Gly Pro Cys Ala Arg
1               5                   10                  15

Asp Ser Asn Cys Ala Thr Val Cys Leu Thr Glu Gly Phe Ser Gly Gly
            20                  25                  30

Asp Cys Arg Gly Phe Arg Arg Arg Cys Phe Cys Thr Arg Pro Cys
        35                  40                  45
```

<210> SEQ ID NO 23
<211> LENGTH: 47
<212> TYPE: PRT
<213> ORGANISM: Artificial Sequence
<220> FEATURE:
<223> OTHER INFORMATION: Synthetic construct: Amino acid
      sequence of defensin g1-H containing Loop 1B

<400> SEQUENCE: 23

```
Arg Ile Cys Arg Arg Arg Ser Ala Gly Phe Lys Gly Pro Cys Val Ser
1               5                   10                  15
```

Asn Lys Asn Cys Ala Gln Val Cys Met Gln Glu Gly Trp Gly Gly Gly
                20                  25                  30

Asn Cys Asp Gly Pro Leu Arg Arg Cys Lys Cys Met Arg Arg Cys
            35                  40                  45

<210> SEQ ID NO 24
<211> LENGTH: 46
<212> TYPE: PRT
<213> ORGANISM: Artificial Sequence
<220> FEATURE:
<223> OTHER INFORMATION: Synthetic construct: Amino acid
      sequence of defensin Psd1 containing Loop 1B

<400> SEQUENCE: 24

Lys Thr Cys Glu His Leu Ala Asp Thr Tyr Arg Gly Val Cys Phe Thr
1               5                   10                  15

Asn Ala Ser Cys Asp Asp His Cys Lys Asn Lys Ala His Leu Ile Ser
                20                  25                  30

Gly Thr Cys His Asn Trp Lys Cys Phe Cys Thr Gln Asn Cys
            35                  40                  45

<210> SEQ ID NO 25
<211> LENGTH: 45
<212> TYPE: PRT
<213> ORGANISM: Artificial Sequence
<220> FEATURE:
<223> OTHER INFORMATION: Synthetic construct: Amino acid
      sequence of defensin MsDef1 containing Loop 1B

<400> SEQUENCE: 25

Arg Thr Cys Glu Asn Leu Ala Asp Lys Tyr Arg Gly Pro Cys Phe Ser
1               5                   10                  15

Gly Cys Asp Thr His Cys Thr Thr Lys Glu Asn Ala Val Ser Gly Arg
                20                  25                  30

Cys Arg Asp Asp Phe Arg Cys Trp Cys Thr Lys Arg Cys
            35                  40                  45

<210> SEQ ID NO 26
<211> LENGTH: 50
<212> TYPE: PRT
<213> ORGANISM: Artificial Sequence
<220> FEATURE:
<223> OTHER INFORMATION: Synthetic construct: Amino acid
      sequence of defensin DmAMP1 containing Loop 1B

<400> SEQUENCE: 26

Glu Leu Cys Glu Lys Ala Ser Lys Thr Trp Ser Gly Asn Cys Gly Asn
1               5                   10                  15

Thr Gly His Cys Asp Asn Gln Cys Lys Ser Trp Glu Gly Ala Ala His
                20                  25                  30

Gly Ala Cys His Val Arg Asn Gly Lys His Met Cys Phe Cys Tyr Phe
            35                  40                  45

Asn Cys
    50

<210> SEQ ID NO 27
<211> LENGTH: 51
<212> TYPE: PRT
<213> ORGANISM: Artificial Sequence
<220> FEATURE:
<223> OTHER INFORMATION: Synthetic construct: Amino acid
      sequence of defensin RsAFP2 containing Loop 1B

<400> SEQUENCE: 27

Gln Lys Leu Cys Gln Arg Pro Ser Gly Thr Trp Ser Gly Val Cys Gly
1               5                   10                  15

Asn Asn Asn Ala Cys Lys Asn Gln Cys Ile Arg Leu Glu Lys Ala Arg
                20                  25                  30

His Gly Ser Cys Asn Tyr Val Phe Pro Ala His Lys Cys Ile Cys Tyr
            35                  40                  45

Phe Pro Cys
    50

<210> SEQ ID NO 28
<211> LENGTH: 47
<212> TYPE: PRT
<213> ORGANISM: Artificial Sequence
<220> FEATURE:
<223> OTHER INFORMATION: Synthetic construct: Amino
      acid sequence of defensin g-zeathionin2 (Zea2) containing Loop 1B

<400> SEQUENCE: 28

Arg Val Cys Met Gly Lys Ser Gln His His Ser Phe Pro Cys Ile Ser
1               5                   10                  15

Asp Arg Leu Cys Ser Asn Glu Cys Val Lys Glu Asp Gly Gly Trp Thr
                20                  25                  30

Ala Gly Tyr Cys His Leu Arg Tyr Cys Arg Cys Gln Lys Ala Cys
            35                  40                  45

<210> SEQ ID NO 29
<211> LENGTH: 6
<212> TYPE: PRT
<213> ORGANISM: Artificial Sequence
<220> FEATURE:
<223> OTHER INFORMATION: Synthetic construct: Amino acid sequence of
      Loop 1B from NaD2

<400> SEQUENCE: 29

His Arg Phe Lys Gly Pro
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic construct: Amino acid sequence of
      Loop 1B from Zea2

<400> SEQUENCE: 30

Gln His His Ser Phe Pro
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic construct: Amino acid sequence of
      Loop 1B from PsD1

<400> SEQUENCE: 31

Asp Thr Tyr Arg Gly Val
1               5

<210> SEQ ID NO 32
<211> LENGTH: 6

```
<212> TYPE: PRT
<213> ORGANISM: Artificial Sequence
<220> FEATURE:
<223> OTHER INFORMATION: Synthetic construct: Amino acid sequence of
      Loop 1B from PsD2

<400> SEQUENCE: 32

Pro Thr Trp Glu Gly Ile
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic construct: Amino acid sequence of
      Loop 1B from MsDef1

<400> SEQUENCE: 33

Asp Lys Tyr Arg Gly Pro
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic construct: Amino acid sequence of
      Loop 1B from SoD2

<400> SEQUENCE: 34

Lys Thr Phe Lys Gly Ile
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic construct: Amino acid sequence of
      Loop 1B from DmAMP1

<400> SEQUENCE: 35

Lys Thr Trp Ser Gly Asn
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic construct: Amino acid sequence of
      Loop 1B from VrD1
<220> FEATURE:
<221> NAME/KEY: MISC_FEATURE
<222> LOCATION: (3)..(3)
<223> OTHER INFORMATION: X = any amino acid

<400> SEQUENCE: 36

Glu Gly Xaa Gly Lys
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic construct: Amino acid sequence of
      Loop 1B from RsAFP2
```

<400> SEQUENCE: 37

Gly Thr Trp Ser Gly Val
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic construct:  Amino acid sequence of
      Loop 1B from g1-H

<400> SEQUENCE: 38

Ala Gly Phe Lys Gly Pro
1               5

<210> SEQ ID NO 39
<211> LENGTH: 47
<212> TYPE: PRT
<213> ORGANISM: Artificial Sequence
<220> FEATURE:
<223> OTHER INFORMATION: Synthetic construct:  Amino acid sequence of
      HXP4 (NaD2 Loop 1B [NaD2L1B] in NaD1)

<400> SEQUENCE: 39

Arg Glu Cys Lys Thr Glu Ser His Arg Phe Lys Gly Pro Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 40
<211> LENGTH: 47
<212> TYPE: PRT
<213> ORGANISM: Artificial Sequence
<220> FEATURE:
<223> OTHER INFORMATION: Synthetic construct:  Amino acid sequence of
      HXP34 (Zea2 Loop 1B [Zea2L1B] in NaD1)

<400> SEQUENCE: 40

Arg Glu Cys Lys Thr Glu Ser Gln His His Ser Phe Pro Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 41
<211> LENGTH: 47
<212> TYPE: PRT
<213> ORGANISM: Artificial Sequence
<220> FEATURE:
<223> OTHER INFORMATION: Synthetic construct:  Amino acid sequence of
      HXP35 (PsD1 Loop 1B [PsDL1B] in NaD1)

<400> SEQUENCE: 41

Arg Glu Cys Lys Thr Glu Ser Asp Thr Tyr Arg Gly Val Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 42
<211> LENGTH: 47
<212> TYPE: PRT
<213> ORGANISM: Artificial Sequence
<220> FEATURE:
<223> OTHER INFORMATION: Synthetic construct: Amino acid sequence
      of HXP91 (MsDeF1 Loop 1B [MsDef1L1B] in NaD1)

<400> SEQUENCE: 42

Arg Glu Cys Lys Thr Glu Ser Asp Lys Tyr Arg Gly Pro Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 43
<211> LENGTH: 47
<212> TYPE: PRT
<213> ORGANISM: Artificial Sequence
<220> FEATURE:
<223> OTHER INFORMATION: Synthetic construct: Amino acid sequence of
      HXP92 (SoD1 Loop 1B [SoD1L1B] in NaD1)

<400> SEQUENCE: 43

Arg Glu Cys Lys Thr Glu Ser Lys Thr Phe Lys Gly Ile Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 44
<211> LENGTH: 47
<212> TYPE: PRT
<213> ORGANISM: Artificial Sequence
<220> FEATURE:
<223> OTHER INFORMATION: Synthetic construct: Amino acid sequence
      of HXP58 (DmAMP1 Loop 1B [DMAMPL1B] in NaD1)

<400> SEQUENCE: 44

Arg Glu Cys Lys Thr Glu Ser Lys Thr Trp Ser Gly Asn Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 45
<211> LENGTH: 47
<212> TYPE: PRT
<213> ORGANISM: Artificial Sequence
<220> FEATURE:
<223> OTHER INFORMATION: Synthetic construct: Amino acid sequence of
      HXP37 (VrD1 Loop 1B [VrD1L1B] in NaD1)
<220> FEATURE:
<221> NAME/KEY: MISC_FEATURE
<222> LOCATION: (11)..(11)
<223> OTHER INFORMATION: X = any amino acid

<400> SEQUENCE: 45

Arg Glu Cys Lys Thr Glu Ser Glu Gly Trp Xaa Gly Lys Cys Ile Thr
1               5                   10                  15

```
Lys Pro Pro Cys Arg Lys Ala Cys Ile Ser Glu Lys Phe Thr Asp Gly
                20                  25                  30

His Cys Ser Lys Ile Leu Arg Arg Cys Leu Cys Thr Lys Pro Cys
        35                  40                  45

<210> SEQ ID NO 46
<211> LENGTH: 49
<212> TYPE: PRT
<213> ORGANISM: Artificial Sequence
<220> FEATURE:
<223> OTHER INFORMATION: Synthetic construct:  Amino acid sequence of
      HXP72 (NaD2 Loop 1B [NaD2L1B] in PhD2)

<400> SEQUENCE: 46

Gly Thr Cys Lys Ala Glu Cys His Arg Phe Lys Gly Pro Cys Ile Asn
1               5                   10                  15

Lys Ala Pro Cys Val Lys Cys Cys Lys Ala Gln Pro Glu Lys Phe Thr
                20                  25                  30

Asp Gly His Cys Ser Lys Ile Leu Arg Arg Cys Leu Cys Thr Lys Pro
        35                  40                  45

Cys

<210> SEQ ID NO 47
<211> LENGTH: 47
<212> TYPE: PRT
<213> ORGANISM: Artificial Sequence
<220> FEATURE:
<223> OTHER INFORMATION: Synthetic construct:  Amino acid sequence of
      HXP95 (NaD2 Loop 1B [NaD2L1B] in NsD1

<400> SEQUENCE: 47

Lys Asp Cys Lys Arg Glu Ser His Arg Phe Lys Gly Pro Cys Ile Thr
1               5                   10                  15

Lys Leu Pro Cys Arg Arg Ala Cys Ile Ser Glu Lys Phe Ala Asp Gly
                20                  25                  30

His Cys Ser Lys Ile Leu Arg Arg Cys Leu Cys Thr Lys Pro Cys
        35                  40                  45

<210> SEQ ID NO 48
<211> LENGTH: 141
<212> TYPE: DNA
<213> ORGANISM: Artificial Sequence
<220> FEATURE:
<223> OTHER INFORMATION: Synthetic construct:  Nucleotide
      sequence encoding defensin from Nicotiana suaveolens

<400> SEQUENCE: 48
aaagattgca aaagagaaag caatacattc cctggaatat gcattaccaa accaccatgc       60
agaaaagctt gtatccgtga gaaatttact gatggtcatt gtagcaaaat cctcagaaga      120
tgtctatgca ctaagccatg t                                                141

<210> SEQ ID NO 49
<211> LENGTH: 47
<212> TYPE: PRT
<213> ORGANISM: Artificial Sequence
<220> FEATURE:
<223> OTHER INFORMATION: Synthetic construct: Amino acid sequence of
      NsD1

<400> SEQUENCE: 49

Lys Asp Cys Lys Arg Glu Ser Asn Thr Phe Pro Gly Ile Cys Ile Thr
1               5                   10                  15
```

Lys Pro Pro Cys Arg Lys Ala Cys Ile Arg Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 50
<211> LENGTH: 141
<212> TYPE: DNA
<213> ORGANISM: Artificial Sequence
<220> FEATURE:
<223> OTHER INFORMATION: Synthetic construct:  Nucleotide
      sequence encoding NsD2 from Nicotiana suaveolens

<400> SEQUENCE: 50
aaagattgca aaagagaaag caatacattc cctggaatat gcattaccaa actaccatgc      60
agaagagctt gtatcagtga gaaatttgct gatggtcatt gtagcaaaat cctcagaagg     120
tgtctatgca ctaagccatg t                                                141

<210> SEQ ID NO 51
<211> LENGTH: 47
<212> TYPE: PRT
<213> ORGANISM: Artificial Sequence
<220> FEATURE:
<223> OTHER INFORMATION: Synthetic construct:  Amino acid sequence
      encoding NsD2

<400> SEQUENCE: 51

Lys Asp Cys Lys Arg Glu Ser Asn Thr Phe Pro Gly Ile Cys Ile Thr
1               5                   10                  15

Lys Leu Pro Cys Arg Arg Ala Cys Ile Ser Glu Lys Phe Ala Asp Gly
            20                  25                  30

His Cys Ser Lys Ile Leu Arg Arg Cys Leu Cys Thr Lys Pro Cys
        35                  40                  45

<210> SEQ ID NO 52
<211> LENGTH: 20
<212> TYPE: PRT
<213> ORGANISM: Artificial Sequence
<220> FEATURE:
<223> OTHER INFORMATION: Synthetic construct:  Amino acid sequence of
      C-terminal end amino acid sequence of NaD1 which ends and
      includes the most C-terminal invariant cysteine residue

<400> SEQUENCE: 52

Lys Phe Thr Asp Gly His Cys Ser Lys Ile Leu Arg Arg Cys Leu Cys
1               5                   10                  15

Thr Lys Pro Cys
            20

<210> SEQ ID NO 53
<211> LENGTH: 33
<212> TYPE: PRT
<213> ORGANISM: Artificial Sequence
<220> FEATURE:
<223> OTHER INFORMATION: Synthetic construct:  Amino acid sequence of
      NaD1 C-terminal tail

<400> SEQUENCE: 53

Val Phe Asp Glu Lys Met Thr Lys Thr Gly Ala Glu Ile Leu Ala Glu
1               5                   10                  15

Glu Ala Lys Thr Leu Ala Ala Ala Leu Leu Glu Glu Glu Ile Met Asp
            20                  25                  30

Asn

```
<210> SEQ ID NO 54
<211> LENGTH: 6
<212> TYPE: PRT
<213> ORGANISM: Artificial Sequence
<220> FEATURE:
<223> OTHER INFORMATION: Synthetic construct: Amino acid sequence of
      variable region of Loop 1B region
<220> FEATURE:
<221> NAME/KEY: MISC_FEATURE
<222> LOCATION: (1)..(1)
<223> OTHER INFORMATION: Xaa = N, G, D, H, K, A, E, Q, T, P, L, M, S
      or R
<220> FEATURE:
<221> NAME/KEY: MISC_FEATURE
<222> LOCATION: (2)..(2)
<223> OTHER INFORMATION: Xaa = K, R, G, H, L, N, F ,I, S, T or Y
<220> FEATURE:
<221> NAME/KEY: MISC_FEATURE
<222> LOCATION: (3)..(3)
<223> OTHER INFORMATION: Xaa = W, Y, H, L, G, F or P
<220> FEATURE:
<221> NAME/KEY: MISC_FEATURE
<222> LOCATION: (4)..(4)
<223> OTHER INFORMATION: Xaa = P, K, S, R, H, T, E, V, N, Q, D or G
<220> FEATURE:
<221> NAME/KEY: MISC_FEATURE
<222> LOCATION: (5)..(5)
<223> OTHER INFORMATION: Xaa = S, K, Y, F, G or H
<220> FEATURE:
<221> NAME/KEY: MISC_FEATURE
<222> LOCATION: (6)..(6)
<223> OTHER INFORMATION: Xaa = P, V, L, T, A ,F, N, K, R, M, G, H, I
      or Y

<400> SEQUENCE: 54

Xaa Xaa Xaa Xaa Xaa Xaa
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic construct: Amino acid sequence of
      variable region of Loop 1B region
<220> FEATURE:
<221> NAME/KEY: MISC_FEATURE
<222> LOCATION: (1)..(1)
<223> OTHER INFORMATION: Xaa = N, H, Q, D, K or E
<220> FEATURE:
<221> NAME/KEY: MISC_FEATURE
<222> LOCATION: (2)..(2)
<223> OTHER INFORMATION: Xaa = R, H, T, K or G
<220> FEATURE:
<221> NAME/KEY: MISC_FEATURE
<222> LOCATION: (3)..(3)
<223> OTHER INFORMATION: Xaa = F, H, Y or W
<220> FEATURE:
<221> NAME/KEY: MISC_FEATURE
<222> LOCATION: (4)..(4)
<223> OTHER INFORMATION: Xaa = P, K, S or R
<220> FEATURE:
<221> NAME/KEY: MISC_FEATURE
<222> LOCATION: (5)..(5)
<223> OTHER INFORMATION: Xaa = G or F
<220> FEATURE:
<221> NAME/KEY: MISC_FEATURE
<222> LOCATION: (6)..(6)
<223> OTHER INFORMATION: Xaa = P, V, I or N

<400> SEQUENCE: 55

Xaa Xaa Xaa Xaa Xaa Xaa
1               5
```

```
<210> SEQ ID NO 56
<211> LENGTH: 6
<212> TYPE: PRT
<213> ORGANISM: Artificial Sequence
<220> FEATURE:
<223> OTHER INFORMATION: Synthetic construct: Amino acid sequence
      of variable region of Loop 1B region
<220> FEATURE:
<221> NAME/KEY: MISC_FEATURE
<222> LOCATION: (1)..(1)
<223> OTHER INFORMATION: Xaa = L, F, S, I, A, H, Y, Q, D, K or G
<220> FEATURE:
<221> NAME/KEY: MISC_FEATURE
<222> LOCATION: (2)..(2)
<223> OTHER INFORMATION: Xaa = S, V, F, I, K, L, A, P, N, T, R, H or G
<220> FEATURE:
<221> NAME/KEY: MISC_FEATURE
<222> LOCATION: (3)..(3)
<223> OTHER INFORMATION: Xaa = A, F, W, N, I, S, Y, P, L or H
<220> F

```
                    20                  25                  30

His Cys Ser Lys Ile Leu Arg Arg Cys Leu Cys Thr Lys Pro Cys
        35                  40                  45

<210> SEQ ID NO 58
<211> LENGTH: 49
<212> TYPE: PRT
<213> ORGANISM: Artificial Sequence
<220> FEATURE:
<223> OTHER INFORMATION: Synthetic construct:  Amino acid sequence of
      C20

<400> SEQUENCE: 58

Gln Asn Ile Cys Lys Thr Thr Ser Lys Tyr Phe Lys Gly Leu Cys Ile
1               5                   10                  15

Thr Asp Ser Ser Cys Arg Lys Val Cys Ile Glu Lys Asp Lys Phe Glu
                20                  25                  30

Asp Gly His Cys Ser Lys Leu Gln Arg Lys Cys Leu Cys Thr Lys Leu
        35                  40                  45

Cys

<210> SEQ ID NO 59
<211> LENGTH: 47
<212> TYPE: PRT
<213> ORGANISM: Artificial Sequence
<220> FEATURE:
<223> OTHER INFORMATION: Synthetic construct:  Amino acid sequence of
      SL549

<400> SEQUENCE: 59

Lys Asp Cys Lys Arg Glu Ser Asn Thr Phe Pro Gly Ile Cys Leu Thr
1               5                   10                  15

Lys Pro Pro Cys Arg Lys Ala Cys Ile Lys Glu Lys Phe Thr Asp Gly
                20                  25                  30

His Cys Ser Lys Ile Leu Arg Arg Cys Leu Cys Thr Lys Pro Cys
        35                  40                  45

<210> SEQ ID NO 60
<211> LENGTH: 6
<212> TYPE: PRT
<213> ORGANISM: Artificial Sequence
<220> FEATURE:
<223> OTHER INFORMATION: Synthetic construct:  Amino acid sequence of
      Loop 1B from C20

<400> SEQUENCE: 60

Lys Tyr Phe Lys Gly Leu
1               5

<210> SEQ ID NO 61
<211> LENGTH: 72
<212> TYPE: PRT
<213> ORGANISM: Artificial Sequence
<220> FEATURE:
<223> OTHER INFORMATION: Synthetic construct:  Amino acid sequence of
      NaPin1A

<400> SEQUENCE: 61

Gln Ser Gly Cys Pro Gly Val Thr Lys Glu Arg Trp Pro Glu Leu Leu
1               5                   10                  15

Gly Thr Pro Ala Lys Phe Ala Met Gln Ile Ile Gln Lys Glu Asn Pro
                20                  25                  30

Lys Leu Thr Asn Val Gln Thr Ile Leu Asn Gly Arg Pro Val Thr Glu
```

```
            35                  40                  45
Asp Leu Arg Cys Asn Arg Val Arg Leu Phe Val Asn Val Leu Asp Phe
         50                  55                  60

Val Val Gln Thr Pro Gln Val Gly
 65                  70

<210> SEQ ID NO 62
<211> LENGTH: 65
<212> TYPE: PRT
<213> ORGANISM: Artificial Sequence
<220> FEATURE:
<223> OTHER INFORMATION: Synthetic construct:  Amino acid sequence of
      BPTI

<400> SEQUENCE: 62

Arg Pro Asp Phe Cys Leu Glu Pro Pro Tyr Thr Gly Pro Cys Lys Ala
  1               5                  10                  15

Arg Ile Ile Arg Tyr Phe Tyr Asn Ala Lys Ala Gly Leu Cys Gln Thr
             20                  25                  30

Phe Val Tyr Gly Gly Cys Arg Ala Lys Arg Asn Asn Phe Lys Ser Ala
         35                  40                  45

Glu Asp Cys Met Arg Thr Cys Gly Gly Ala Ile Gly Pro Trp Glu Asn
     50                  55                  60

Leu
 65

<210> SEQ ID NO 63
<211> LENGTH: 83
<212> TYPE: PRT
<213> ORGANISM: Artificial Sequence
<220> FEATURE:
<223> OTHER INFORMATION: Synthetic construct:  Amino acid sequence of
      CI-1B

<400> SEQUENCE: 63

Met Arg Ser Met Glu Gly Ser Val Pro Lys Tyr Pro Glu Pro Thr Glu
  1               5                  10                  15

Gly Ser Ile Gly Ala Ser Gly Ala Lys Arg Ser Trp Pro Glu Val Val
             20                  25                  30

Gly Met Ser Ala Glu Lys Ala Lys Glu Ile Ile Leu Arg Asp Lys Pro
         35                  40                  45

Asp Ala Gln Ile Glu Val Ile Pro Val Asp Ala Met Val Pro Leu Asp
     50                  55                  60

Phe Asn Pro Asn Arg Ile Phe Ile Leu Val Ala Val Ala Arg Thr Pro
 65                  70                  75                  80

Thr Val Gly

<210> SEQ ID NO 64
<211> LENGTH: 235
<212> TYPE: PRT
<213> ORGANISM: Artificial Sequence
<220> FEATURE:
<223> OTHER INFORMATION: Synthetic construct:  Amino acid sequence of
      HVCPI6

<400> SEQUENCE: 64

Met Arg Val Ile Arg Ser Arg Ala Ile Leu Ile Val Leu Phe Leu Val
  1               5                  10                  15

Ser Ala Phe Gly Leu Ser Glu Gln Gly Lys Ser Gly Phe Cys Ser
             20                  25                  30
```

```
Glu Glu Met Ala Thr Leu Gly Gly Val His Asp Ser His Gly Ser Ser
            35                  40                  45

Gln Asn Ser Asp Glu Ile His Ser Leu Ala Lys Phe Ala Val Asp Glu
 50                  55                  60

His Asn Lys Lys Glu Asn Ala Met Ile Glu Leu Ala Arg Val Val Lys
 65                  70                  75                  80

Ala Gln Glu Gln Thr Val Ala Gly Lys Leu His His Leu Thr Leu Glu
                85                  90                  95

Val Met Asp Ala Gly Lys Lys Leu Tyr Glu Ala Lys Val Trp Val
                100                 105                 110

Lys Pro Trp Leu Asn Phe Lys Glu Leu Gln Glu Phe Lys His Val Glu
                115                 120                 125

Asp Val Pro Thr Phe Thr Ser Ser Asp Leu Gly Val Lys Gln Val Glu
 130                 135                 140

Gln Asn Ser Gly Leu Lys Ser Val Pro Val His Asp Pro Val Val Glu
 145                 150                 155                 160

Glu Ala Ala Glu His Ala Ile Lys Thr Ile Gln Gln Arg Ser Asn Ser
                165                 170                 175

Ile His Pro Tyr Lys Leu Gln Glu Ile Val His Ala Asn Ala Glu Met
                180                 185                 190

Ala Asp Asp Ser Thr Lys Leu His Leu Val Ile Lys Thr Ser Arg Gly
                195                 200                 205

Gly Lys Glu Glu Lys Phe Lys Val Gln Val Gln His Asn Asn Glu Gly
                210                 215                 220

Ala Phe His Leu Asn Arg Met Glu Pro Asp Asn
 225                 230                 235

<210> SEQ ID NO 65
<211> LENGTH: 102
<212> TYPE: PRT
<213> ORGANISM: Artificial Sequence
<220> FEATURE:
<223> OTHER INFORMATION: Synthetic construct:  Amino acid sequence of
      S1Cys9

<400> SEQUENCE: 65

Met Ser Ser Asp Gly Gly Pro Val Leu Gly Val Glu Pro Val Gly
  1               5                  10                  15

Asn Glu Asn Asp Leu His Leu Val Asp Leu Ala Arg Phe Ala Val Thr
                20                  25                  30

Glu His Asn Lys Lys Ala Asn Ser Leu Leu Glu Phe Glu Lys Leu Val
                35                  40                  45

Ser Val Lys Gln Gln Val Val Ala Gly Thr Leu Tyr Tyr Phe Thr Ile
 50                  55                  60

Glu Val Lys Glu Gly Asp Ala Lys Lys Leu Tyr Glu Ala Lys Val Trp
 65                  70                  75                  80

Glu Lys Pro Trp Met Asp Phe Lys Glu Leu Gln Glu Phe Lys Pro Val
                85                  90                  95

Asp Ala Ser Ala Asn Ala
                100

<210> SEQ ID NO 66
<211> LENGTH: 102
<212> TYPE: PRT
<213> ORGANISM: Artificial Sequence
<220> FEATURE:
<223> OTHER INFORMATION: Synthetic construct:  Amino acid sequence of
      OsIa
```

<400> SEQUENCE: 66

Ala Thr Ser Ala Leu Gly Arg Arg Gly Val Leu Leu Gly Gly Trp Ser
1               5                   10                  15

Pro Val Lys Asp Val Asn Asp Pro His Val Gln Glu Leu Gly Gly Trp
            20                  25                  30

Ala Val Ala Gln His Ala Ser Leu Ala Lys Asp Gly Leu Leu Phe Arg
        35                  40                  45

Arg Val Thr Arg Gly Glu Gln Val Val Ser Gly Met Asn Tyr Arg
    50                  55                  60

Leu Phe Val Val Ala Ala Asp Gly Ser Gly Lys Arg Val Thr Tyr Leu
65                  70                  75                  80

Ala Gln Ile Tyr Glu His Trp Ser Arg Thr Arg Lys Leu Thr Ser Phe
                85                  90                  95

Lys Pro Ala Ala Gly Gly
            100

<210> SEQ ID NO 67
<211> LENGTH: 6
<212> TYPE: PRT
<213> ORGANISM: Artificial Sequence
<220> FEATURE:
<223> OTHER INFORMATION: Synthetic construct: Amino acid sequence of
      replacement Loop 1B identified following high through put screen

<400> SEQUENCE: 67

Leu Ser Phe Lys Gly Thr
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic construct: Amino acid sequence of
      replacement Loop 1B identified following high through put screen

<400> SEQUENCE: 68

Leu Val Phe Gly Gly Met
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic construct: Amino acid sequence of
      replacement Loop 1B identified following high through put screen

<400> SEQUENCE: 69

Tyr Asn Pro Val Gly Leu
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic construct: Amino acid sequence of
      replacement Loop 1B identified following high through put screen

<400> SEQUENCE: 70

Leu Phe Trp Glu Lys Ser
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic construct: Amino acid sequence of
      replacement Loop 1B identified following high through put screen

<400> SEQUENCE: 71

Ser Pro Phe Val Gly Pro
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic construct: Amino acid sequence of
      replacement Loop 1B identified following high through put screen

<400> SEQUENCE: 72

Ser Ile Ile Ala Ser Ala
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic construct: Amino acid sequence of
      replacement Loop 1B identified following high through put screen

<400> SEQUENCE: 73

Ile Lys Ala Pro Gly Trp
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic construct: Amino acid sequence of
      replacement Loop 1B identified following high through put screen

<400> SEQUENCE: 74

Leu Thr Leu Ser Asn His
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic construct: Amino acid sequence of
      replacement Loop 1B identified following high through put screen

<400> SEQUENCE: 75

Leu Ile Ser Phe Tyr Pro
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic construct: Amino acid sequence of
      replacement Loop 1B identified following high through put screen -continued

```
<400> SEQUENCE: 76

Ala Leu Phe Ala Gly Glu
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic construct:  Amino acid sequence of
      replacement Loop 1B identified following high through put screen

<400> SEQUENCE: 77

Phe Leu Tyr Arg Glu Lys
1               5

<210> SEQ ID NO 78
<211> LENGTH: 6
<212> TYPE: PRT
<213> ORGANISM: Artificial Sequence
<220> FEATURE:
<223> OTHER INFORMATION: Synthetic construct:  Amino acid sequence of
      replacement Loop 1B identified following high through put screen

<400> SEQUENCE: 78

Phe Ile Phe Arg Met Glu
1               5

<210> SEQ ID NO 79
<211> LENGTH: 6
<212> TYPE: PRT
<213> ORGANISM: Artificial Sequence
<220> FEATURE:
<223> OTHER INFORMATION: Synthetic construct:  Amino acid sequence of
      replacement Loop 1B identified following high through put screen

<400> SEQUENCE: 79

His Ala Phe Gln Lys Gly
1               5

<210> SEQ ID NO 80
<211> LENGTH: 381
<212> TYPE: DNA
<213> ORGANISM: Artificial Sequence
<220> FEATURE:
<223> OTHER INFORMATION: Synthetic construct:  HvCPI6 for expression in
      corn

<400> SEQUENCE: 80
atggccaaca agcacctgtc cctctccctc ttcctcgtgc tcctcggcct ctccgcctcc      60
ctcgcctccg agccaccctc ggccctcggc cgccgcggcg tgcttctggg cgggtggagc     120
cccgtcaagg acgtgaacga cccgcacgtc caggagctag gcgggtgggc ggtggcccag     180
cacgccagcc tagccaagga cgggctgctc ttccgccggg tgacgcgcgg cgagcagcag     240
gtggtgtccg ggatgaacta ccgcctcttc gtggtcgcgg cggacggctc cggcaagagg     300
gtgacctatc tcgcgcagat ctacgagcac tggagcagga cccgcaagct cacgtccttc     360
aagccggctg ccggcggctg a                                               381

<210> SEQ ID NO 81
<211> LENGTH: 126
<212> TYPE: PRT
<213> ORGANISM: Artificial Sequence
<220> FEATURE:
```

<223> OTHER INFORMATION: Synthetic construct: Amino acid sequence of
      HvCPI6 for expression in corn

<400> SEQUENCE: 81

Met Ala Asn Lys His Leu Ser Leu Ser Leu Phe Leu Val Leu Leu Gly
1               5                   10                  15

Leu Ser Ala Ser Leu Ala Ser Gly Ala Thr Ser Ala Leu Gly Arg Arg
            20                  25                  30

Gly Val Leu Leu Gly Gly Trp Ser Pro Val Lys Asp Val Asn Asp Pro
        35                  40                  45

His Val Gln Glu Leu Gly Gly Trp Ala Val Ala Gln His Ala Ser Leu
    50                  55                  60

Ala Lys Asp Gly Leu Leu Phe Arg Arg Val Thr Arg Gly Glu Gln Gln
65                  70                  75                  80

Val Val Ser Gly Met Asn Tyr Arg Leu Phe Val Val Ala Ala Asp Gly
                85                  90                  95

Ser Gly Lys Arg Val Thr Tyr Leu Ala Gln Ile Tyr Glu His Trp Ser
            100                 105                 110

Arg Thr Arg Lys Leu Thr Ser Phe Lys Pro Ala Ala Gly Gly
        115                 120                 125

<210> SEQ ID NO 82
<211> LENGTH: 636
<212> TYPE: DNA
<213> ORGANISM: Artificial Sequence
<220> FEATURE:
<223> OTHER INFORMATION: Synthetic construct:  HvCPI6-L-HXP4-CTPP

<400> SEQUENCE: 82
atggccaaca agcacctgtc cctctccctc ttcctcgtgc tcctcggcct ctccgcctcc      60
ctcgcctccg gagccacctc ggccctcggc cgccgcggcg tgcttctggg cgggtggagc     120
cccgtcaagg acgtgaacga cccgcacgtc caggagctag gcgggtgggc ggtggcccag     180
cacgccagcc tagccaagga cgggctgctc ttccgccggg tgacgcgcgg cgagcagcag     240
gtggtgtccg ggatgaacta ccgcctcttc gtggtcgcgg cggacggctc cggcaagagg     300
gtgacctatc tcgcgcagat ctacgagcac tggagcagga cccgcaagct cacgtccttc     360
aagccggctg ccggcggcga ggagaagaag aacagggagt gcaaaacaga gagcaacacg     420
ttccctggca tctgcattac taagccaccg tgccgcaagg cctgcatctc cgaaaagttt     480
acagacgggc actgttccaa aatcctccgc aggtgcctct gcacgaagcc gtgcgttttc     540
gacgagaaga tgacgaagac tggggcggag attctcgctg aggaggccaa gactctggcg     600
gctgccctgc tggaagagga aattatggac aattga                              636

<210> SEQ ID NO 83
<211> LENGTH: 211
<212> TYPE: PRT
<213> ORGANISM: Artificial Sequence
<220> FEATURE:
<223> OTHER INFORMATION: Synthetic construct:  Amino acid sequence of
      HvCPI6-L-HXP4-CTPP

<400> SEQUENCE: 83

Met Ala Asn Lys His Leu Ser Leu Ser Leu Phe Leu Val Leu Leu Gly
1               5                   10                  15

Leu Ser Ala Ser Leu Ala Ser Gly Ala Thr Ser Ala Leu Gly Arg Arg
            20                  25                  30

Gly Val Leu Leu Gly Gly Trp Ser Pro Val Lys Asp Val Asn Asp Pro

```
                35                  40                  45
His Val Gln Glu Leu Gly Gly Trp Ala Val Ala Gln His Ala Ser Leu
 50                  55                  60

Ala Lys Asp Gly Leu Leu Phe Arg Arg Val Thr Arg Gly Glu Gln Gln
 65                  70                  75                  80

Val Val Ser Gly Met Asn Tyr Arg Leu Phe Val Val Ala Ala Asp Gly
                 85                  90                  95

Ser Gly Lys Arg Val Thr Tyr Leu Ala Gln Ile Tyr Glu His Trp Ser
                100                 105                 110

Arg Thr Arg Lys Leu Thr Ser Phe Lys Pro Ala Ala Gly Gly Glu Glu
                115                 120                 125

Lys Lys Asn Arg Glu Cys Lys Thr Glu Ser Asn Thr Phe Pro Gly Ile
 130                 135                 140

Cys Ile Thr Lys Pro Pro Cys Arg Lys Ala Cys Ile Ser Glu Lys Phe
 145                 150                 155                 160

Thr Asp Gly His Cys Ser Lys Ile Leu Arg Arg Cys Leu Cys Thr Lys
                165                 170                 175

Pro Cys Val Phe Asp Glu Lys Met Thr Lys Thr Gly Ala Glu Ile Leu
                180                 185                 190

Ala Glu Glu Ala Lys Thr Leu Ala Ala Ala Leu Leu Glu Glu Glu Ile
                195                 200                 205

Met Asp Asn
    210

<210> SEQ ID NO 84
<211> LENGTH: 47
<212> TYPE: PRT
<213> ORGANISM: Artificial Sequence
<220> FEATURE:
<223> OTHER INFORMATION: Synthetic construct:  Amino acid sequence of
      NaD1 backbone having a Loop 1B defined by X1 through X6
<220> FEATURE:
<221> NAME/KEY: MISC_FEATURE
<222> LOCATION: (8)..(8)
<223> OTHER INFORMATION: Xaa = N, H, Q, D, K or E
<220> FEATURE:
<221> NAME/KEY: MISC_FEATURE
<222> LOCATION: (9)..(9)
<223> OTHER INFORMATION: Xaa = R, H, T, K or G
<220> FEATURE:
<221> NAME/KEY: MISC_FEATURE
<222> LOCATION: (10)..(10)
<223> OTHER INFORMATION: Xaa = F, H, Y or W
<220> FEATURE:
<221> NAME/KEY: MISC_FEATURE
<222> LOCATION: (11)..(11)
<223> OTHER INFORMATION: Xaa = P, K, S or R
<220> FEATURE:
<221> NAME/KEY: MISC_FEATURE
<222> LOCATION: (12)..(12)
<223> OTHER INFORMATION: Xaa = G or F
<220> FEATURE:
<221> NAME/KEY: MISC_FEATURE
<222> LOCATION: (13)..(13)
<223> OTHER INFORMATION: Xaa = P, V, I or N

<400> SEQUENCE: 84

Arg Glu Cys Lys Thr Glu Ser Xaa Xaa Xaa Xaa Xaa Xaa Cys Ile Thr
 1               5                  10                  15

Lys Pro Pro Cys Arg Lys Ala Cys Ile Ser Glu Lys Phe Thr Asp Gly
                20                  25                  30

His Cys Ser Lys Ile Leu Arg Arg Cys Leu Cys Thr Lys Pro Cys
                35                  40                  45
```

```
<210> SEQ ID NO 85
<211> LENGTH: 48
<212> TYPE: PRT
<213> ORGANISM: Artificial Sequence
<220> FEATURE:
<223> OTHER INFORMATION: Synthetic construct:  TPP3 backbone with NaD2
      Loop 1B

<400> SEQUENCE: 85

Gln Gln Ile Cys Lys Ala Pro Ser His Arg Phe Lys Gly Pro Cys Phe
1               5                   10                  15

Met Asp Ser Ser Cys Arg Lys Tyr Cys Ile Lys Glu Lys Phe Thr Gly
                20                  25                  30

Gly His Cys Ser Lys Leu Gln Arg Lys Cys Leu Cys Thr Lys Pro Cys
                35                  40                  45

<210> SEQ ID NO 86
<211> LENGTH: 6
<212> TYPE: PRT
<213> ORGANISM: Artificial Sequence
<220> FEATURE:
<223> OTHER INFORMATION: Synthetic construct:  Amino acid sequence of
      modified Loop 1B
<220> FEATURE:
<221> NAME/KEY: MISC_FEATURE
<222> LOCATION: (1)..(1)
<223> OTHER INFORMATION: X1 = N, G, D, H, K, A, E, Q, T, P, L, M, S,
      or R
<220> FEATURE:
<221> NAME/KEY: MISC_FEATURE
<222> LOCATION: (2)..(2)
<223> OTHER INFORMATION: X2 = K, R, G, H, L, N, F, I, S, T or Y
<220> FEATURE:
<221> NAME/KEY: MISC_FEATURE
<222> LOCATION: (3)..(3)
<223> OTHER INFORMATION: X3 = W, Y, H, L, G, F or P
<220> FEATURE:
<221> NAME/KEY: MISC_FEATURE
<222> LOCATION: (4)..(4)
<223> OTHER INFORMATION: X4 = P, K, S, R, H, T, E, V, N, Q, D or G
<220> FEATURE:
<221> NAME/KEY: MISC_FEATURE
<222> LOCATION: (5)..(5)
<223> OTHER INFORMATION: X5 = S, K, Y, F, G or H
<220> FEATURE:
<221> NAME/KEY: MISC_FEATURE
<222> LOCATION: (6)..(6)
<223> OTHER INFORMATION: X6 = P, V, L, T, A, F, N, K, R, M, G, H, I or Y

<400> SEQUENCE: 86

Xaa Xaa Xaa Xaa Xaa Xaa
1               5

<210> SEQ ID NO 87
<211> LENGTH: 6
<212> TYPE: PRT
<213> ORGANISM: Artificial Sequence
<220> FEATURE:
<223> OTHER INFORMATION: Synthetic construct:  Amino acid sequence of
      modified Loop 1B
<220> FEATURE:
<221> NAME/KEY: MISC_FEATURE
<222> LOCATION: (1)..(1)
<223> OTHER INFORMATION: X1 = G, D, H, K, A, E, Q, T, P, L, M, S, or R
<220> FEATURE:
<221> NAME/KEY: MISC_FEATURE
<222> LOCATION: (2)..(2)
<223> OTHER INFORMATION: X2 = K, R, G, H, L, N, F, I, S or Y
<220> FEATURE:
<221> NAME/KEY: MISC_FEATURE
<222> LOCATION: (3)..(3)
<223> OTHER INFORMATION: X3 = W, Y, H, L, G, F or P
```

```
<220> FEATURE:
<221> NAME/KEY: MISC_FEATURE
<222> LOCATION: (4)..(4)
<223> OTHER INFORMATION: X4 = K, S, R, H, T, E, V, N, Q, D or G
<220> FEATURE:
<221> NAME/KEY: MISC_FEATURE
<222> LOCATION: (5)..(5)
<223> OTHER INFORMATION: X5 = S, K, Y, F or H
<220> FEATURE:
<221> NAME/KEY: MISC_FEATURE
<222> LOCATION: (6)..(6)
<223> OTHER INFORMATION: X6 = P, V, L, T, A, F, N, K, R, M, G, H or Y

<400> SEQUENCE: 87

Xaa Xaa Xaa Xaa Xaa Xaa
1               5

<210> SEQ ID NO 88
<211> LENGTH: 6
<212> TYPE: PRT
<213> ORGANISM: Artificial Sequence
<220> FEATURE:
<223> OTHER INFORMATION: Synthetic construct:  Amino acid sequence of
      Loop 1B from Colletotrichum-inhibiting protein

<400> SEQUENCE: 88

Leu Ser Ala Lys Met Val
1               5

<210> SEQ ID NO 89
<211> LENGTH: 6
<212> TYPE: PRT
<213> ORGANISM: Artificial Sequence
<220> FEATURE:
<223> OTHER INFORMATION: Synthetic construct:  Amino acid sequence of
      Loop 1B from Colletotrichum-inhibiting protein

<400> SEQUENCE: 89

Phe Ile Asn Arg Asp Trp
1               5

<210> SEQ ID NO 90
<211> LENGTH: 6
<212> TYPE: PRT
<213> ORGANISM: Artificial Sequence
<220> FEATURE:
<223> OTHER INFORMATION: Synthetic construct:  Amino acid sequence of
      Loop 1B from Colletotrichum-inhibiting protein

<400> SEQUENCE: 90

Leu Val Ser Phe Pro Gly
1               5

<210> SEQ ID NO 91
<211> LENGTH: 5
<212> TYPE: PRT
<213> ORGANISM: Artificial Sequence
<220> FEATURE:
<223> OTHER INFORMATION: Synthetic construct:  Amino acid sequence of
      Loop 1B

<400> SEQUENCE: 91

Glu Gly Trp Gly Lys
1               5
```